(12) United States Patent
Okano et al.

(10) Patent No.: US 7,718,663 B2
(45) Date of Patent: May 18, 2010

(54) QUINAZOLINE DERIVATIVES AND MEDICAMENTS

(75) Inventors: Masahiko Okano, Kyoto (JP); Tatsuya Oyama, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 713 days.

(21) Appl. No.: 10/512,954

(22) PCT Filed: Apr. 28, 2003

(86) PCT No.: PCT/JP03/05432

§ 371 (c)(1),
(2), (4) Date: Oct. 26, 2004

(87) PCT Pub. No.: WO03/091224

PCT Pub. Date: Nov. 6, 2003

(65) Prior Publication Data

US 2005/0176741 A1    Aug. 11, 2005

(30) Foreign Application Priority Data

Apr. 26, 2002 (JP) ............................. 2002-125452
Sep. 18, 2002 (JP) ............................. 2002-272314
Dec. 25, 2002 (JP) ............................. 2002-373400

(51) Int. Cl.
*A61K 31/517* (2006.01)
*C07D 239/94* (2006.01)

(52) U.S. Cl. .................. 514/266.23; 514/266.4; 544/284; 544/293

(58) Field of Classification Search ............ 514/266.4, 514/266.23; 544/292, 284, 293
See application file for complete search history.

(56) References Cited

U.S. PATENT DOCUMENTS 5,106,851 A * 4/1992 Turconi et al. ......... 514/266.21
6,794,389 B2 * 9/2004 Okana et al. ........... 514/252.17

2003/0139431 A1 * 7/2003 Kawakami et al. ....... 514/266.4

FOREIGN PATENT DOCUMENTS

CA        2403605    *  9/2002
WO   WO-01/72710 A1   10/2001
WO   WO-02/074341 A1   9/2002

OTHER PUBLICATIONS

Sakurada, Tsukasa et al.; "Evidence that N-terminal fragments of nociceptin modulate nociceptin-induced scratching, biting and licking in mice"; Neuroscience Letters, 2000, vol. 279, No. 1, pp. 61-64.

* cited by examiner

*Primary Examiner*—James O Wilson
*Assistant Examiner*—Tamthom N Truong
(74) *Attorney, Agent, or Firm*—Darby & Darby P.C.

(57) ABSTRACT

An object of the present invention is to provide an antipruritic agent having a novel action mechanism.

The present invention provides an antipruritic agent comprising a compound represented by the following general formula (1):

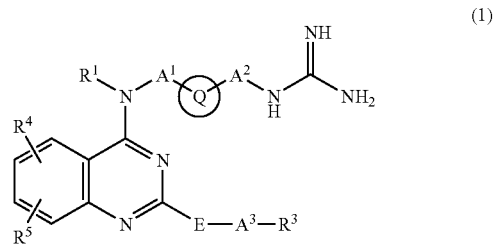

(1)

wherein $R^1$ represents a hydrogen atom or alkyl; the ring Q represents a cyclohexylene group or a phenylene group; $A^1$ and $A^2$ represent a single bond or an alkylene group; E represents —NHCO—; $A^3$ represents a single bond or a divalent saturated or unsaturated aliphatic hydrocarbon group; $R^3$ represents a non-cyclic aliphatic hydrocarbon group; and $R^4$ and $R^5$ are the same or different and each represents a hydrogen atom or alkyl, or a pharmaceutically acceptable salt thereof as an active ingredient.

18 Claims, No Drawings

QUINAZOLINE DERIVATIVES AND MEDICAMENTS

CROSS-REFERENCE TO PRIOR APPLICATION

This is a U.S. national phase application under 35 U.S.C. §371 of International Patent Application No. PCT/JP03/05432 filed Apr. 28, 2003, and claims the benefit of Japanese Patent Application No. 2002-125452 filed Apr. 26, 2002, Application No. 2002-272314 filed Sep. 18, 2002 and Application No. 2002-3737400 filed Dec. 18, 2002 which are incorporated by reference herein. The International Application was published in Japanese on Nov. 6, 2003 as WO 03/091224 A1 under PCT Article 21(2).

TECHNICAL FIELD

The present invention relates to quinazoline derivatives, which are useful as medicaments, particularly antipruritic agents, or salts thereof and pharmaceutical compositions containing any of them as active ingredients.

BACKGROUND ART

Itching is a sensation (pruritic sensation), which takes place at the cortex of the skin and the mucosa adjacent to the skin. The pruritic sensation is a sensation, which senses a parasite and an irritant of the skin cortex and removes an invading substance and an irritant by a scratching operation. Itching is a sensation, which can be easily understood as a sensation causing an impulse to scratch, but its mechanism has not been elucidated completely.

Diseases associated with itching are roughly classified into pruritic dermatitis associated with skin lesion (for example, atopic dermatitis, urticaria, psoriasis, xeroderma and trichophytia) and pruritus cutaneous which is not associated with skin lesion and provokes itching due to kidney dialysis and internal diseases [for example, diabetes, blood disease, cholestatic hepatitis (primary biliary liver cirrhosis) and kidney disease], hyperthyroidism and multiple sclerosis. In addition, the disease associated with severe itching includes diseases of cornea and conjunctiva, for example, allergic conjunctivitis. Recently, all diseases have rapidly increased to constitute a large problem in view of QOL (quality of life). Most itching diseases are common in the fact that vicious circle is caused by injure due to scratching. Histamine is known as a typical itching-producing substance and provokes itching in case it is externally added and is internally isolated from mastocytes.

An antihistaminic agent, an antiallergic agent and a steroid external agent are used for the treatment of pruritic dermatitis. However, all of them are not satisfactory medicaments for the treatment of itching due to pruritic dermatitis. Also it has recently been reported that elements other than histamine take part in itching due to atopic dermatitis. In many clinical cases, the antihistaminic agent and the antiallergic agent do not actually exert a remarkable effect on itching due to atopic dermatitis. In the treatment of pruritus cutaneous, the antihistaminic agent or the steroid external agent is employed sometimes, however, they do not exert any effect, and thus an effective therapy does not exist at present. As described above, there are no satisfactory medicaments for diseases associated with itching and it is required to develop a medicament, which effectively suppresses itching regardless of causative diseases from a clinical point of view.

The present inventors have found that a quinazoline derivative has a nociceptin antagonism and is useful as an analgesic (see Patent Document 1).

Patent Document 2 describes, as a compound having a carbonylamino group at the 2-position of the quinazoline skeleton, a quinazoline derivative that has a neuropeptide Y (NPY) receptor subtype Y5 inhibitory effect and is useful for pain relief and memory disorder. Patent Document 3 describes a quinazoline derivative, which is useful for bone diseases. Patent Document 4 describes a quinazoline derivative, which has a LTB4 (leucotriene B4) antagonism and is useful as an anti-inflammatory. However, these compounds have no guanidino group on the side chain at the 4-position of the quinazoline skeleton.

Patent Document 1: International Publication WO01/72710
Patent Document 2: International Publication WO97/20821
Patent Document 3: International Publication WO98/17267
Patent Document 4: International Publication WO98/38984

DISCLOSURE OF THE INVENTION

An object of the present invention is to provide an excellent antipruritic agent having a novel action mechanism.

The present inventors have intensively studied so as to develop a medicament having an action mechanism, which suppresses a transmission path of a pruritic sensation. As a result, they have found that a compound of the general formula (1) (hereinafter referred to as an "inventive compound") has a nociceptin antagonism and also has an antipruritic effect. Thus, the present invention has been completed.

The present invention provides:
(A) a quinazoline derivative represented by the following general formula (1) or a salt thereof:

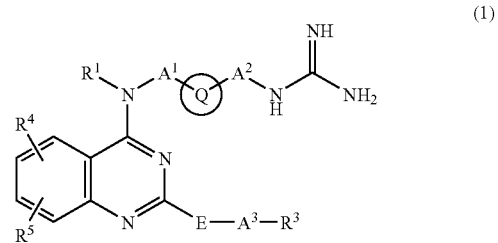

(1)

wherein $R^1$ represents a hydrogen atom or alkyl;

the ring Q represents a cyclohexylene group or a phenylene group;

$A^1$ and $A^2$ are the same or different and each represents a single bond or an alkylene group;

E represents —NHCO— or —CON($R^2$)— (wherein $R^2$ represents a hydrogen atom or alkyl);

$A^3$ represents $A^{31}$-$A^{32}$-$A^{33}$;

$A^{31}$ and $A^{33}$ are the same or different and each represents a single bond, or a divalent saturated or unsaturated aliphatic hydrocarbon group having 1 to 6 carbon atoms which may have the same or different 1 or 2 substituents at a substitutable position, or when one carbon atom has two branched chains, they may be taken together with the carbon atom to form divalent cycloalkyl;

$A^{32}$ represents a single bond, an oxygen atom, a sulfur atom, or —N($R^{32}$)— (wherein $R^{32}$ represents a hydrogen atom or alkyl);

$R^3$ represents an optionally substituted non-cyclic aliphatic hydrocarbon group having 1 to 8 carbon atoms, an optionally substituted cyclic aliphatic hydrocarbon group having 3 to 10 carbon atoms which is mono- to tricyclic, an optionally substituted aromatic hydrocarbon group having 6 to 12 carbon atoms which is mono- or dicyclic, or an optionally substituted heterocyclic group which is mono- to tricyclic;

when E is —CON(R²)—, the —N(R²)— may be taken together with -A³-R³ to form a cyclic amino group; and R⁴ and R⁵ are the same or different and each represents a hydrogen atom, alkyl, alkoxy or halogen;

with the exception of N-{4-[((1S,2R)-2-{[amino(imino) methyl]amino}cyclohexyl)amino]-6-methoxyquinazolin-2-yl}-4-chlorobenzamide and N-{4-[((1S,2R)-2-{[amino (imino)methyl]amino}cyclohexyl)amino]-6-methyl quinazolin-2-yl}-4-chlorobenzamide and salts thereof, and (B) an antipruritic agent comprising the quinazoline derivative (1) or a salt thereof as an active ingredient.

The quinazoline derivative represented by the above formula (I) can be represented by the substituent at the 2-position of the quinazoline skeleton in the following general formulas (1a) and (1b):

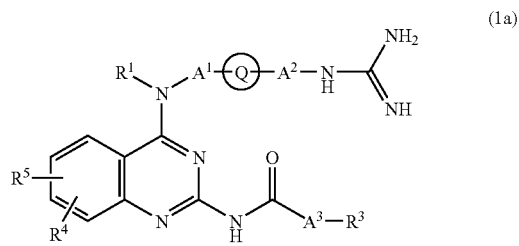

(1a)

wherein R¹, ring Q, A¹, A², A³, R³, R⁴ and R⁵ are as defined above,

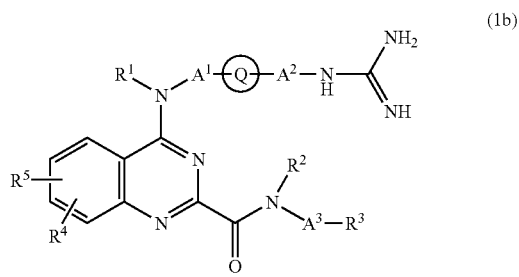

(1b)

wherein R¹, ring Q, A¹, A², A³, R², R³, R⁴ and R⁵ are as defined above.

The inventive compound is a novel compound, which has never been described in documents and has an excellent antipruritic effect.

The present invention will be described in detail hereinafter.

Terms used in the present invention and definitions of substituents are as follows.

Examples of "alkyl" may include a straight or branched alkyl having 1 to 8 carbon atoms, for example, methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, and isooctyl. Particularly, alkyl having 1 to 6 carbon atoms is preferable and alkyl having 1 to 4 carbon atoms is more preferable.

Examples of the alkyl moiety of "alkylthio", "alkoxy-alkyl", "dialkylamino", "monoalkylamino", "dialkylcarbamoyl", "monoalkylcarbamoyl", "aminoalkyl", "alkylsulfonyl", "alkylsulfonylamino", "arylalkyl",  "dialkylaminosulfonyl", "alkoxycarbonylalkyl" and "benzylthioalkyl" may include those listed above.

Examples of the "cyclohexylene group" may include 1,2-cyclohexylene, 1,3-cyclohexylene and 1,4-cyclohexylene. Particularly, 1,2-cyclohexylene is preferable.

Examples of the "phenylene group" may include 1,2-phenylene, 1,3-phenylene and 1,4-phenylene.

Examples of the "alkylene group" may include a straight or branched alkylene group having 1 to 6 carbon atoms, for example, methylene, ethylene, trimethylene, tetramethylene, pentamethylene and hexamethylene. Particularly, a straight or branched alkylene group having 1 to 5 carbon atoms is preferable and a straight or branched alkylene group having 1 to 4 carbon atoms is more preferable.

Examples of the "divalent saturated or unsaturated aliphatic hydrocarbon group" may include straight or branched alkylene having 1 to 6 carbon atoms and straight or branched alkenylene having 2 to 6 carbon atoms. It may have the same or different 1 or 2 substituents at a substitutable position. Examples of the substituent may include alkyl, alkoxy, phenyl, alkoxyalkyl, alkoxycarbonyl, dialkylamino and oxo.

Examples of "cycloalkyl" may include cyclic alkyl having 3 to 10 carbon atoms which is mono- to tricyclic, for example, cyclopropyl, cyclobutyl, cyclopentyl, cyclohexyl, cycloheptyl, cyclooctyl, cyclononyl, cyclodecanyl, adamanthyl (1-adamanthyl, 2-adamanthyl, etc.), 2-bicyclo[3.1.1]heptyl and 2-bicyclo[2.2.1]heptyl. The cycloalkyl may have the same or different 1 or 2 substituents and examples of the substituent may include alkyl, alkoxycarbonyl, carbamoyl, monoalkylcarbamoyl, dialkylcarbamoyl and alkoxy. Particularly, cycloalkyl having 4 to 9 carbon atoms is preferable and cycloalkyl having 5 to 8 carbon atoms is more preferable.

Examples of the "optionally substituted non-cyclic aliphatic hydrocarbon group having 1 to 8 carbon atoms" may include straight or branched alkyl having 1 to 8 carbon atoms, straight or branched alkenyl having 2 to 8 carbon atoms and straight or branched alkynyl having 2 to 8 carbon atoms. It may have the same or different 1 to 3 substituents at a substitutable position. Examples of the substituent include alkyl, hydroxy, alkoxy, phenyl (such phenyl may be substituted with alkoxy, halogen, or hydroxy), phenoxy, alkylthio, carboxy, alkoxycarbonyl, acyl, amino, monoalkylamino, dialkylamino, acylamino, alkylsulfonyl, alkylsulfonylamino, phenylsulfonyl, oxo, cyano, trifluoromethyl, benzoyl, benzyloxycarbonyl, benzylthio and imidazol-4-yl.

Examples of the "optionally substituted cyclic aliphatic hydrocarbon group having 3 to 10 carbon atoms which is mono- to tricyclic" may include a cyclic aliphatic hydrocarbon group which may have 1 to 3 unsaturated bonds and may be fused with 1 or 2 benzene rings, for example, cycloalkyl, cycloalkenyl, indanyl (1-indanyl, 2-indanyl, 5-indanyl, etc.), 3-oxoindan-1-yl, indenyl (2-indenyl, 5-indenyl, etc.), 2,3-dihydro-1H-indenyl (2,3-dihydro-1H-inden-1-yl, 2,3-dihydro-1H-inden-2-yl, 2,3-dihydro-1H-inden-5-yl, etc.), 1,2,3,4-tetrahydronaphthalen-1-yl, 2-fluorenyl, 9-oxo-9H-fluoren-2-yl and 7-bicyclo[4.2.0]octane-1,3,5-trienyl. The cyclic aliphatic hydrocarbon group may have the same or different 1 to 3 substituents at a substitutable position. Examples of the substituent may include alkyl, alkynyl, alkoxy, alkoxycarbonyl, carbamoyl, aryl, alkoxyalkyl, acyl and oxo.

Examples of the "optionally substituted aromatic hydrocarbon group having 6 to 12 carbon atoms which is mono- or dicyclic" may include an aryl group having 6 to 12 carbon atoms. The aromatic hydrocarbon group may have the same or different 1 to 3 substituents and examples of the substituent include alkyl, arylalkyl, arylalkenyl, alkenyl, cinnamyl, alkoxy, phenyl, phenoxy, acyl, acylamino, alkoxycarbonyl, amino, aminoalkyl, monoalkylamino, dialkylamino, dialkylaminosulfonyl, alkylsulfonyl, alkylsulfonylamino, phenylsulfonyl, oxo, cyano, nitro, aminosulfonyl, halogen, trifluoromethyl, trifluoromethoxy, alkylthio, 1H-pyrrol-1-yl, 5-oxo-4,5-dihydro-1H-pyrazol-1-yl and aminosulfonyl. Alternatively, it may be combined with the adjacent substituent to form a methylenedioxy group.

Examples of the "optionally substituted heterocyclic group which is mono- to tricyclic" may include a 5- to 12-membered monocyclic or fused ring which may have 1 to 3 hetero atoms selected from the group consisting of nitrogen, oxygen and sulfur atoms and 1 to 6 unsaturated bonds. Specific examples thereof may include pyridyl (2-pyridyl, 3-pyridyl, 4-pyridyl), pyrimidinyl (2-pyrimidinyl, 4-pyrimidinyl, 5-pyrimidinyl), pyrazinyl (2-pyrazinyl, etc.), pyridazinyl (3-pyridazinyl, 4-pyridazinyl), pyrrolyl (2-pyrrolyl, etc.), furanyl (2-furanyl, 3-furanyl), tetrahydrofuranyl (2-tetrahydrofuranyl, 3-tetrahydrofuranyl), 5-oxotetrahydrofuran-3-yl, 2-oxotetrahydrofuran-3-yl, thienyl (2-thienyl, 3-thienyl), imidazolyl (1-imidazolyl, 4-imidazolyl, etc.), pyrazolyl (3-pyrazolyl, 5-pyrazolyl, etc.), oxazolyl (4-oxazolyl, 5-oxazolyl, etc), thiazolyl (1,3-thiazol-2-yl, 1,3-thiazol-5-yl, etc.), isoxazolyl (isoxazol-4-yl, isoxazol-5-yl, etc.), 1,3,4-thiadiazol-2-yl, benzo[b]thienyl(benzo[b]thiophen-2-yl, benzo[b]thiophen-3-yl, etc.), benzo[b]furanyl (2-benzo[b]furanyl, etc.), 2,3 -dihydrobenzo[b]furan-7-yl, 2-benzoimidazolyl, 2-oxo-2,3-dihydro-1H-benzimidazol-5-yl, benzothiazolyl (1,3-benzothiazol-2-yl, etc.), indolyl (2-indolyl, 3-indolyl, etc.), 1,3-dioxo-1,3-dihydro-2H-isoindol-2-yl, quinolyl (2-quinolyl, 3-quinolyl, 6-quinolyl, etc.), 3-isoquinolyl, 2H-chromen-6-yl, 2-oxo-2H-chromen-6-yl, 2-oxo-2H-chromen-7-yl, 6-oxo-7,8-dihydro-6H-[1,3]dioxolo[4,5-g] chromen-8-yl, 2,3-dihydro-1,4-benzodioxyn-6-yl, 3,4-dihydro-2H-1,4-benzooxazin-6-yl, 3-oxo-3,4-dihydro-2H-1,4-benzooxazin-6-yl, pyrrolidinyl (1-pyrrolidinyl, 2-pyrrolidinyl, 2S-pyrrolidinyl, 3-pyrrolidinyl, etc.), 1-pyrrolinyl, 1-dihydrothiazolyl, 3,4-dihydropyridin-1-yl, 4-piperidinyl, 1,2,5,6-tetrahydropyridin-1-yl, piperazin-1-yl, homopiperazin-1-yl, morpholino, thiomorpholino, 1-indolinyl, 3,4-dihydroisoquinolin-2-yl, octahydroquinolin-1-yl, 1-azabicyclo[2.2.2]oct-3-yl, 6-azabicyclo[3.2.1]oct-6-yl, 2-oxo-2,3-dihydro-1,3-benzoxazol-5-yl, or a cyclic amino group listed hereinafter. The heterocyclic ring may have the same or different 1 to 3 substituents and examples of the substituent include alkyl, alkylthio, alkoxy, alkoxycarbonylalkyl, acyl, nitro, phenyl which is substituted with nitro, arylalkyl, 2-pyridyl and halogen.

Examples of the "cyclic amino group," may include a cyclic amino group which is mono- to tricyclic and may have at least one nitrogen atom and also may have 1 or 2 hetero atoms selected from nitrogen, oxygen and sulfur atoms and 1 to 3 unsaturated bonds. Specific examples thereof include pyrrolidin-1-yl, 1-pyrrolinyl, 1,3-thiazolidin-3-yl, piperidino, dihydropyridin-1-yl, 1,2,3,6-tetrahydropyridin-1-yl, piperazin-1-yl, homopiperazin-1-yl, morpholino, thiomorpholino, 2,3-dihydro-1H-indol-1-yl, 1,2,3,4-tetrahydroquinolin-1-yl, 1,2,3,4-tetrahydroisoquinolin-2-yl, octahydroquinolin-1-yl, 8-(4-oxo-1,3,8-triazaspiro[4,5]decyl), 2,5-dihydro-1H-pyrrol-1-yl and 6-azabicyclo[3.2.1]oct-6-yl. The cyclic amino may have the same or different 1 to 3 substituents and examples of the substituent include alkyl, alkoxy, alkoxyalkyl, acyl, acylamino, alkoxycarbonyl, carbamoyl, monoalkylcarbamoyl, dialkylcarbamoyl, aryl which may be substituted with alkoxy, arylalkyl, arylalkenyl, piperidino, pyridyl(pyridin-2-yl, pyridin-4-yl, etc.), pyrimidinyl(pyrimidin-2-yl, etc.), pyrazinyl(pyrazin-2-yl, etc.) and 1,3-benzodioxol-5-ylmethyl.

Examples of "alkoxy" may include straight or branched alkoxy having 1 to 8 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy, isohexyloxy, n-heptyloxy, isoheptyloxy, n-octyloxy and isooctyloxy. Particularly, straight or branched alkoxy having 1 to 6 carbon atoms is preferable and straight or branched alkoxy having 1 to 4 carbon atoms is more preferable.

Examples of the alkoxy moiety of "alkoxycarbonyl", "alkoxyalkyl" and "alkoxycarbonylalkyl" may include those listed above.

Examples of "halogen" may include fluorine, chlorine, bromine and iodine atoms.

Examples of "acyl" may include straight or branched alkanoyl having 1 to 8 carbon atoms, for example, formyl, acetyl, propanoyl, butyryl, valeryl, hexanoyl, heptanoyl and octanoyl. Particularly, straight or branched alkanoyl having 1 to 6 carbon atoms is preferable and straight or branched alkanoyl having 1 to 4 carbon atoms is more preferable.

Examples of the acyl moiety of "acylamino" may include those listed above.

Examples of "aryl" may include acyl having 6 to 12 carbon atoms, for example, phenyl, 1-naphthyl, 2-naphthyl and biphenyl.

Examples of the aryl moiety of "arylalkyl" may include those listed above.

Examples of "alkenyl" may include straight or branched alkenyl having 2 to 8 carbon atoms, for example, vinyl, propenyl, butenyl, pentenyl, hexenyl, heptenyl and octenyl. Particularly, straight or branched alkenyl having 2 to 6 carbon atoms is preferable and straight or branched alkenyl having 2 to 4 carbon atoms is more preferable.

Examples of the alkenyl moiety of "arylalkenyl" may include those listed above.

Examples of "alkynyl" may include straight or branched alkynyl having 2 to 8 carbon atoms, for example, ethynyl, propynyl, butynyl, pentynyl, hexynyl, heptynyl and octynyl. Particularly, straight or branched alkynyl having 2 to 6 carbon atoms is preferable and straight or branched alkynyl having 2 to 4 carbon atoms is more preferable.

Examples of "cycloalkenyl" may include cyclic alkenyl having 3 to 10 carbon atoms and 1 to 3 double bonds which is mono- to tricyclic, for example, cyclopropenyl, cyclobutenyl, cyclopentenyl, cyclohexenyl (1-cyclohexen-1-yl, 3-cyclohexen-1-yl, etc.), cycloheptenyl, cyclooctenyl, cyclononenyl, cyclodecenyl and bicyclo[2.2.1]hept-2-en-5-yl. The cycloalkenyl may have the same or different 1 or 2 substituents and examples of the substituent include alkyl, alkoxycarbonyl, carbamoyl, monoalkylcarbamoyl, dialkylcarbamoyl and alkoxy. Particularly, cyclic alkenyl having 4 to 9 carbon atoms is preferable and cyclic alkenyl having 5 to 8 carbon atoms is more preferable.

Examples of the "alkenylene group" may include a straight or branched alkenylene group, which have 2 to 6 carbon atoms and 1 to 3 double bonds, for example, vinylene, propenylene, butenylene, pentenylene and hexenylene. Particularly, straight or branched alkenylene group having 2 to 5 carbon atoms is preferable and straight or branched alkenylene group having 2 to 4 carbon atoms is more preferable.

Examples of "salt" include pharmaceutically acceptable salts, for example, salts of inorganic acids such as hydrochloric acid, sulfuric acid, nitric acid, phosphoric acid, hydrofluoric acid and hydrobromic acid, or salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid and camphorsulfonic acid.

The term "antipruritic agent" as used herein refers to a drug for the suppression of itching For example, it refers to a drug for the suppression of itching due to atopic dermatitis, urticaria, psoriasis, xeroderma, trichophytia, vitiligo vulgaris, local pruritus cutaneous caused by insect excretion and secretion, nodular prurigo, kidney dialysis, diabetes, blood disease, liver disease, kidney disease, incretion and metabolic disorder, viscera malignant tumor, hyperthyroidism, autoimmune disease, multiple sclerosis, neurologic disease, psychoneurosis, allergic conjunctivitis, spring catarrh, atopic keratoconjunctivitis, or itching caused by excess use of laxuries and drugs.

A preferred inventive compound is aforementioned quinazoline derivative (1) wherein $R^1$ is a hydrogen atom, one of $R^4$ and $R^5$ is a hydrogen atom and the other one is alkyl, the ring Q is a cyclohexylene group, $A^1$ and $A^2$ represent a single bond, $R^3$ is an optionally substituted alkyl group, an optionally substituted cycloalkyl group, an optionally substituted aryl group or an optionally substituted heterocyclic group, or a salt thereof. Particularly, a quinazoline derivative (1) wherein $R^3$ is an alkyl group, a cycloalkyl group, a phenyl group which may be substituted with alkoxy, a benzo[b]thienyl group or a benzo[b]furanyl group, or a salt thereof is preferable.

Particularly preferred inventive compounds may include N-{4-[((1S,2R)-2-{[amino(imino)methyl]amino}cyclohexyl)amino]-6-methylquinazolin-2-yl}-1-benzothiophene-2-carboxamide, N-{4-[((1S,2R)-2-{[amino(imino)methyl]amino}cyclohexyl)amino]-6-methylquinazolin-2-yl}-4-methoxybenzamide, N-{4-[((1S,2R)-2-{[amino(imino)methyl]amino}cyclohexyl)amino]-6-methylquinazolin-2-yl}-1-benzofuran-2-carboxamide, 4-[((1S,2R)-2-{[amino(imino)methyl]amino}cyclohexyl)amino]-6-methyl-N-neopentylquinazoline-2-carboxamide, 4-[((1S,2R)-2-{[amino(imino)methyl]amino}cyclohexyl)amino]-N-(3,3-dimethylbutyl)-6-methylquinazoline-2-carboxamide, 4-[((1S,2R)-2-{[amino(imino)methyl]amino}cyclohexyl)amino]-N-cycloheptyl-6-methylquinazoline-2-carboxamide, 4-[((1S,2R)-2-{[amino(imino)methyl]amino}cyclohexyl)amino]-N-(2-ethylbutyl)-6-methylquinazoline-2-carboxamide, 4-[((1S,2R)-2-{[amino(imino)methyl]amino}cyclohexyl)amino]-6-methyl-N-n-propylquinazoline-2-carboxamide, and 4-[((1S,2R)-2-{[amino(imino)methyl]amino}cyclohexyl)amino]-N-isobutyl-6-methylquinazoline-2-carboxamide, and salts thereof.

The inventive compound of aforementioned general formula (Ia) can be prepared by the following reaction scheme in accordance with the method described in International Publication WO01/72710:

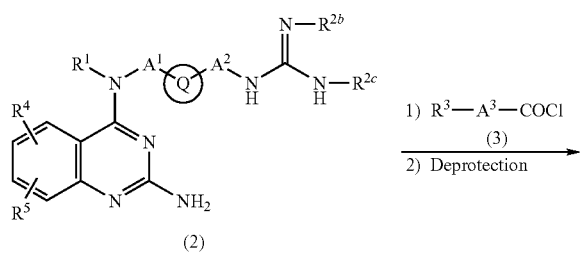

(2)

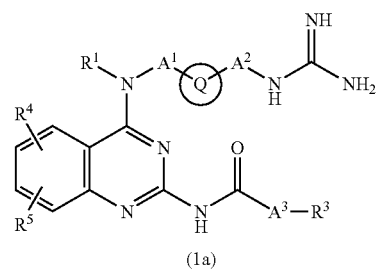

(1a)

wherein $R^1$, $R^3$, $R^4$, $R^5$, $A^1$, $A^2$, $A^3$ and ring Q are as defined above, and $R^{2b}$, $R^{2c}$ are the same or different and represent a protective group.

An inventive compound (1a) can be obtained by reacting a raw compound (2) with one equivalent to an excess amount of acid chloride (3) in a solvent, for example, a hydrocarbon solvent such as benzene or toluene, an ether solvent such as dioxane or tetrahydrofuran or a halogenated solvent such as methylene chloride, 1,2-dichloroethane or chloroform in the presence of a base such as triethylamine, N,N-diisopropylethylamine and pyridine and, if necessary, catalysts such as 4-dimethylaminopyridine at a temperature from room temperature to the boiling point of the employed solvent for several hours to several days, followed by deprotection using a per se known method. Examples of the protective group may include tert-butoxycarbonyl, benzyloxycarbonyl, benzyl and acetyl.

The raw compound (2) can be prepared in accordance with the method described in International Publication WO01/72710.

The raw compound (3) is commercially available or can be prepared by a per se known method.

The inventive compound of aforementioned general formula (Ib) can be prepared by the following reaction scheme:

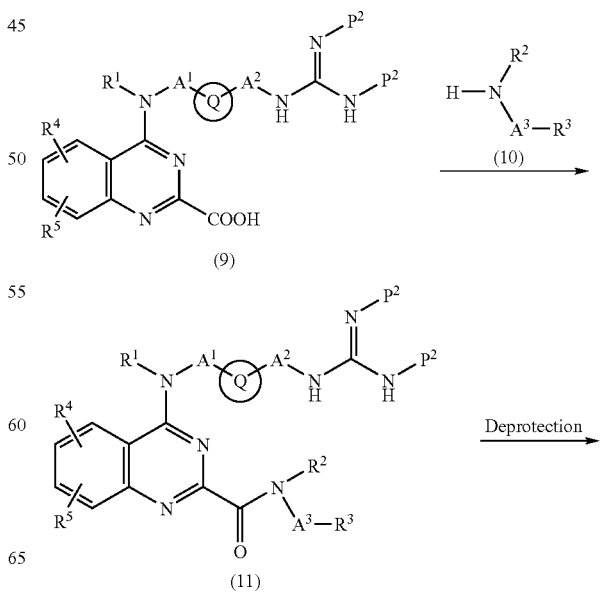

-continued

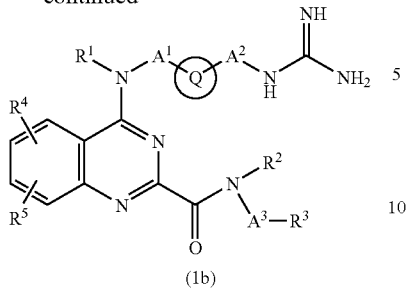

(1b)

wherein $R^1$, $R^2$, $R^3$, $R^4$, $R^5$, $A^1$, $A^2$, $A^3$ and ring Q are as defined above, and $P^2$ represents a protective group.

A compound (11) can be obtained by reacting a raw compound (9) with one equivalent to an excess amount of amine (10) in a solvent, for example, a hydrocarbon solvent such as benzene or toluene, an ether solvent such as dioxane or tetrahydrofuran, a halogenated solvent such as methylene chloride or 1,2-dichloroethane, or N,N-dimethylformamide in the presence of a base such as triethylamine, N,N-diisopropylethylamine or pyridine and a condensing agent such as N,N'-dicyclohexylcarbodiimide, 1-(3-dimethylaminopropyl)-3-ethylcarbodiimide or 1,1'-carbonylbis-1H-imidazole at a temperature from 0° C. to the boiling point of the employed solvent for several hours to several days. Examples of the protective group may include tert-butoxycarbonyl, benzyloxycarbonyl, benzyl and acetyl. Preferably, using N,N-dimethylformamide as a solvent, 1-(3-dimethylaminopropyl)-3-ethylcarbodiimide is added and the reaction is effected at room temperature for 24 to 48 hours in the presence of triethylamine. The amine (10) is commercially available or can be prepared by a per se known method. The inventive compound (1b) can be prepared by deprotecting the compound (11) using a per se known method.

When $P^2$ is t-butoxycarbonyl, it is particularly preferred to react with hydrochloric acid in ethyl acetate-methanol at a temperature from room temperature to 50° C. for 1 to 48 hours. When $P^2$ is benzyloxycarbonyl, it is preferred to hydrogenate in methanol in the presence of 5% palladium-carbon at room temperature under normal pressure.

A raw compound (9) can be prepared by the following reaction scheme:

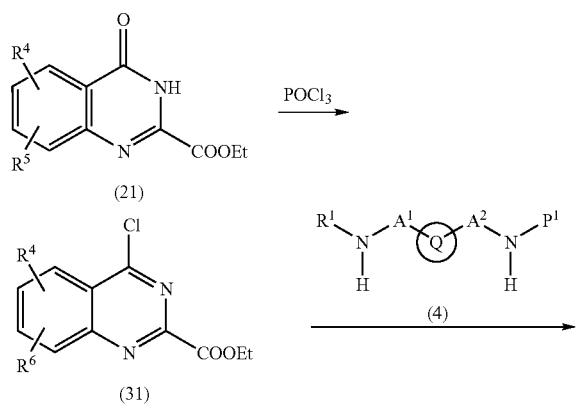

-continued

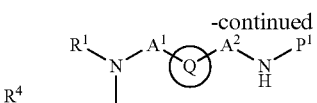

(5)

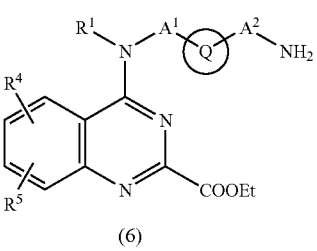 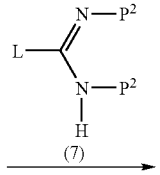

(6)                                   (7)

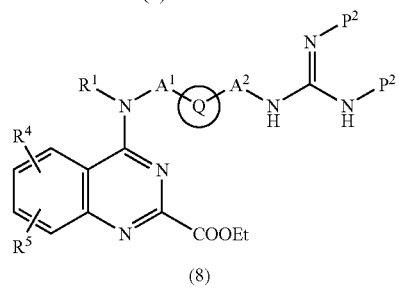

(8)

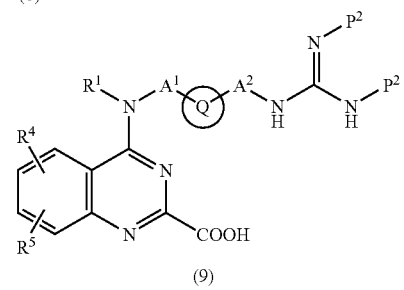

(9)

wherein $R^1$, $R^4$, $R^5$, $A^1$, $A^2$, ring Q and $P^2$ are as defined above, L represents a leaving group, and $P^1$ represents a protective group.

A compound (31) can be obtained by reacting a raw compound (21) [which can be prepared by a known method (see Journal of Organic Chemistry 27, 4672 (1962))] with a chlorination agent such as phosphorus oxychloride or phosphorus pentachloride in the presence or absence of a solvent such as toluene, xylene or 1,2-dichloroethane at a temperature from room temperature to the boiling point of the employed solvent (from room temperature to the boiling point of the employed chlorination agent in case of using no solvent) for 1 to 24 hours. If necessary, a tertiary amine such as N,N-dimethylaniline or triethylamine may coexist.

A compound (5) can be obtained by reacting a compound (31) with one equivalent to an excess amount of amine (4) in an organic solvent, for example, a hydrocarbon solvent such as benzene or toluene, an ether solvent such as dioxane or tetrahydrofuran, an alcohol solvent such as ethanol or isopropanol, or N,N-dimethylformamide in the presence of an optional base such as triethylamine or N,N-diisopropylethylamine at a temperature from room temperature to the boiling point of the employed solvent for several hours to several days. It is particularly preferred to react a compound (31) with 1 to 2 equivalents of amine (4) in a toluene solvent in the presence of triethylamine at 100 to 130° C. for 24 to 48 hours. The amine (4) is commercially available or can be prepared by a per se known method. Examples of the protective group $P^1$ may include tert-butoxycarbonyl, benzyloxycarbonyl, benzyl and acetyl.

A compound (6) can be prepared by deprotecting a compound (5) by a per se known method. When $P^1$ is t-butoxycarbonyl, it is preferred to react with trifluoroacetic acid in methylene chloride at room temperature for 1 to 5 hours. When $P^1$ is benzyloxycarbonyl, it is preferred to hydrogenate in methanol in the presence of 5% palladium-carbon at room temperature under normal pressure.

A compound (8) can be obtained by reacting a compound (6) with 1 to excess amount of a compound (7) in a solvent, for example, a hydrocarbon solvent such as benzene or toluene, an ether solvent such as dioxane or tetrahydrofuran, a halogenated solvent such as chloroform or 1,2-dichloroethane, or N,N-dimethylformamide at a temperature from 0° C. to the boiling point of the employed solvent for several hours to several days. Examples of the leaving group L may include pyrazol-1-yl, methylthio, methoxy and halogen.

It is particularly preferred to react at room temperature for 1 to 48 hours using pyrazol-1-yl as the leaving group L of a compound (7), t-butoxycarbonyl as the protective group $P^2$ and dichloromethane as the solvent.

A compound (9) can be obtained by hydrolyzing a compound (8) using a per se known method. It is particularly preferred to react the compound (8) in tetrahydrofuran in the presence of 1N-sodium hydroxide at a temperature from room temperature to 60° C. for 1 to 3 hours.

The compound of aforementioned general formula (1b) can be prepared by the following reaction scheme:

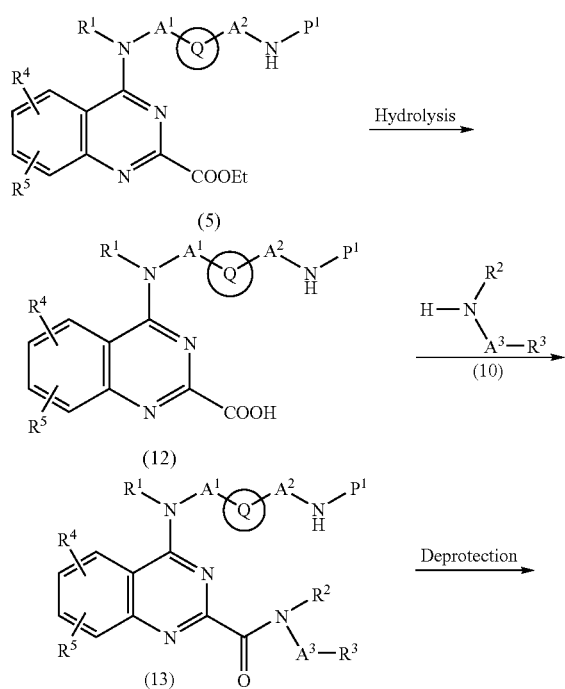

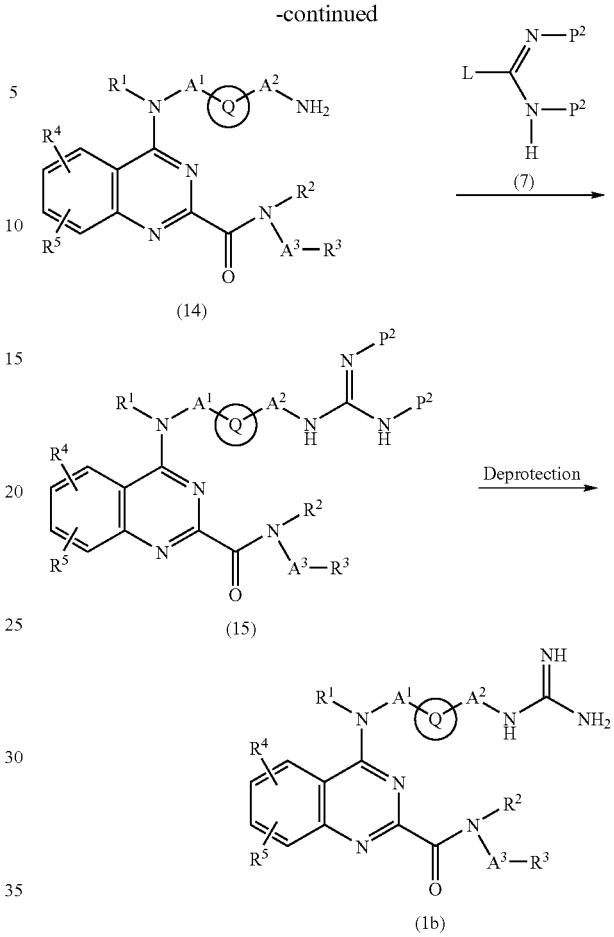

wherein $R^1$, $R^2$, $R^3$, $R^4$, $R^5$, $A^1$, $A^2$, $A^3$, L, ring Q, $P^1$ and $P^2$ are as defined above.

A compound (12) is obtained by hydrolyzing a raw compound (5) by a per se known method. It is particularly preferred to react the raw compound (5) in tetrahydrofuran in the presence of 1N-sodium hydroxide at a temperature from room temperature to 60° C. for 1 to 3 hours.

A compound (13) is obtained by reacting a compound (12) with one equivalent to an excess amount of amine (10) in a solvent, for example, a hydrocarbon solvent such as benzene or toluene, an ether solvent such as dioxane or tetrahydrofuran, a halogenated solvent such as methylene chloride or 1,2-dichloroethane, or N,N-dimethylformamide in the presence of a base such as triethylamine, N,N-diisopropylethylamine or pyridine and a condensing agent such as N,N'-dicyclohexylcarbodiimide, 1-(3-dimethylaminopropyl)-3-ethylcarbodiimide or 1,1'-carbonylbis-1H-imidazole at a temperature from room temperature to the boiling point of the employed solvent for several hours to several days. Preferably, using N,N-dimethylformamide as a solvent, 1-(3-dimethylaminopropyl)-3-ethylcarbodiimide is added and the reaction is effected at room temperature for 24 to 48 hours in the presence of triethylamine. The amine (10) is commercially available or can be prepared by a per se known method.

A compound (14) can be prepared by deprotecting the compound (13) using a per se known method. When $P^1$ is t-butoxycarbonyl, the compound (13) is preferably allowed to react with trifluoroacetic acid in methylene chloride at room temperature for 1 to 5 hours. When $P^1$ is benzyloxycarbonyl, the compound (13) is preferably hydrogenated in methanol in the presence of 5% palladium-carbon at room temperature under normal pressure.

An inventive compound (1b) can be obtained by reacting a compound (14) with one equivalent to an excess amount of a compound (7) in a solvent, for example, a hydrocarbon solvent such as benzene or toluene, an ether solvent such as dioxane or tetrahydrofuran, a halogenated solvent such as chloroform or 1,2-dichloroethane, or N,N-dimethylformamide at a temperature from 0° C. to the boiling point of the employed solvent for several hours to several days, followed by deprotecting using a per se known method. It is particularly preferred to react them at room temperature for 1 to 48 hours using pyrazol-1-yl as the leaving group L of the compound (7), t-butoxycarbonyl as the protective group and dichloromethane as the solvent, followed by deprotecting with hydrochloric acid.

Salts of the inventive compound can be prepared by a per se known method. For example, hydrochlorides of the inventive compound can be obtained by treating the inventive compound with an alcohol or ethyl ether solution of hydrogen chloride and filtering to collect the deposited crystals by filtration. When no crystals are deposited, the solution is concentrated to deposit crystals and then the deposited crystals are collected by filtration.

The inventive compound thus produced and salts thereof can be isolated and purified by a method known per se, such as concentration, liquid phase conversion, partition, solvent extraction, crystallization, recrystallization, fractional distillation or chromatography.

Some of the inventive compounds may have asymmetric carbon atoms, and each optical isomer and a racemate thereof are also included in the present invention. An optical isomer can be produced, for example, by starting from a racemate obtained as described above utilizing the basic property thereof using an optically active acid (tartaric acid, dibenzoyltartaric acid, mandelic acid, 10-camphorsulfonic acid and the like) by a known method to effect an optical resolution, or by starting from a previously prepared optically active compound.

The inventive compounds may exist as a cis (Z form) isomer or a trans (E form) isomer, and each isomer and a mixture thereof are also included in the present invention.

The inventive compounds are useful as an antipruritic agent because they exert a scratching behavior suppressing effect as shown in the Test Examples described hereinafter.

When the inventive compounds are administered as a medicament, they can be administered to a mammal including human as they are or in a mixture with a pharmaceutically acceptable non-toxic inert carrier, for example, as a pharmaceutical composition containing the compound at a level of 0.001% to 99.5%, preferably 0.1% to 90%.

As a carrier, one or more of auxiliary agents for a formulation such as solid, semi-solid and liquid diluent, filler and other auxiliary agents for a drug formulation may be used. It is desirable that a pharmaceutical composition of the present invention is administered as a unit dosage form. The pharmaceutical composition can be administered into tissue, or orally, intravenously, topically (percutaneously, instillation) or rectally. It is a matter of course that a dosage form suitable for any of the administration modes described above is employed. For example, oral, intravenous or local administration (percutaneous administration, instillation) is preferable.

While it is desirable that the dose as an antipruritic agent may be adjusted depending on the conditions of the patients including the age, body weight, nature and degree of the disease as well as the administration route, a daily dose as an active ingredient of the inventive compound in an adult is usually 0.1 mg to 5 g per adult, preferably 1 mg to 500 mg per adult when given orally, and usually 0.1 mg to 500 mg per adult, preferably 1 mg to 50 mg per adult when given intravenously. The level of the active ingredient is usually 0.001% to 5%, preferably 0.01% to 0.1% when given rectally, and usually 0.0001% to 0.5%, preferably 0.001% to 0.01% in case of instillation. In some cases, a lower dose may be sufficient or a higher dose may be required. Usually, the dose is given once or several times as being divided into portions, or given intravenously and continuously over a period of 1 to 24 hours a day.

Oral administration can be accomplished in a solid or liquid dosage form, such as a particle, powder, tablet, sugar-coated tablet, capsule, granule, suspension, liquid, syrup, drop, buccal formulation, suppository or other dosage forms. A particle is produced by pulverizing an active ingredient into a suitable particle size. A powder can be produced by pulverizing an active ingredient into a suitable particle size followed by mixing with a pharmaceutical carrier, such as an edible carbohydrate including starches or mannitol, which has also been pulverized into a suitable particle size. Those, which may be added if necessary, are flavors, preservatives, dispersing agents, colorants, fragrances and the like.

A capsule may be produced by filling a particle or powder which has previously been pulverized as described above or a granule obtained as described in the section of a tablet for example in a capsule such as a gelatin capsule. It is also possible that an additive such as a lubricant, fluidizing agent, such as colloidal silica, talc, magnesium stearate, calcium stearate or solid polyethylene glycol is mixed with the pulverized material prior to the filling procedure. For the purpose of enhancing the availability of a medicament when a capsule is ingested, a disintegrant or solubilizing agent, such as carboxymethyl cellulose, calcium carboxymethyl cellulose, low substituted hydroxypropyl cellulose, sodium croscarmellose, sodium carboxy starch, calcium carbonate or sodium carbonate, may be added.

The finely pulverized powder of the inventive compound may be suspended and dispersed in a vegetable oil, polyethylene glycol, glycerin and surfactant, and then encapsulated in a gelatin sheet, thereby obtaining a soft capsule. A tablet is produced by formulating a powder mix, converting into a granule or slug, adding a disintegrant or lubricant and then compacting into a tablet. The powder mix is obtained by mixing an appropriately pulverized material with a diluent or base described above if necessary together with a binder (for example, sodium carboxymethyl cellulose, hydroxypropyl cellulose, methyl cellulose, hydroxypropylmethyl cellulose, gelatin, polyvinyl pyrrolidone, polyvinyl alcohol and the like), a dissolution retardant (for example, paraffin, wax, hardened castor oil and the like), a resorption promoter (for example, quaternary salt), or an adsorbent (for example, bentonite, kaolin, calcium diphosphate and the like). The powder mix can be wetted with a binder such as a syrup, starch glue, gum arabic, cellulose solution or polymer solution and then forcibly passed through a sieve to thereby obtain granules. Instead of the procedure for granulating a powder as described above, the powder mix can be subjected first to a tablet compacting machine, and the resulting morphologically incomplete slug is then ground to thereby obtain granules. The granules thus obtained may contain, as a lubricant, stearic acid, stearates, talc, mineral oil and the like, for the purpose of preventing any adhesion with each other. The mixture thus lubricated is then compacted into tablets. A plane tablet thus obtained may be film-coated or sugar-coated.

The inventive compound may be mixed with a fluidized inert carrier and then compacted directly into tablets without being subjected to the granulating or slugging process described above. A transparent or semitransparent protective film in the form of a shellac sealing film, a film of a sugar or polymeric material and a glossy film of a wax may also be employed.

Other oral dosage forms, such as a solution, syrup and elixir can be formulated as a unit dosage form whose certain amount contains a certain amount of a medicament. Syrup is produced by dissolving the inventive compound in a flavored aqueous solution, while an elixir is produced by using a non-toxic alcoholic carrier. A suspension is formulated by dispersing the inventive compound in a non-toxic carrier. Additives such as a solubilizing agent, an emulsifier (for example ethoxylated isostearyl alcohols, polyoxyethylene sorbitol esters), a preservative and a flavor (for example, peppermint oil, saccharin) may also be added if necessary.

An oral unit dosage formulation may also be a microcapsule if desired. Such a formulation may be coated or embedded in a polymer or wax to obtain a prolonged activity or sustained release of the active ingredient.

A rectal administration can be accomplished by using a suppository obtained by mixing the inventive compound with a water-soluble or water-insoluble solid having a low melting point such as a polyethylene glycol, cocoa butter, higher esters (for example, myristyl palmitate) as well as a mixture thereof.

The administration into a tissue can be accomplished by using a liquid unit dosage form, for example in the form of a solution or suspension, of a subcutaneous, intramuscular, bladder or intravenous injection formulation. Any of these formulations can be produced by suspending or dissolving a certain amount of the inventive compound in a non-toxic liquid carrier such as an aqueous or oily medium compatible with the purpose of the injection, followed by sterilizing said suspension or solution. Alternatively, a certain amount of the inventive compound is placed in a vial, which is then sterilized together with its content and then sealed. For reconstitution or mixing just before use, a powdery or freeze-dried active ingredient is provided with a complementary vial or carrier. It is also possible to add a non-toxic salt or salt solution for the purpose of making an injection solution isotonic. It is also possible to use a stabilizer, preservative, emulsifier and the like.

Instillation can be accomplished by using a liquid unit dosage form, for example in the form of a solution or suspension. Any of these formulations can be produced by suspending or dissolving a certain amount of the inventive compound in a non-toxic liquid carrier such as an aqueous or oily medium compatible with the purpose of the instillation, followed by sterilizing said suspension or solution. Alternatively, a certain amount of the inventive compound is placed in a vial, which is then sterilized together with its content and then sealed. For reconstitution or mixing just before use, a powdery or freeze-dried active ingredient is provided with a complementary vial or carrier. It is also possible to add a non-toxic salt or salt solution for the purpose of making an ophthalmic solution isotonic. It is also possible to use a stabilizer, preservative, emulsifier and the like.

In the antipruritic agent of the present invention, other ingredients, for example, an antihistaminic agent, antiallergic agent, steroid and the like, can be mixed or used in combination.

BEST MODE FOR CARRYING OUT THE INVENTION

The present invention will now be described in more detail with reference to Production Examples of the inventive compounds (Examples), Production Examples of typical starting materials (Reference Examples), Test Examples and Formulation Examples, but the present invention is not limited thereto. MS, NMR and elemental analysis confirmed the structure of the compounds of the Examples.

REFERENCE EXAMPLE 1

N-{(1R,2S)-2-[(2-amino-6-methylquinazolin-4-yl)amino]cyclohexyl}-N',N''''-bis(tert-butoxycarbonyl)guanidine Step 1

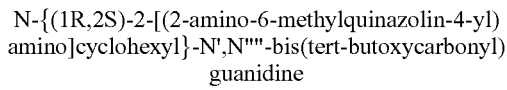
tert-butyl (1R,2S)-2-[(2-chloro-6-methylquinazolin-4-yl)amino]cyclohexylcarbamate To a solution of 4.80 g of 2,4-dichloro-6-methylquinazoline in 100 ml of methylene chloride, 9.12 g of triethylamine and 5.31 g of (1S,2R)-2-(t-butoxycarbonylamino)cyclohexylamine were added, and then the mixture was stirred at room temperature for 24 hours. The reaction solution was concentrated, mixed with water, extracted with methylene chloride and then dried. The solvent was distilled off and the residue was purified by silica gel column chromatography (chloroform:methanol=20:1) to obtain 8.30 g of the desirable compound.

Step 2

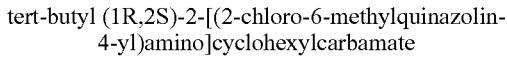
tert-butyl (1R,2S)-2-({2-[(4-methoxybenzyl)amino]-6-methylquinazolin-4-yl}amino)cyclohexylcarbamate To a solution of 4.00 g of tert-butyl (1R,2S)-2-[(2-chloro-6-methylquinazolin-4-yl)amino]cyclohexylcarbamate and 5.91 g of 4-methoxybenzylamine in 30 ml of N-methyl-2-pyrrolidone, 100 mg of 4-dimethylaminopyridine was added, and then the mixture was stirred at 110° C. for 24 hours. The reaction solvent was mixed with an aqueous 5% acetic acid solution and then extracted with ethyl acetate. The organic layer was washed with water and saturated brine, and then dried. The solvent was distilled off and the residue was purified by silica gel column chromatography (chloroform:methanol=20:1) to obtain 5.10 g of the desirable compound.

Step 3

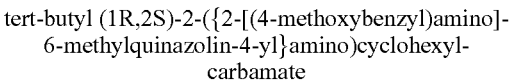
N⁴-[(1S,2R)-2-aminocyclohexyl]-6-methylquinazoline-2,4-diamine

To a solution of 9.37 g of tert-butyl (1R,2S)-2-({2-[(4-methoxybenzyl)amino]-6-methylquinazolin-4-yl}amino)cyclohexylcarbamate in 30 ml of methylene chloride, 95 ml of trifluoroacetic acid was added under ice cooling, and then the mixture was stirred for 72 hours. The reaction solution was concentrated, neutralized with a saturated sodium hydrogencarbonate solution, extracted with chloroform:methanol=10:1 and then dried. The solvent was distilled off and the residue was purified by Fuji Silysia NH silica gel column chromatography (chloroform:methanol=50:1) to obtain 4.60 g of the desirable compound.

Step 4

N-{(1R,2S)-2-[(2-amino-6-methylquinazolin-4-yl)amino]cyclohexyl}-N',N''-bis(tert-butoxycarbonyl)guanidine To a solution of 4.53 g of N⁴-[(1S,2R)-2-aminocyclohexyl]-6-methylquinazoline-2,4-diamine in 90 ml of methylene chloride, 5.18 g of N,N'-bis(t-butoxycarbonyl)-1H-pyrazole-1-carboxamidine was added, and then the mixture was stirred at room temperature for 15 hours. The reaction solution was mixed with water, extracted with methylene chloride and then dried. The solvent was distilled off and the residue was purified by silica gel column chromatography (chloroform:methanol=20:1) to obtain 8.50 g of the desirable compound.

REFERENCE EXAMPLE 2

4-{[(1S,2R)-2-({[(tert-butoxycarbonyl)amino][(tert-butoxycarbonyl)imino]methyl}amino)cyclohexyl]amino}-6-methylquinazoline-2-carboxylic acid Step 1

4-({(1S,2R)-2-[(tert-butoxycarbonyl)amino]cyclohexyl}amino)-6-methylquinazoline-2-carboxylic acid ethyl ester To a suspension of 8.47 g of 4-chloro-2-ethoxycarbonyl-6-methylquinazoline and 7.60 g of (1S,2R)-2-(t-butoxycarbonylamino)cyclohexylamine in 350 ml of toluene, 11.8 ml of triethylamine and a catalytic amount of 4-dimethylaminopyridine were added, and then the mixture was heated at reflux for 16 hours. After the reaction solution was mixed with a saturated sodium hydrogencarbonate solution and extracted with chloroform, the organic layer was washed with a 10% citric acid solution and saturated brine. After drying over magnesium sulfate, the solvent was distilled off to obtain 15.7 g of the desirable compound as a yellow powder.

Step 2

4-{[(1S,2R)-2-aminocyclohexyl]amino}-6-methylquinazoline-2-carboxylic acid ethyl ester dihydrochloride To a solution of 14.5 g of 4-({(1S,2R)-2-[(tert-butoxycarbonyl)amino]cyclohexyl}amino)-6-methylquinazoline-2-carboxylic acid ethyl ester in 600 ml of ethyl acetate, 68 ml of a 4N-hydrogen chloride-ethyl acetate solution was added under ice cooling, and then the mixture was stirred at room temperature for 11 hours. The deposited crystals were collected by filtration, washed with ethyl acetate and then dried to obtain 11.7 g of the desirable compound as a pink powder.

Step 3

4-{[(1S,2R)-2-({[(tert-butoxycarbonyl)amino][(tert-butoxycarbonyl)imino]methyl}amino)cyclohexyl]amino}-6-methylquinazoline-2-carboxylic acid ethyl ester To a suspension of 11.7 g of 4-{[(1S,2R)-2-aminocyclohexyl]amino}-6-methylquinazoline-2-carboxylic acid ethyl ester dihydrochloride in 400 ml of methylene chloride, 24.4 ml of triethylamine and 8.60 g of N,N'-bis(t-butoxycarbonyl)-1H-pyrazole-1-carboxyamidine were added, and then the mixture was stirred for 24 hours. The reaction solution was mixed with a saturated sodium hydrogencarbonate solution, extracted with chloroform and then dried over magnesium sulfate. After concentration, the residue was purified by silica gel column chromatography (n-hexane:ethyl acetate=2:1) to obtain 16.2 g of the desirable compound as a yellow powder.

Step 4

4-{[(1S,2R)-2-({[(tert-butoxycarbonyl)amino][(tert-butoxycarbonyl)imino]methyl}amino)cyclohexyl]amino}-6-methylquinazoline-2-carboxylic acid To a solution of 14.56 q of 4-{[(1S,2R)-2-({[(tert-butoxycarbonyl)amino][(tert-butoxycarbonyl)imino]methyl}amino)cyclohexyl]amino}-6-methylquinazoline-2-carboxylic acid ethyl ester in 350 ml of tetrahydrofuran, 55 ml of a 10% sodium hydroxide solution was added under ice cooling, and then the mixture was stirred at room temperature for 10 hours. The reaction solution was mixed with 170 ml of a 10% potassium hydrogensulfate solution, extracted with chloroform and then dried over magnesium sulfate. The solvent was distilled off to obtain 14.2 g of the desirable compound as a yellow powder.

EXAMPLE 1

N-{4-[((1S,2R)-2-{[amino(imino)methyl]amino}cyclohexyl)amino]-6-methylquinazolin-2-yl}-1-benzothiophene-2-carboxamide dihydrochloride Step 1

N-(4-{[(1S,2R)-2-({(tert-butoxycarbonyl)amino[(tert-butoxycarbonyl)imino]methyl}amino)cyclohexyl]amino}-6-methylquinazolin-2-yl)-1-benzothiophene-2-carboxamide dihydrochloride To a 604 mg of N,N-diisopropylethylamine in 4 ml of methylene chloride, 10 mg of 4-dimethylaminopyridine and 613 mg of benzo[b]thiophene-2-carbonylchloride were added, and the mixture was stirred for 60 minutes. To the mixture was added dropwise a solution of 800 mg of N-{(1R,2S)-2-[(2-amino-6-methylquinazolin-4-yl)amino]cyclohexyl}-N',N''-bis(tert-butoxycarbonyl)guanidine obtained in Reference Example 1 in 5 ml of methylene chloride, followed by stirring at room temperature for 15 hours. The reaction solution was mixed with water, extracted with methylene chloride and then dried. The solvent was distilled off and the residue was purified by silica gel column chromatography (chloroform:methanol=30:1) to obtain 890 mg of the desirable compound.

Step 2

N-{4-[((1S,2R)-2-{[amino(imino)methyl]amino}cyclohexyl)amino]-6-methylquinazolin-2-yl}-1-benzothiophene-2-carboxamide dihydrochloride To a solution of 890 mg of N-(4-{[(1S,2R)-2-({(tert-butoxycarbonyl)amino[(tert-butoxycarbonyl)imino]methyl}amino)cyclohexyl]amino}-6-methylquinazolin-2-yl)-1-benzothiophene-2-carboxamide dihydrochloride in 5 ml of methanol and 5 ml of chloroform, 10 ml of a 4N hydrogen chloride-ethyl acetate solution was added, and then the mixture was reacted at 50° C. for 24 hours. The reaction solution was concentrated and treated with methanol-ethyl ether to obtain 450 mg of the desirable compound.

Elemental analysis for $C_{25}H_{27}N_7OS.2HCl.1.2H_2O$ Calcd. (%): C, 52.85; H, 5.57; N, 17.26. Found (%): C, 52.90; H, 5.61; N, 16.97.

Positive ion FAB-MS m/z: 474[M+H]$^+$

Specific rotation $[\alpha]^{20}_D$=−110.91 (c=1.0 methanol)

EXAMPLE 2

4-[((1S,2R)-2-{[amino(imino)methyl]amino}cyclohexyl)amino]-N-(4-methoxyphenyl)-6-methylquinazoline-2-carboxamide dihydrochloride Step 1

4-{[(1S,2R)-2-({[(tert-butoxycarbonyl)amino[(tert-butoxycarbonyl)imino]methyl}amino)cyclohexyl]amino}-N-(4-methoxyphenyl)-6-methylquinazoline-2-carboxamide To a solution of 2.04 g of 4-{[(1S,2R)-2-({[(tert-butoxycarbonyl)amino][(tert-butoxycarbonyl)imino]methyl}amino)cyclohexyl]amino}-6-methylquinazoline-2-carboxylic acid, 694 mg of 4-methoxyaniline, 1.08 g of 1-(3-dimethylaminopropyl)-3-ethylcarbodiimide hydrochloride and 762 mg of 1-hydroxybenzotriazole in 40 ml of N,N'-dimethylformamide, 1.57 ml of triethylamine was added, and then the mixture was stirred at room temperature for 24 hours. The reaction solution was mixed with water and then extracted with ethyl acetate. The organic layer was washed with water and saturated brine and then dried over magnesium sulfate. The solvent was distilled off and the residue was purified by silica gel column chromatography (chloroform) to obtain 2.08 g of the desirable compound as a white powder.

Step 2

4-[((1S,2R)-2-{[amino(imino)methyl]amino}cyclohexyl)amino]-N-(4-methoxyphenyl)-6-methylquinazoline-2-carboxamide dihydrochloride To a solution of 2.07 g of 4-{[(1S,2R)-2-({(tert-butoxycarbonyl)amino[(tert-butoxycarbonyl)imino]methyl}amino)cyclohexyl]amino}-N-(4-methoxyphenyl)-6-methylquinazoline-2-carboxamide in 10 ml of methanol and 10 ml of chloroform, 40 ml of a 4N-hydrogen chloride-ethyl acetate solution was added, and then the mixture was reacted at 50° C. for 15 hours. The reaction solution was concentrated and recrystallized from methanol-diisopropyl ether to obtain 952 mg of the desirable compound as a yellow powder.

Positive ion FAB-MS m/z: 448[M+H]$^+$

In the same manner as in Example 1 or 2, the following compounds-were obtained.

EXAMPLE 3

N-{4-[((1S,2R)-2-{[amino(imino)methyl]amino}cyclohexyl)amino]-6-methylquinazolin-2-yl}-1-benzofuran-2-carboxamide dihydrochloride Elemental analysis for $C_{25}H_{27}N_7O_2.2HCl.2H_2O$ Calcd. (%): C, 53.01; H, 5.87; N, 17.31. Found (%): C, 53.34; H, 5.71; N, 17.25.

Positive ion FAB-MS m/z: 458[M+H]$^+$

Specific rotation $[\alpha]^{20}_D$=−114.82 (c=1.0 methanol)

EXAMPLE 4

N-{4-[(1S,2R)-2-{[amino(imino)methyl]amino}cyclohexyl)amino]-6-methylquinazolin-2-yl}-2-methoxybenzamide dihydrochloride Elemental analysis for $C_{24}H_{29}N_7O_2.2HCl.H_2O$ Calcd. (%): C, 53.53; H, 6.18; N, 18.20. Found (e): C, 53.54; H, 6.15; N, 17.00.

Positive ion FAB-MS m/z: 448[M+H]$^+$

Specific rotation $[\alpha]^{20}_D$=−90.94 (c=1.0 methanol)

EXAMPLE 5

N-{4-[((1S,2R)-2-{[amino(imino)methyl]amino}cyclohexyl)amino]-6-methylquinazolin-2-yl}-4-methoxy-2-methylbenzamide dihydrochloride Elemental analysis for $C_{25}H_{31}N_7O_2.2HCl.2H_2O$ Calcd. (%): C, 52.63; H, 6.54; N, 17.19. Found (%): C, 52.88; H, 6.34; N, 17.24.

Positive ion FAB-MS m/z: 462[M+H]$^+$

Specific rotation $[\alpha]^{20}_D$=−83.79 (c=1.0 methanol)

EXAMPLE 6

N-{4-[((1S,2R)-2-{[amino(imino)methyl]amino}cyclohexyl)amino]-6-methylquinazolin-2-yl}-2,4-dimethoxybenzamide dihydrochloride Elemental analysis for $C_{25}H_{31}N_7O_3.2HCl.H_2O$ Calcd. (%): C, 52.81; H, 6.21; N, 17.25. Found (%): C, 52.98; H, 5.93; N, 17.26.

Positive ion FAB-MS m/z: 478[M+H]$^+$

Specific rotation $[\alpha]^{20}_D$=−89.00 (c=1.0 methanol)

EXAMPLE 7

N-{4-[((1S,2R)-2-{[amino(imino)methyl]amino}cyclohexyl)amino]-6-methylquinazolin-2-yl}-6-methoxy-2-naphthamide dihydrochloride Elemental analysis for $C_{28}H_{31}N_7O_2.2HCl.1.25H_2O$ Calcd. (%): C, 56.71; H, 6.03; N, 16.53. Found (%): C, 56.72; H, 6.22; N, 16.11.

Positive ion FAB-MS m/z: 498[M+H]$^+$

Specific rotation $[\alpha]^{20}_D$=−121.06 (c=1.0 methanol)

EXAMPLE 8

N-{4-[((1S,2R)-2-{[amino(imino)methyl]amino}cyclohexyl)amino]-6-methylquinazolin-2-yl}-3,4-dimethoxybenzamide dihydrochloride Elemental analysis for $C_{25}H_{31}N_7O_3.2HCl.2H_2O$ Calcd. (%): C, 48.20; H, 6.15; N, 17.24. Found (%): C, 48.28; H, 6.10; N, 17.20.

Positive ion FAB-MS m/z: 478[M+H]$^+$

Specific rotation $[\alpha]^{20}_D$=−87.16 (c=1.0 methanol)

EXAMPLE 9

N-{4-[((1S,2R)-2-{[amino(imino)methyl]amino}cyclohexyl)amino]-6-methylquinazolin-2-yl}-1,3-benzodioxole-5-carboxamide dihydrochloride Elemental analysis for $C_{24}H_{27}N_7O_3.2HCl.H_2O$ Calcd. (%): C, 48.95; H, 5.48; N, 16.65. Found (%): C, 48.80; H, 5.22; N, 16.38.

EXAMPLE 10

N-{4-[((1S,2R)-2-{[amino(imino)methyl]amino}cyclohexyl)amino]-6-methylquinazolin-2-yl}-4-tert-butylbenzamide dihydrochloride Positive ion FAB-MS m/z: 474[M+H]$^+$

EXAMPLE 11

N-{4-[((1S,2R)-2-{[amino(imino)methyl]amino}cyclohexyl)amino]-6-methylquinazolin-2-yl}-2,2-dimethylpropanamide dihydrochloride.

Positive ion FAB-MS m/z: 398[M+H]$^+$

EXAMPLE 12

N-{4-[((1S,2R)-2-{[amino(imino)methyl]amino}cyclohexyl)amino]-6-methylquinazolin-2-yl}-4-methoxybenzamide dihydrochloride Elemental analysis for $C_{24}H_{29}N_7O_2 \cdot 2HCl \cdot 1.5H_2O$ Calcd. (%): C, 52.65; H, 6.26; N, 17.91. Found (%): C, 52.61; H, 6.06; N, 17.96.

Positive ion FAB-MS m/z: 448[M+H]$^+$
Specific rotation $[\alpha]^{20}_D = -101.98$ (c 1.0 methanol)

EXAMPLE 13

N-{4-[((1S,2R)-2-{[amino(imino)methyl]amino}cyclohexyl)amino]-6-methylquinazolin-2-yl}-4-ethoxybenzamide dihydrochloride Positive ion FAB-MS m/z: 462[M+H]$^+$

EXAMPLE 14

N-{4-[((1S,2R)-2-{[amino(imino)methyl]amino}cyclohexyl)amino]-6-methylquinazolin-2-yl}-4-isopropoxybenzamide dihydrochloride Positive ion FAB-MS m/z: 476[M+H]$^+$

EXAMPLE 15

4-[((1S,2R)-2-{[amino(imino)methyl]amino}cyclohexyl)amino]-N,6-dimethylquinazoline-2-carboxamide dihydrochloride Positive ion FAB-MS m/z: 356[M+H]$^+$

EXAMPLE 16

N-[4-({2-[2-(2-{[amino(imino)methyl]amino}ethyl)phenyl]ethyl}amino)-6-methylquinazolin-2-yl]-4-methoxybenzamide dihydrochloride Positive ion FAB-MS m/z: 498[M+H]$^+$

EXAMPLE 17

4-[((1S,2R)-2-{[amino(imino)methyl]amino}cyclohexyl)amino]-8-bromo-N-isobutyl-6-methylquinazoline-2-carboxamide dihydrochloride.

Positive ion FAB-MS m/z: 476[M+H]$^+$

EXAMPLE 18

N-{4-[((1S,2R)-2-{[amino(imino)methyl]amino}cyclohexyl)amino]-6-methylquinazolin-2-yl}-4-(methylthio)benzamide dihydrochloride.

Positive ion FAB-MS m/z: 464[M+H]$^+$

EXAMPLE 19

N-{4-[((1S,2R)-2-{[amino(imino)methyl]amino}cyclohexyl)amino]-6-methylquinazolin-2-yl}-4-(trifluoromethoxy)benzamide dihydrochloride.

Positive ion FAB-MS m/z: 502[M+H]$^+$

EXAMPLE 20

N-{4-[((1S,2R)-2-{[amino(imino)methyl]amino}cyclohexyl)amino]-6-methylquinazolin-2-yl}-2-(methylthio)benzamide dihydrochloride.

Positive ion FAB-MS m/z: 464[M+H]$^+$

EXAMPLE 21

N-{4-[((1S,2R)-2-{[amino(imino)methyl]amino}cyclohexyl)amino]-6-methylquinazolin-2-yl}-5-methoxy-3-methyl-1-benzofuran-2-carboxamide dihydrochloride.

Positive ion FAB-MS m/z: 502[M+H]$^+$

EXAMPLE 22

N-{4-[((1S,2R)-2-{[amino(imino)methyl]amino}cyclohexyl)amino]-6-methylquinazolin-2-yl}quinoline-3-carboxamide trihydrochloride.

Positive ion FAB-MS m/z: 469[M+H]$^+$

EXAMPLE 23

4-[((1S,2R)-2-{[amino(imino)methyl]amino}cyclohexyl)amino]-6-methyl-N-(2-oxo-2,3-dihydro-1,3-benzoxazol-5-yl)quinazoline-2-carboxamide dihydrochloride Positive ion FAB-MS m/z: 475[M+H]$^+$

EXAMPLE 24

N-{4-[((1S,2R)-2-{[amino(imino)methyl]amino}cyclohexyl)amino]-6-chloroquinazolin-2-yl}-4-methoxybenzamide dihydrochloride Positive ion FAB-MS m/z: 468[M+H]$^+$

EXAMPLE 25

N-{4-[((1S,2R)-2-{[amino(imino)methyl]amino}cyclohexyl)amino]-6-methylquinazolin-2-yl}-2-(dimethylamino)benzamide dihydrochloride Positive ion FAB-MS m/z: 461[M+H]$^+$

EXAMPLE 26

4-[((1S,2R)-2-{[amino(imino)methyl]amino}cyclohexyl)amino]-N-(4-bromophenyl)-6-methylquinazoline-2-carboxamide dihydrochloride Positive ion FAB-MS m/z; 496[M+H]$^+$

EXAMPLE 27

N-{4-[((1S,2R)-2-{[amino(imino)methyl]amino}cyclohexyl)amino]-6-methylquinazolin-2-yl}-2-(4-methoxyphenyl)acetamide dihydrochloride.

Positive ion FAB-MS m/z: 462[M+H]$^+$

EXAMPLE 28

4-[((1S,2R)-2{[amino(imino)methyl]amino}cyclohexyl)amino]-6-methyl-N-{4-[(methylsulfonyl)amino]phenyl}quinazoline-2-carboxamide dihydrochloride Positive ion FAB-MS m/z: 511[M+H]$^+$

EXAMPLE 29

4-[((1S,2R)-2-{[amino(imino)methyl]amino}cyclohexyl)amino]-6-methyl-N-neopentylquinazoline-2-carboxamide dihydrochloride Positive ion FAB-MS m/z: 412[M+H]$^+$

EXAMPLE 30

4-[((1S,2R)-2-{[amino(imino)methyl]amino}cyclohexyl)amino]-N-(4-methoxybenzyl)-6-methylquinazoline-2-carboxamide dihydrochloride Positive ion FAB-MS m/z: 462[M+H]$^+$

EXAMPLE 31

4-[((1S,2R)-2-{[amino(imino)methyl]amino}cyclohexyl)amino]-N-(4-methoxyphenyl)-N,6-dimethylquinazoline-2-carboxamide dihydrochloride Positive ion FAB-MS m/z: 462[M+H]$^+$

EXAMPLE 32

4-[((1S,2R)-2-{[amino(imino)methyl]amino}cyclohexyl)amino]-N-{[(2R)-6,6-dimethylbicyclo[3.1.1]hept-2-yl]methyl}-6-methylquinazoline-2-carboxamide dihydrochloride Positive ion FAB-MS m/z: 478[M+H]$^+$

EXAMPLE 33

4-[((1S,2R)-2-{[amino(imino)methyl]amino}cyclohexyl)amino]-N-1-benzothiophen-2-yl-6-methylquinazoline-2-carboxamide dihydrochloride Positive ion FAB-MS m/z: 474[M+H]$^+$

EXAMPLE 34

4-[((1S,2R)-2-{[amino(imino)methyl]amino}cyclohexyl)amino]-N-(2-hydroxyethyl)-6-methylquinazoline-2-carboxamide dihydrochloride Positive ion FAB-MS m/z: 386[M+H]$^+$

EXAMPLE 35

4-[((1S,2R)-2-{[amino(imino)methyl]amino}cyclohexyl)amino]-6-methyl-N-thiophen-3-ylquinazoline-2-carboxamide dihydrochloride Positive ion FAB-MS m/z: 424[M+H]$^+$

EXAMPLE 36

4-[((1S,2R)-2-{[amino(imino)methyl]amino}cyclohexyl)amino]-6-methyl-N-pyridin-2-ylquinazoline-2-carboxamide trihydrochloride Positive ion FAB-MS m/z; 419[M+H]$^+$

EXAMPLE 37

4-[((1S,2R)-2-{[amino(imino)methyl]amino}cyclohexyl)amino]-6-methyl-N-quinolin-3-ylquinazoline-2-carboxamide trihydrochloride Positive ion FAB-MS m/z: 469[M+H]$^+$

EXAMPLE 38

4-[((1S,2R)-2-{[amino(imino)methyl]amino}cyclohexyl)amino]-N-(4-chlorophenyl)-6-methylquinazoline-2-carboxamide dihydrochloride Positive ion FAB-MS m/z: 452[M+H]$^+$

EXAMPLE 39

N-{4-[((1S,2R)-2-{[amino(imino)methyl]amino}cyclohexyl)amino]-6-methylquinazolin-2-yl}-3-methyl-1-benzothiophene-2-carboxamide dihydrochloride.

Positive ion FAB-MS m/z 488[M+H]$^+$

EXAMPLE 40

N-({4-[((1S,2R)-2-{[amino(imino)methyl]amino}cyclohexyl)amino]-6-methylquinazolin-2-yl}carbonyl)glycine methyl ester dihydrochloride Positive ion FAB-MS m/z: 414[M+H]$^+$

EXAMPLE 41

4-[((1S,2R)-2-{[amino(imino)methyl]amino}cyclohexyl)amino]-6-chloro-N-(4-methoxyphenyl)quinazoline-2-carboxamide dihydrochloride Positive ion FAB-MS m/z: 468[M+H]$^+$

EXAMPLE 42

4-[((1S,2R)-2-{[amino(imino)methyl]amino}cyclohexyl)amino]-6-methoxy-N-(4-methoxyphenyl)quinazoline-2-carboxamide dihydrochloride Positive ion FAB-MS m/z: 464[M+H]$^+$

EXAMPLE 43

4-[((1S,2R)-2-{[amino(imino)methyl]amino}cyclohexyl)amino]-6-methyl-N-(2-phenoxyethyl)quinazoline-2-carboxamide trihydrochloride Positive ion FAB-MS m/z: 462[M+H]$^+$

EXAMPLE 44

N-(2-amino-1,1-dimethylethyl)-4-[((1S,2R)-2-{[amino(imino)methyl]amino}cyclohexyl)amino]-6-methylquinazoline-2-carboxamide trihydrochloride Positive ion FAB-MS m/z: 413[M+H]$^+$

EXAMPLE 45

4-[((1S,2R)-2-{[amino(imino)methyl]amino}cyclohexyl)amino]-6-methyl-N-(1-methyl-1H-benzimidazol-2-yl)quinazoline-2-carboxamide trihydrochloride Positive ion FAB-MS m/z; 472[M+H]$^+$

EXAMPLE 46

4-[((1S,2R)-2-{[amino(imino)methyl]amino}cyclohexyl)amino]-6-methyl-N-thiophen-2-ylquinazoline-2-carboxamide dihydrochloride Positive ion FAB-MS m/z: 424[M+H]$^+$

EXAMPLE 47

4-[((1S,2R)-2-{[amino(imino)methyl]amino}cyclohexyl)amino]-N-(4-methoxyphenyl)quinazoline-2-carboxamide dihydrochloride Positive ion FAB-MS m/z: 434[M+H]$^+$

EXAMPLE 48

4-[((1S,2R)-2-{[amino(imino)methyl]amino}cyclohexyl)amino]-N-(2-methoxyethyl)-6-methylquinazoline-2-carboxamide dihydrochloride Positive ion FAB-MS m/z: 400[M+H]$^+$

EXAMPLE 49

4-[((1S,2R)-2-{[amino(imino)methyl]amino}cyclohexyl)amino]-6-methyl-N-[4-(trifluoromethoxy)phenyl]quinazoline-2-carboxamide dihydrochloride Positive ion FEM-Ms m/z: 502[M+H]$^+$

EXAMPLE 50

4-[((1S,2R)-2-{[amino(imino)methyl]amino}cyclohexyl)amino]-N-(3,5-dimethylphenyl)-6-methylquinazoline-2-carboxamide dihydrochloride Positive ion FAB-MS m/z: 446[M+H]$^+$

EXAMPLE 51

4-[((1S,2R)-2-{[amino(imino)methyl]amino}cyclohexyl)amino]-N-(2,6-dimethylphenyl)-6-methylquinazoline-2-carboxamide dihydrochloride Positive ion FAB-MS m/z: 446[M+H]$^+$

EXAMPLE 52

4-[((1S,2R)-2-{[amino(imino)methyl]amino}cyclohexyl)amino]-N-(3,4-dimethylphenyl)-6-methylquinazoline-2-carboxamide dihydrochloride Positive ion FAB-MS m/z: 446[M+H]$^+$

EXAMPLE 53

4-[((1S,2R)-2-{[amino(imino)methyl]amino}cyclohexyl)amino]-6-methyl-N-(2-oxo-2H-chromen-6-yl)quinazoline-2-carboxamide dihydrochloride Positive ion FAB-MS m/z: 486[M+H]$^+$

EXAMPLE 54

N-{4-[((1S,2R)-2-{[amino(imino)methyl]amino}cyclohexyl)amino]-6-methoxyquinazolin-2-yl}-4-methoxybenzamide dihydrochloride Positive ion FAB-MS m/z: 464[M+H]$^+$

EXAMPLE 55

4-[((1S,2R)-2-{[amino(imino)methyl]amino}cyclohexyl)amino]-N-(3-chloro-4-methoxyphenyl)-6-methylquinazoline-2-carboxamide dihydrochloride Positive ion FAB-MS m/z 482[M+H]$^+$

EXAMPLE 56

4-[((1S,2R)-2-{[amino(imino)methyl]amino}cyclohexyl)amino]-6-methyl-N-(3-oxo-3,4-dihydro-2H-1,4-benzoxazin-6-yl)quinazoline-2-carboxamide dihydrochloride Positive ion FAB-MS m/z: 489[M+H]$^+$

EXAMPLE 57

4-[((1S,2R)-2-{[amino(imino)methyl]amino}cyclohexyl)amino]-N-(6-chloropyridin-3-yl)-6-methylquinazoline-2-carboxamide trihydrochloride Positive ion FAB-MS m/z: 453[M+H]$^+$

EXAMPLE 58

4-[((1S,2R)-2-{[amino(imino)methyl]amino}cyclohexyl)amino]-N-(3-hydroxy-2,2-dimethylpropyl)-6-methylquinazoline-2-carboxamide dihydrochloride Positive ion FAB-MS m/z: 428[M+H]$^+$

EXAMPLE 59

4-[((1S,2R)-2-{[amino(imino)methyl]amino}cyclohexyl)amino]-N-(3-methoxy-2,2-dimethylpropyl)-6-methylquinazoline-2-carboxamide dihydrochloride Positive ion FAB-MS m/z: 442[M+H]$^+$

EXAMPLE 60

N-{4-[((1R,2S)-2-{[amino(imino)methyl]amino}cyclohexyl)amino]-6-methylquinazolin-2-yl}-4-methoxybenzamide dihydrochloride Positive ion FAB-MS m/z: 448[M+H]$^+$

EXAMPLE 61

4-[((1S,2R)-2-{[amino(imino)methyl]amino}cyclohexyl)amino]-N-(2,2-diphenylpropyl)-6-methylquinazoline-2-carboxamide dihydrochloride Positive ion FAB-MS m/z: 536[M+H]$^+$

EXAMPLE 62

4-[((1S,2R)-2-{[amino(imino)methyl]amino}cyclohexyl)amino]-N-[2-(diethylamino)ethyl]-6-methylquinazoline-2-carboxamide trihydrochloride Positive ion FAB-MS m/z: 441[M+H]$^+$

EXAMPLE 63

4-[((1S,2R)-2-{[amino(imino)methyl]amino}cyclohexyl)amino]-N-[(1S)-2-methoxy-1-(4-methoxybenzyl)ethyl]-6-methylquinazoline-2-carboxamide dihydrochloride Positive ion FAB-MS m/z: 520[M+H]$^+$

EXAMPLE 64

4-[((1S,2R)-2-{[amino(imino)methyl]amino}cyclohexyl)amino]-N-(3,3-dimethylbutyl)-6-methylquinazoline-2-carboxamide trihydrochloride Positive ion FAB-MS m/z: 426[M+H]$^+$

EXAMPLE 65

4-[((1S,2R)-2-{[amino(imino)methyl]amino}cyclohexyl)amino]-N-(4-methoxyphenyl)-5-methylquinazoline-2-carboxamide dihydrochloride Positive ion FAB-MS m/z: 448[M+H]$^+$

EXAMPLE 66

N-({4-[((1S,2R)-2-{[amino(imino)methyl]amino}cyclohexyl)amino]-6-methylquinazolin-2-yl}carbonyl)-2-methylalanine dihydrochloride.

Positive ion FAB-MS m/z: 428[M+H]$^+$

EXAMPLE 67

4-[((1S,2R)-2-{[amino(imino)methyl]amino}cyclohexyl)amino]-N-(2-hydroxy-1,1-dimethylethyl)-6-methylquinazoline-2-carboxamide dihydrochloride Positive ion FAB-MS m/z: 414[M+H]$^+$

EXAMPLE 68

4-[((1S,2R)-2-{[amino(imino)methyl]amino}cyclohexyl)amino]-N-(2-methoxy-1,1-dimethylethyl)-6-methylquinazoline-2-carboxamide dihydrochloride Positive ion FAB-MS m/z: 428[M+H]$^+$

EXAMPLE 69

4-[((1S,2R)-2-{[amino(imino)methyl]amino}cyclohexyl)amino]-N-(1,1-dimethyl-2-phenylethyl)-6-methylquinazoline-2-carboxamide dihydrochloride Positive ion FAB-MS m/z: 474[M+H]$^+$

EXAMPLE 70

N-{4-[((1S,2R)-2-{[amino(imino)methyl]amino}cyclohexyl)amino]-6-methylquinazolin-2-yl}-4-ethylbenzamide dihydrochloride Positive ion FAB-MS m/z: 446[M+H]$^+$

EXAMPLE 71

N-{4-[((1S,2R)-2-{[amino(imino)methyl]amino}cyclohexyl)amino]-6-methylquinazolin-2-yl}-3,4-dimethylbenzamide dihydrochloride Positive ion FAB-MS m/z: 446[M+H]$^+$

EXAMPLE 72

N-[2-(acetylamino)-1,1-dimethylethyl]-4-[((1S,2R)-2-{[amino(imino)methyl]amino}cyclohexyl)amino]-6-methylquinazoline-2-carboxamide dihydrochloride Positive ion FAB-MS m/z: 455[M+H]$^+$

EXAMPLE 73

4-[((1S,2R)-2-{[amino(imino)methyl]
amino}cyclohexyl)amino]-N-{1,1-dimethyl-2-[(methylsulfonyl)amino]ethyl}-6-methylquinazoline-2-carboxamide dihydrochloride Positive ion FAB-MS m/z: 491[M+H]$^+$

EXAMPLE 74

4-[((1S,2R)-2-{[amino(imino)methyl]
amino}cyclohexyl)amino]-6-methyl-N-{4-[(E)-2-phenylvinyl]phenyl}quinazoline-2-carboxamide dihydrochloride Positive ion FAB-MS m/z: 520[M+H]$^+$

EXAMPLE 75

4-[((1S,2R)-2-{[amino(imino)methyl]
amino}cyclohexyl)amino]-6,7-dimethoxy-N-(4-methoxyphenyl)quinazoline-2-carboxamide dihydrochloride Positive ion RAB-MS m/z: 494[M+H]$^+$

EXAMPLE 76

N-{4-[((1RS,2SR)-2-{[amino(imino)methyl]
amino}cyclohexyl)amino]-6-methylquinazolin-2-yl}-2-chlorobenzamide bis(trifluoroacetate)

Positive ion FAB-MS m/z: 452[M+H]$^+$

EXAMPLE 77

N-{4-[((1RS,2SR)-2-{[amino(imino)methyl]
amino}cyclohexyl)amino]-6-methylquinazolin-2-yl}4-bromobenzamide bis(trifluoroacetate)

Positive ion FAB-MS m/z: 496[M+H]$^+$

EXAMPLE 78

N-{4-[((1RS,2SR)-2-{[amino(imino)methyl]
amino}cyclohexyl)amino]-6-methylquinazolin-2-yl}-2-naphthamide bis(trifluoroacetate)

Positive ion FAB-MS m/z: 468[M+H]$^+$

EXAMPLE 79

N-{4-[((1RS,2SR)-2-{[amino(imino)methyl]
amino}cyclohexyl)amino]-6-methylquinazolin-2-yl}-1,1'-biphenyl-4-carboxamide bis(trifluoroacetate)

Positive ion FAB-MS m/z: 494[M+H]$^+$

EXAMPLE 80

N-{4-[((1RS,2SR)-2-{[amino(imino)methyl]
amino}cyclohexyl)amino]-6-methylquinazolin-2-yl}benzamide bis(trifluoroacetate)

Positive ion FAB-MS m/z: 418[M+H]$^+$

EXAMPLE 81

N-{4-[((1RS,2SR)-2-{[amino(imino)methyl]
amino}cyclohexyl)amino]-6-methylquinazolin-2-yl}-4-(trifluoromethyl)benzamide bis(trifluoroacetate)

Positive ion FAB-MS m/z: 486[M+H]$^+$

EXAMPLE 82

N-{4-[(1RS,2SR)-2-{[amino(imino)methyl]
amino}cyclohexyl)amino]-6-methylquinazolin-2-yl}-4-fluorobenzamide bis(trifluoroacetate)

Positive ion FAB-MS m/z: 436[M+H]$^+$

EXAMPLE 83

N-{4-[((1RS,2SR)-2-{[amino(imino)methyl]
amino}cyclohexyl)amino]-6-methylquinazolin-2-yl}-2,2-diphenylacetamide bis(trifluoroacetate)

Positive ion FAB-MS m/z: 508[M+H]$^+$

EXAMPLE 84

N-{4-[((1RS,2SR)-2-{[amino(imino)methyl]
amino}cyclohexyl)amino]-6-methylquinazolin-2-yl}adamantane-1-carboxamide bis(trifluoroacetate)

Positive ion FAB-MS m/z: 476[M+H]$^+$

EXAMPLE 85

(2E)-N-{4-[((1RS,2SR)-2-{[amino(imino)methyl]
amino}cyclohexyl)amino]-6-methylquinazolin-2-yl}-3-phenylacrylamide bis(trifluoroacetate)

Positive ion FAB-MS m/z: 444[M+H]$^+$

EXAMPLE 86

N-{4-[((1RS,2SR)-2-{[amino(imino)methyl]
amino}cyclohexyl)amino]-6-methylquinazolin-2-yl}-1-benzothiophene-3-carboxamide bis(trifluoroacetate)

Positive ion FAB-MS m/z: 474[M+H]$^+$

EXAMPLE 87

N-{4-[((1RS,2SR)-2-{[amino(imino)methyl]
amino}cyclohexyl)amino]-6-methylquinazolin-2-yl}-4-cyanobenzamide bis(trifluoroacetate)

Positive ion FAB-MS m/z: 443[M+H]$^+$

EXAMPLE 88

N-{4-[((1RS,2SR)-2-{[amino(imino)methyl]
amino}cyclohexyl)amino]-6-methylquinazolin-2-yl}-1-benzyl-3-tert-butyl-1H-pyrazole-5-carboxamide bis(trifluoroacetate)

Positive ion FAB-MS m/z; 554[M+H]$^+$

EXAMPLE 89

N-{4-[((1RS,2SR)-2-{[amino(imino)methyl]amino}cyclohexyl)amino]-6-methylquinazolin-2-yl}thiophene-2-carboxamide bis(trifluoroacetate)

Positive ion FAB-MS m/z: 424[M+H]$^+$

EXAMPLE 90

N-{4-[((1RS,2SR)-2-{[amino(imino)methyl]amino}cyclohexyl)amino]-6-methylquinazolin-2-yl}-3,5-dimethylisoxazole-4-carboxamide bis(terifluoroacetate)

Positive ion FAB-MS m/z: 437[M+H]$^+$

EXAMPLE 91

N-{4-[((1RS,2SR)-2-{[amino(imino)methyl]amino}cyclohexyl)amino]-6-methylquinazolin-2-yl}-4-methoxybenzamide bis(trifluoroacetate)

Positive ion FAB-MS m/z: 448[M+H]$^+$

EXAMPLE 92

N-{4-[((1RS,2SR)-2-{[amino(imino)methyl]amino}cyclohexyl)amino]-6-methylquinazolin-2-yl}-3-chlorobenzamide bis(trifluoroacetate)

Positive ion FAB-MS m/z; 452[M+H]$^+$

EXAMPLE 93

N-{4-[((1RS,2SR)-2-{[amino(imino)methyl]amino}cyclohexyl)amino]-6-methylquinazolin-2-yl}-2,4-dichlorobenzamide bis(trifluoroacetate)

Positive ion FAB-MS m/z: 486[M+H]$^+$

EXAMPLE 94

N-{4-[((1RS,2SR)-2-{[amino(imino)methyl]amino}cyclohexyl)amino]-6-methylquinazolin-2-yl}-4-nitrobenzamide bis(trifluoroacetate)

Positive ion FAB-MS m/z: 463[M+H]$^+$

EXAMPLE 95

N-{4-[((1RS,2SR)-2-{[amino(imino)methyl]amino}cyclohexyl)amino]-6-methylquinazolin-2-yl}-1,3-benzodioxole-5-carboxamide bis(trifluoroacetate)

Positive ion FAB-MS m/z: 462[M+H]$^+$

EXAMPLE 96

N-{4-[((1RS,2SR)-2-{[amino(imino)methyl]amino}cyclohexyl)amino]-6-methylquinazolin-2-yl}-4-ethylbenzamide bis(trifluoroacetate)

Positive ion FAB-MS m/z: 446[M+H]$^+$

EXAMPLE 97

N-{4-[((1RS,2SR)-2-{[amino(imino)methyl]amino}cyclohexyl)amino]-6-methylquinazolin-2-yl}-4-(trifluoromethoxy)benzamide bis(trifluoroacetate)

Positive ion FAB-MS m/z: 502[M+H]$^+$

EXAMPLE 98

N-{4-[((1RS,2SR)-2-{[amino(imino)methyl]amino}cyclohexyl)amino]-6-methylquinazolin-2-yl}furan-2-carboxamide bis(trifluoroacetate)

Positive ion FAB-MS m/z: 408[M+H]$^+$

EXAMPLE 99

N-{4-[((1RS,2SR)-2-{[amino(imino)methyl]amino}cyclohexyl)amino]-6-methylquinazolin-2-yl}-2-(1-naphthyl)acetamide bis(trifluoroacetate)

Positive ion FAB-MS m/z: 482[M+H]$^+$

EXAMPLE 100

N-{4-[((1RS,2SR)-2-{[amino(imino)methyl]amino}cyclohexyl)amino]-6-methylquinazolin-2-yl}-4-(benzyloxy)butanamide bis(trifluoroacetate)

Positive ion FAB-MS m/z; 490[M+H]$^+$

EXAMPLE 101

N-{4-[((1RS,2SR)-2-{[amino(imino)methyl]amino}cyclohexyl)amino]-6-methylquinazolin-2-yl}-3-methyl-1H-inden-2-carboxamide bis(trifluoroacetate)

Positive ion FAB-MS m/z: 470[M+H]$^+$

EXAMPLE 102

N-{4-[((1RS,2SR)-2-{[amino(imino)methyl]amino}cyclohexyl)amino]-6-methylquinazolin-2-yl}-5-(4-nitrophenyl)furan-2-carboxamide bis(trifluoroacetate)

Positive ion FAB-MS m/z; 529[M+H]$^+$

EXAMPLE 103

4-acetyl-N-{4-[((1RS,2SR)-2-{[amino(imino)methyl]amino}cyclohexyl)amino]-6-methylquinazolin-2-yl}benzamide bis(trifluoroacetate)

Positive ion FAB-MS m/z: 460[M+H]$^+$

EXAMPLE 104

(2E)-N-{4-[((1RS,2SR)-2-{[amino(imino)methyl]amino}cyclohexyl)amino]-6-methylquinazolin-2-yl}-3-(3,4-dichlorophenyl)acrylamide bis(trifluoroacetate)

Positive ion FAB-MS m/z: 512[M+H]$^+$

EXAMPLE 105

N-{4-[((1RS,2SR)-2-{[amino(imino)methyl]amino}cyclohexyl)amino]-6-methylquinazolin-2-yl}cycloheptanecarboxamide bis(trifluoroacetate)

Positive ion FAB-MS m/z: 438[M+H]$^+$

EXAMPLE 106

N-{4-[((1RS,2SR)-2-{[amino(imino)methyl]amino}cyclohexyl)amino]-6-methylquinazolin-2-yl}quinoline-3-carboxamide tris(trifluoroacetate)

Positive ion FAB-MS m/z: 469[M+H]$^+$

EXAMPLE 107

N-{4-[((1RS,2SR)-2-{[amino(imino)methyl]amino}cyclohexyl)amino]-6-methylquinazolin-2-yl}-4-(1H-pyrrol-1-yl)benzamide tris(trifluoroacetate)

Positive ion FAB-MS m/z: 483[M+H]8 $^+$

EXAMPLE 108

N-{4-[((1RS,2SR)-2-{[amino(imino)methyl]amino}cyclohexyl)amino]-6-methylquinazolin-2-yl}-4-tert-butylcyclohexanecarboxamide bis(trifluoroacetate)

Positive ion FAB-MS m/z: 480[M+H]$^+$

EXAMPLE 109

N-{4-[((1RS,2SR)-2-{[amino(imino)methyl]amino}cyclohexyl)amino]-6-methylquinazolin-2-yl}-4-pentenamide bis(trifluoroacetate)

Positive ion FAB-MS m/z: 396[M+H]$^+$

EXAMPLE 110

N-{4-[((1RS,2SR)-2-{[amino(imino)methyl]amino}cyclohexyl)amino]-6-methylquinazolin-2-yl}-2-(4-chlorophenyl)acetamide bis(trifluoroacetate)

Positive ion FAB-MS m/z: 466[M+H]$^+$

EXAMPLE 111

N-{4-[((1RS,2SR)-2-{[amino(imino)methyl]amino}cyclohexyl)amino]-6-methylquinazolin-2-yl}-1-benzofuran-2-carboxamide bis(trifluoroacetate)

Positive ion FAB-MS m/z: 458[M+H]$^+$

EXAMPLE 112

N-{4-[((1RS,2SR)-2-{[amino(imino)methyl]amino}cyclohexyl)amino]-6-methylquinazolin-2-yl}-5-chloro-1H-indole-2-carboxamide bis(trifluoroacetate)

Positive ion FAB-MS m/z: 491[M+H]$^+$

EXAMPLE 113

N-{4-[((1RS,2SR)-2-{[amino(imino)methyl]amino}cyclohexyl)amino]-6-methylquinazolin-2-yl}-2-(4-fluorophenyl)acetamide bis(trifluoroacetate)

Positive ion FAB-MS m/z: 450[M+H]$^+$

EXAMPLE 114

N-{4-[((1RS,2SR)-2-{[amino(imino)methyl]amino}cyclohexyl)amino]-6-methylquinazolin-2-yl}-2-cyclohexylacetamide bis(trifluoroacetate)

Positive ion FAB-MS m/z: 438[M+H]$^+$

EXAMPLE 115

N-{4-[((1RS,2SR)-2-{[amino(imino)methyl]amino}cyclohexyl)amino]-6-methylquinazolin-2-yl}-4-vinylbenzamide bis(trifluoroacetate)

Positive ion FAB-MS m/z: 444[M+H]$^+$

EXAMPLE 116

N-{4-[((1RS,2SR)-2-{[amino(imino)methyl]amino}cyclohexyl)amino]-6-methylquinazolin-2-yl}-4-methyl-3-pentenamide bis(trifluoroacetate)

Positive ion FAB-MS m/z: 410[M+H]$^+$

EXAMPLE 117

6-(acetylamino)-N-{4-[((1RS,2SR)-2-{[amino(imino)methyl]amino}cyclohexyl)amino]-6-methylquinazolin-2-yl}hexanamide bis(trifluoroacetate)

Positive ion FAB-MS m/z: 469[M+H]$^+$

EXAMPLE 118

2-(3-acetyl-2,2-dimethylcyclobutyl)-N-{4-[((1RS,2SR)-2-{[amino(imino)methyl]amino}cyclohexyl)amino]-6-methylquinazolin-2-yl}acetamide bis(trifluoroacetate)

Positive ion FAB-MS m/z: 480[M+H]$^+$

EXAMPLE 119

N-{4-[((1RS,2SR)-2-{[amino(imino)methyl]amino}cyclohexyl)amino]-6-methylquinazolin-2-yl}-4-(methylsulfonyl)benzamide bis(trifluoroacetate)

Positive ion FAB-MS m/z: 496[M+H]$^+$

EXAMPLE 120

N-{4-[((1RS,2SR)-2-{[amino(imino)methyl]amino}cyclohexyl)amino]-6-methylquinazolin-2-yl}-3-(phenylsulfonyl)propanamide bis(trifluoroacetate)

Positive ion FAB-MS m/z; 510[M+H]$^+$

EXAMPLE 121

N-{4-[((1RS,2SR)-2-{[amino(imino)methyl]amino}cyclohexyl)amino]-6-methylquinazolin-2-yl}-N,N-dimethylphenylalanineamide tris(trifluoroacetate)

Positive ion FAB-MS m/z: 489[M+H]$^+$

EXAMPLE 122

N-{4-[((1RS,2SR)-2-{[amino(imino)methyl]amino}cyclohexyl)amino]-6-methylquinazolin-2-yl}-4-(aminosulfonyl)benzamide bis(trifluoroacetate)

Positive ion FAB-MS m/z: 497[M+H]$^+$

EXAMPLE 123

N-{4-[((1RS,2SR)-2-{[amino(imino)methyl]amino}cyclohexyl)amino]-6-methylquinazolin-2-yl}-1-phenylcyclopentanecarboxamide bis(trifluoroacetate)

Positive ion FAB-MS m/z: 486[M+H]$^+$

EXAMPLE 124

N-{4-[((1RS,2SR)-2-{[amino(imino)methyl]amino}cyclohexyl)amino]-6-methylquinazolin-2-yl}-4-[(di-n-propylamino)sulfonyl]benzamide bis(trifluoroacetate)

Positive ion FAB-MS m/z: 581[M+H]$^+$

EXAMPLE 125

N-{4-[((1RS,2SR)-2-{[amino(imino)methyl]amino}cyclohexyl)amino]-6-methylquinazolin-2-yl}-1-methyl-1H-indole-2-carboxamide bis(trifluoroacetate)

Positive ion FAB-MS m/z: 471[M+H]$^+$

EXAMPLE 126

4-(acetylamino)-N-{4-[((1RS,2SR)-2-{[amino(imino)methyl]amino}cyclohexyl)amino]-6-methylquinazolin-2-yl}benzamide bis(trifluoroacetate)

Positive ion FAB-MS m/z: 475[M+H]$^+$

EXAMPLE 127

N-{4-[((1RS,2SR)-2-{[amino(imino)methyl]amino}cyclohexyl)amino]-6-methylquinazolin-2-yl}-1H-pyrazole-5-carboxamide bis(trifluoroacetate)

Positive ion FAB-MS m/z: 408[M+H]$^+$

EXAMPLE 128

N-{4-[((1RS,2SR)-2-{[amino(imino)methyl]amino}cyclohexyl)amino]-6-methylquinazolin-2-yl}-3-oxoindane-1-carboxamide bis(trifluoroacetate)

Positive ion FAS-MS m/z: 472[M+H]$^+$

EXAMPLE 130

N-{4-[((1RS,2SR)-2-{[amino(imino)methyl]amino}cyclohexyl)amino]-6-methylquinazolin-2-yl}-4-(3-methyl-5-oxo-4,5-dihydro-1H-pyrazol-1-yl)benzamide bis(trifluoroacetate)

Positive ion FAB-MS m/z: 514[M+H]$^+$

EXAMPLE 131

N-{4-[((1RS,2SR)-2-{[amino(imino)methyl]amino}cyclohexyl)amino]-6-methylquinazolin-2-yl}-2-(methylthio)nicotinamide tris(trifluoroacetate)

Positive ion FAB-MS m/z: 465[M+H]$^+$

EXAMPLE 132

N-{4-[((1RS,2SR)-2-{[amino(imino)methyl]amino}cyclohexyl)amino]-6-methylquinazolin-2-yl}-4-phenoxybenzamide bis(trifluoroacetate)

Positive ion FAB-MS m/z: 510[M+H]$^+$

EXAMPLE 133

N-{4-[((1RS,2SR)-2-{[amino(imino)methyl]amino}cyclohexyl)amino]-6-methylquinazolin-2-yl}quinoline-6-carboxamide tris(trifluoroacetate)

Positive ion FAB-MS m/z: 469[M+H]$^+$

EXAMPLE 134

N-{4-[((1RS,2SR)-2-{[amino(imino)methyl]amino}cyclohexyl)amino]-6-methylquinazolin-2-yl}-4-n-pentylbenzamide bis(trifluoroacetate)

Positive ion FAB-MS m/z: 488[M+H]$^+$

EXAMPLE 135

4-[({4-[((1RS,2SR)-2-{[amino(imino)methyl]amino}cyclohexyl)amino]-6-methylquinazolin-2-yl}amino)carbonyl]benzoic acid methyl ester bis(trifluoroacetate)

Positive ion FAB-MS m/z: 476[M+H]$^+$

EXAMPLE 136

N-{4-[((1RS,2SR)-2-{[amino(imino)methyl]amino}cyclohexyl)amino]-6-methylquinazolin-2-yl}-2-[(3-chloro-4-methyl-2-oxo-2H-chromen-7-yl)oxy]acetamide bis(trifluoroacetate)

Positive ion FAB-MS m/z: 564[M+H]$^+$

EXAMPLE 137

N-{4-[((1RS,2SR)-2-{[amino(imino)methyl]amino}cyclohexyl)amino]-6-methylquinazolin-2-yl}-2-(6-oxo-7,8-dihydro-6H-[1,3]dioxolo[4,5-g]chromen-8-yl)acetamide bis(trifluoroacetate)

Positive ion FAB-MS m/z: 546[M+H]$^+$

EXAMPLE 138

N-{4-[((1RS,2SR)-2-{[amino(imino)methyl]amino}cyclohexyl)amino]-6-methylquinazolin-2-yl}nicotinamide tris(trifluoroacetate)

Positive ion FAB-MS m/z: 419[M+H]$^+$

EXAMPLE 139

N-{4-[((1RS,2SR)-2-{[amino(imino)methyl]amino}cyclohexyl)amino]-6-methylquinazolin-2-yl}-2-(pyrimidin-2-ylthio)acetamide tris(trifluoroacetate)

Positive ion FAB-MS m/z: 466[M+H]$^+$

EXAMPLE 140

N-{4-[((1RS,2SR)-2-{[amino(imino)methyl]amino}cyclohexyl)amino]-6-methylquinazolin-2-yl}-3,3,3-trifluoropropanamide bis(trifluoroacetate)

Positive ion FAB-MS m/z: 424[M+H]$^+$

EXAMPLE 141

N-{4-[((1RS,2SR)-2-{[amino(imino)methyl]amino}cyclohexyl)amino]-6-methylquinazolin-2-yl}-2-(1,3-dioxo-1,3-dihydro-2H-isoindol-2-yl)propanamide bis(trifluoroacetate)

Positive ion FAB-MS m/z: 515[M+H]$^+$

EXAMPLE 142

N-{4-[((1RS,2SR)-2-{[(amino(imino)methyl]amino}cyclohexyl)amino]-6-methylquinazolin-2-yl}-5-n-butylpyridine-2-carboxamide tris(trifluoroacetate)

Positive ion FAB-MS m/z: 475[M+H]$^+$

EXAMPLE 143

N-{4-[((1RS,2SR)-2-{[amino(imino)methyl]amino}cyclohexyl)amino]-6-methylquinazolin-2-yl}-2,2-dimethyl-5-oxotetrahydrofuran-3-carboxamide bis(trifluoroacetate)

Positive ion FAB-MS m/z: 454[M+H]$^+$

EXAMPLE 144

N-{4-[((1RS,2SR)-2-{[amino(imino)methyl]amino}cyclohexyl)amino]-6-methylquinazolin-2-yl}tetrahydrofuran-2-carboxamide bis(trifluoroacetate)

Positive ion FAB-MS m/z: 412[M+H]$^+$

EXAMPLE 145

N-{4-[((1RS,2SR)-2-{[amino(imino)methyl]amino}cyclohexyl)amino]-6methylquinazolin-2-yl}-2-phenylpropanamide bis(trifluoroacetate)

Positive ion FAB-MS m/z: 446[M+H]$^+$

EXAMPLE 146

N-{4-[((1RS,2SR)-2-{[amino(imino)methyl]amino}cyclohexyl)amino]-6-methylquinazolin-2-yl}-2-(phenylthio)acetamide bis(trifluoroacetate)

Positive ion FAB-MS m/z: 464[M+H]$^+$

EXAMPLE 147

N-{4-[((1RS,2SR)-2-{[amino(imino)methyl]amino}cyclohexyl)amino]-6-methylquinazolin-2-yl}-4-(4-methoxyphenyl)butanamide bis(trifluoroacetate)

Positive ion FAB-MS m/z: 490[M+H]$^+$

EXAMPLE 148

N-{4-[((1RS,2SR)-2-{[amino(imino)methyl]amino}cyclohexyl)amino]-6-methylquinazolin-2-yl}-5-bromo-2,3-dihydro-1-benzofuran-7-carboxamide bis(trifluoroacetate)

Positive ion FAB-MS m/z: 538[M+H]$^+$

EXAMPLE 149

N-{4-[((1RS,2SR)-2-{[amino(imino)methyl]amino}cyclohexyl)amino]-6-methylquinazolin-2-yl}-3-chloro-1-benzothiophene-2-carboxamide bis(trifluoroacetate)

Positive ion FAB-MS m/z: 508[M+H]$^+$

EXAMPLE 150

N-{4-[((1RS,2SR)-2-{[amino(imino)methyl]amino}cyclohexyl)amino]-6-methylquinazolin-2-yl}-4-(methylthio)benzamide bis(trifluoroacetate)

Positive ion FAB-MS m/z: 464[M+H]$^+$

EXAMPLE 151

N-{4-[((1RS,2SR)-2-{[amino(imino)methyl]amino}cyclohexyl)amino]-6-methylquinazolin-2-yl}bicyclo[4.2.0]octa-1,3,5-trien-7-carboxamide bis(trifluoroacetate)

Positive ion FAB-MS m/z: 444[M+H]$^+$

EXAMPLE 152

1-acetyl-N-{4-[((1RS,2SR)-2-{[amino(imino)methyl]amino}cyclohexyl)amino]-6-methylquinazolin-2-yl}piperidine-4-carboxamide bis(trifluoroacetate)

Positive ion FAB-MS m/z: 467[M+H]$^+$

EXAMPLE 153

(2R)-N-{4-[((1RS,2SR)-2-{[amino(imino)methyl]amino}cyclohexyl)amino]-6-methylquinazolin-2-yl}-3,3,3-trifluoro-2-methoxy-2-phenylpropanamide bis(trifluoroacetate)

Positive ion FAB-MS m/z; 530[M+H]$^+$

EXAMPLE 154

(1R,4S)-3-[({4-[((1RS,2SR)-2-{[amino(imino)methyl]amino}cyclohexyl)amino]-6-methylquinazolin-2-yl}amino)carbonyl]bicyclo[2.2.1]hept-5-ene-2-carboxylic acid methyl ester bis(trifluoroacetate)

Positive ion FAB-MS m/z: 492[M+H]$^+$

EXAMPLE 155

N-{4-[((1RS,2SR)-2-{[amino(imino)methyl]amino}cyclohexyl)amino]-6-methylquinazolin-2-yl}-9-oxo-9H-fluoren-2-carboxamide bis(trifluoroacetate)

Positive ion FAB-MS m/z: 520[M+H]$^+$

EXAMPLE 156

N-{4-[((1RS,2SR)-2-{[amino(imino)methyl]amino}cyclohexyl)amino]-6-methylquinazolin-2-yl}-2-(3-methylisoxazol-5-yl)acetamide bis(trifluoroacetate)

Positive ion FAB-MS m/z: 437[M+H]$^+$

EXAMPLE 157

N-{4-[((1RS,2SR)-2-{[amino(imino)methyl]amino}cyclohexyl)amino]-6-methylquinazolin-2-yl}-5-nitrofuran-2-carboxamide bis(trifluoroacetate)

Positive ion FAB-MS m/z: 453[M+H]$^+$

EXAMPLE 158

N-{4-[((1RS,2SR)-2-{[amino(imino)methyl]amino}cyclohexyl)amino]-6-methylquinazolin-2-yl}-6-methoxy-2-naphthamide bis(trifluoroacetate)

Positive ion FAB-MS m/z: 498[M+H]$^+$

EXAMPLE 159

N-{4-[((1RS,2SR)-2-{[amino(imino)methyl]amino}cyclohexyl)amino]-6-methylquinazolin-2-yl}-6-bromo-2-naphthamide bis(trifluoroacetate)

Positive ion FAB-MS m/z: 546[M+H]$^+$

EXAMPLE 160

4-[(2-{[(amino(imino)methyl]amino}cyclohexyl)amino]-N-(4-ethylphenyl)-6-methylquinazoline-2-carboxamide bis(trifluoroacetate)

Positive ion FAS-MS m/z: 446[M+H]$^+$

EXAMPLE 161

4-[(2-{[amino(imino)methyl]amino}cyclohexyl)amino]-N-cycloheptyl-6-methylquinazoline-2-carboxamide bis(trifluoroacetate)

Positive ion FAB-MS m/z: 438[M+H]$^+$

EXAMPLE 162

4-[(2-{[amino(imino)methyl]amino}cyclohexyl)amino]-N-(4-methoxybenzyl)-6-methylquinazoline-2-carboxamide bis(trifluoroacetate)

Positive ion FAB-MS m/z: 462[M+H]$^+$

EXAMPLE 163

4-[(2-{[amino(imino)methyl]amino}cyclohexyl)amino]-N-2,3-dihydro-1H-inden-2-yl-6-methylquinazoline-2-carboxamide bis(trifluoroacetate)

Positive ion FAB-MS m/z: 458[M+H]$^+$

EXAMPLE 164

4-[(2-{[amino(imino)methyl]amino}cyclohexyl)amino]-6-methyl-N-quinolin-6-ylquinazoline-2-carboxamide tris(trifluoroacetate)

Positive ion FAB-MS m/z: 469[M+H]$^+$

EXAMPLE 165

4-[(2-{[amino(imino)methyl]amino}cyclohexyl)amino]-N-(4-chlorophenyl)-6-methylquinazoline-2-carboxamide bis(trifluoroacetate)

Positive ion FAB-MS m/z: 452[M+H]$^+$

EXAMPLE 166

4-[(2-{[amino(imino)methyl]amino}cyclohexyl)amino]-N-[2-(2-methoxyphenyl)ethyl]-6-methylquinazoline-2-carboxamide bis(trifluoroacetate)

Positive ion FAB-MS m/z: 476[M+H]$^+$

EXAMPLE 167

4-[(2-{[amino(imino)methyl]amino}cyclohexyl)amino]-6-methyl-N-(3-phenylpropyl)quinazoline-2-carboxamide bis(trifluoroacetate)

Positive ion FAB-MS m/z: 460[M+]$^+$

EXAMPLE 168

4-[(2-{[amino(imino)methyl]amino}cyclohexyl)amino]-6-methyl-N-(2-thiophen-2-ylethyl)quinazoline-2-carboxamide bis(trifluoroacetate)

Positive ion FAB-MS m/z: 452[M+H]$^+$

EXAMPLE 169

4-[(2-{[amino(imino)methyl]amino}cyclohexyl)amino]-N-[(6,6-dimethylbicyclo[3.1.1]hept-2-yl)methyl]-6-methylquinazoline-2-carboxamide bis(trifluoroacetate)

Positive ion FAB-MS m/z: 478[M+H]$^+$

EXAMPLE 170

4-[(2-{[amino(imino)methyl]amino}cyclohexyl)amino]-6-methyl-N-[3-(trifluoromethyl)benzyl]quinazoline-2-carboxamide bis(trifluoroacetate)

Positive ion FAB-MS m/z: 500[M+H]$^+$

EXAMPLE 171

4-[(2-{[amino(imino)methyl]amino}cyclohexyl)amino]-N-(2,2-diphenylethyl)-6-methylquinazoline-2-carboxamide bis(trifluoroacetate)

Positive ion FAB-MS m/z: 522[M+H]$^+$

EXAMPLE 172

4-[((1RS,2SR)-2-{[amino(imino)methyl]amino}cyclohexyl)amino]-N-(3,4-dimethoxybenzyl)-6-methylquinazoline-2-carboxamide bis(trifluoroacetate)

Positive ion FAB-MS m/z: 492[M+H]$^+$

EXAMPLE 173

N-[(1RS,2SR)-2-({6-methyl-2-[(4-phenylpiperazin-1-yl)carbonyl]quinazolin-4-yl}amino)cyclohexyl]guanidine tris(trifluoroacetate)

Positive ion FAB-MS m/z: 487[M+H]$^+$

EXAMPLE 174

4-[((1RS,2SR)-2-{[amino(imino)methyl]amino}cyclohexyl)amino]-N,6-dimethyl-N-(1-methylpiperidin-4-yl)quinazoline-2-carboxamide tris(trifluoroacetate)

Positive ion FAB-MS m/z: 453[M+H]$^+$

EXAMPLE 175

N-((1RS,2SR)-2-{[6-methyl-2-(morpholin-4-ylcarbonyl)quinazolin-4-yl]amino}cyclohexyl)guanidine bis(trifluoroacetate)

Positive ion FAB-MS m/z: 412[M+H]$^+$

EXAMPLE 176

4-[((1RS,2SR)-2-{[amino(imino)methyl]amino}cyclohexyl)amino]-6-methyl-N-1-naphthylquinazoline-2-carboxamide bis(trifluoroacetate)

Positive ion FAB-MS m/z: 468[M+H]$^+$

EXAMPLE 177

N-1-adamanthyl-4-[((1RS,2SR)-2-{[amino(imino)methyl]amino}cyclohexyl)amino]-6-methylquinazoline-2-carboxamide bis(trifluoroacetate)

Positive ion FAB-MS m/z: 476[M+H]$^+$

EXAMPLE 178

4-[(((1RS,2SR)-2-{[amino(imino)methyl]amino}cyclohexyl)amino]-N-2,3-dihydro-1,4-benzodioxan-6-yl-6-methylquinazoline-2-carboxamide bis(trifluoroacetate)

Positive ion FAB-MS m/z: 476[M+H]$^+$

EXAMPLE 179

N-[(1RS,2SR)-2-({2-[(4-benzylpiperazin-1-yl)carbonyl]-6-methylquinazolin-4-yl}amino)cyclohexyl]guanidine tris(trifluoroacetate)

Positive ion FAB-MS m/z: 501[M+H]$^+$

EXAMPLE 180

4-[((1RS,2SR)-2-{[amino(imino)methyl]amino}cyclohexyl)amino]-N-(1-benzylpiperidin-4-yl)-6-methylquinazoline-2-carboxamide tris(trifluoroacetate)

Positive ion FAB-MS m/z: 515[M+H]$^+$

EXAMPLE 181

4-[((1RS,2SR)-2-{[amino(imino)methyl]amino}cyclohexyl)amino]-N-(cyclohexylmethyl)-6-methylquinazoline-2-carboxamide bis(trifluoroacetate)

Positive ion FAB-MS m/z: 438[M+H]$^+$

EXAMPLE 182

N-((1RS,2SR)-2-{[2-(1,2,3,4-tetrahydroisoquinolin-2-ylcarbonyl)-6-methylquinazolin-4-yl]amino}cyclohexyl)guanidine bis(trifluoroacetate)

Positive ion FAB-MS m/z: 458[M+H]$^+$

EXAMPLE 183

4-[((1RS,2SR)-2-{[amino(imino)methyl]amino}cyclohexyl)amino]-6-methyl-N-neopentylquinazoline-2-carboxamide bis(trifluoroacetate)

Positive ion FAB-MS m/z: 412[M+H]$^+$

EXAMPLE 184

N-((1RS,2SR)-2-{[2-(2,3-dihydro-1H-indol-1-ylcarbonyl)-6-methylquinazolin-4-yl]amino}cyclohexyl)guanidine bis(trifluoroacetate)

Positive ion FAB-MS m/z: 444[M+H]$^+$

EXAMPLE 185

4-[((1RS,2SR)-2-{[amino(imino)methyl]amino}cyclohexyl)amino]-N-cyclopropyl-6-methylquinazoline-2-carboxamide bis(trifluoroacetatee)

Positive ion FAB-MS m/z: 382[M+H]$^+$

EXAMPLE 186

4-[((1RS,2SR)-2-{[amino(imino)methyl]amino}cyclohexyl)amino]-N-1,3-benzothiazol-2-yl-6-methylquinazoline-2-carboxamide bis(trifluoroacetate)

Positive ion FAB-MS m/z: 475[M+H]$^+$

EXAMPLE 187

4-[((1RS,2SR)-2-{[amino(imino)methyl]amino}cyclohexyl)amino]-N-[2-(benzylthio)ethyl]-6-methylquinazoline-2-carboxamide bis(trifluoroacetate)

Positive ion FAB-MS m/z: 492[M+H]$^+$

EXAMPLE 188

4-[((1RS,2SR)-2-{[amino(imino)methyl]amino}cyclohexyl)amino]-N-1-azabicyclo[2.2.2]oct-3-yl-6-methylquinazoline-2-carboxamide tris(trifluoroacetate)

Positive ion FAB-MS m/z: 451[M+H]$^+$

EXAMPLE 189

4-[((1RS,2SR)-2-{[amino(imino)methyl]amino}cyclohexyl)amino]-N-(1,2-diphenylethyl)-6-methylquinazoline-2-carboxamide bis(trifluoroacetate)

Positive ion FAB-MS m/z: 522[M+H]$^+$

EXAMPLE 190

N-((1RS,2SR)-2-{[6-methyl-2-(decahydroquinolin-1-ylcarbonyl)quinazolin-4-yl]amino}cyclohexyl)guanidine bis(trifluoroacetate)

Positive ion FAB-MS m/z: 464[M+H]$^+$

EXAMPLE 191

4-[((1RS,2SR)-2-{[amino(imino)methyl]amino}cyclohexyl)amino]-6-methyl-N-(1-naphthylmethyl)quinazoline-2-carboxamide bis(trifluoroacetate)

Positive ion FAB-MS m/z: 482[M+H]$^+$

EXAMPLE 192

N-((1RS,2SR)-2-{[6-methyl-2-(1,3-thiazolidin-3-ylcarbonyl)quinazolin-4-yl]amino}cyclohexyl)guanidine bis(trifluoroacetate)

Positive ion FAB-MS m/z: 414[M+H]$^+$

EXAMPLE 193

4-[((1RS,2SR)-2-{[amino(imino)methyl]amino}cyclohexyl)amino]-N-(2,4-difluorobenzyl)-6-methylquinazoline-2-carboxamide bis(trifluoroacetate)

Positive ion FAB-MS m/z: 468[M+H]$^+$

EXAMPLE 194

N-{(1RS,2SR)-2-[(2-{[4-(1,3-benzodioxol-5-ylmethyl)piperazin-1-yl]carbonyl}-6-methylquinazolin-4-yl)amino]cyclohexyl}guanidine tris(trifluoroacetate)

Positive ion FAB-MS m/z: 545[M+H]$^+$

EXAMPLE 195

4-[((1RS,2SR)-2-{[amino(imino)methyl]amino}cyclohexyl)amino]-N-[2-(3,4-dimethoxyphenyl)ethyl]-6-methylquinazoline-2-carboxamide bis(trifluoroacetate)

Positive ion FAB-MS m/z: 506[M+H]$^+$

EXAMPLE 196

4-[((1RS,2SR)-2-{[amino(imino)methyl]amino}cyclohexyl)amino]-6-methyl-N-(3-(2-methylpiperidin-1-yl)propyl)quinazoline-2-carboxamide tris(trifluoroacetate)

Positive ion FAB-MS m/z: 481[M+H]$^+$

EXAMPLE 197

4-[((1RS,2SR)-2-{[amino(imino)methyl]amino}cyclohexyl)amino]-6-methyl-N-(2-(pyridin-2-yl)ethyl)quinazoline-2-carboxamide tris(trifluoroacetate)

Positive ion FAB-MS m/z: 447[M+H]$^+$

EXAMPLE 198

N-((1RS,2SR)-2-{[6-methyl-2-([4-[(2E)-3-phenyl-2-propenyl]piperazin-1-yl]carbonyl)quinazolin-4-yl]amino}cyclohexyl)guanidine tris(trifluoroacetate)

Positive ion FAB-MS m/z: 527[M+H]$^+$

EXAMPLE 199

4-[((1RS,2SR)-2-{[amino(imino)methyl]amino}cyclohexyl)amino]-6-methyl-N-{3-[methyl(phenyl)amino]propyl}quinazoline-2-carboxamide tris(trifluoroacetate)

Positive ion FAB-MS m/z: 489[M+H]$^+$

EXAMPLE 200

4-[((1RS,2SR)-2-{[amino(imino)methyl]amino}cyclohexyl)amino]-N-(3-methoxyphenyl)-6-methylquinazoline-2-carboxamide bis(trifluoroacetate)

Positive ion FAB-MS m/z: 448[M+H]$^+$

EXAMPLE 201

4-[((1RS,2SR)-2-{[amino(imino)methyl]amino}cyclohexyl)amino]-6-methyl-N-(pyridin-3-yl)quinazoline-2-carboxamide tris(trifluoroacetate)

Positive ion FAB-MS m/z: 419[M+H]$^+$

EXAMPLE 202

4-[((1RS,2SR)-2-{[amino(imino)methyl]amino}cyclohexyl)amino]-6-methyl-N-(2-(morpholin-4-yl)ethyl)quinazoline-2-carboxamide tris(trifluoroacetate)

Positive ion FAB-MS m/z: 455[M+H]$^+$

EXAMPLE 203

4-[((1RS,2SR)-2-{[amino(imino)methyl]amino}cyclohexyl)amino]-N-2,3-dihydro-1H-inden-5-yl-6-methylquinazoline-2-carboxamide bis(trifluoroacetate)

Positive ion FAB-MS m/z: 458[M+H]$^+$

EXAMPLE 204

4-[((1RS,2SR)-2-{[amino(imino)methyl]amino}cyclohexyl)amino]-6-methyl-N-(3-phenoxyphenyl)quinazoline-2-carboxamide bis(trifluoroacetate)

Positive ion FAB-MS m/z: 510[M+H]$^+$

EXAMPLE 205

N-((1RS,2SR)-2-{[2-(1,4'-bipiperidin-1'-ylcarbonyl)-6-methylquinazolin-4-yl]amino}cyclohexyl)guanidine tris(trifluoroacetate)

Positive ion FAB-MS m/z: 493[M+H]$^+$

EXAMPLE 206

4-[((1RS,2SR)-2-{[amino(imino)methyl]amino}cyclohexyl)amino]-N-cyclohexyl-N,6-dimethylquinazoline-2-carboxamide bis(trifluoroacetate)

Positive ion FAB-MS m/z: 438[M+H]$^+$

EXAMPLE 207

4-[((1RS,2SR)-2-{[amino(imino)methyl]amino}cyclohexyl)amino]-6-methyl-N-(tetrahydrofuran-2-ylmethyl)quinazoline-2-carboxamide bis(trifluoroacetate)

Positive ion FAB-MS m/z: 426[M+H]$^+$

EXAMPLE 208

4-[((1RS,2SR)-2-{[amino(imino)methyl]amino}cyclohexyl)amino]-N-(6-ethoxy-1,3-benzothiazol-2-yl)-6-methylquinazoline-2-carboxamide bis(trifluoroacetate)

Positive ion FAB-MS m/z: 519[M+H]$^+$

EXAMPLE 209

4-[((1RS,2SR)-2-{[amino(imino)methyl]amino}cyclohexyl)amino]-6-methyl-N-(pyridin-2-ylmethyl)quinazoline-2-carboxamide tris(trifluoroacetate)

Positive ion FAB-MS m/z: 433[M+H]$^+$

EXAMPLE 210

4-[((1RS,2SR)-2-{[amino(imino)methyl]amino}cyclohexyl)amino]-N-(3-methoxybenzyl)-6-methylquinazoline-2-carboxamide bis(trifluoroacetate)

Positive ion FAB-MS m/z: 462[M+H]$^+$

EXAMPLE 211

4-[((1RS,2SR)-2-{[amino(imino)methyl]amino}cyclohexyl)amino]-6-methyl-N-(2-phenylethyl)quinazoline-2-carboxamide bis(trifluoroacetate)

Positive ion FAB-MS m/z: 446[M+H]$^+$

EXAMPLE 212

4-[((1RS,2SR)-2-{[amino(imino)methyl]amino}cyclohexyl)amino]-N-[3-(1H-imidazol-1-yl)propyl]-6-methylquinazoline-2-carboxamide bis(trifluoroacetate)

Positive ion FAB-MS m/z: 450[M+H]$^+$

EXAMPLE 213

N-{(1RS,2SR)-2-[(2-{[4-(4-methoxyphenyl)-3-methylpiperazin-1-yl]carbonyl}-6-methylquinazolin-4-yl)amino]cyclohexyl}guanidine tris(trifluoroacetate)

Positive ion FAB-MS m/z: 531[M+H]$^+$

EXAMPLE 214

N-[(1RS,2SR)-2-({6-methyl-2-[(4-(pyrimidin-2-yl)piperazin-1-yl)carbonyl]quinazolin-4-yl}amino)cyclohexyl]guanidine tris(trifluoroacetate)

Positive ion FAB-MS m/z: 489[M+H]$^+$

EXAMPLE 215

N-{(1RS,2SR)-2-[(2-{[(2R,6S)-2,6-dimethylmorpholin-4-yl]carbonyl}-6-methylquinazolin-4-yl)amino]cyclohexyl}guanidine bis(trifluoroacetate)

Positive ion FAB-MS m/z: 440[M+H]$^+$

EXAMPLE 216

N-[(1RS,2SR)-2-({6-methyl-2-[(4-(pyridin-4-yl)piperazin-1-yl)carbonyl]quinazolin-4-yl}amino)cyclohexyl]guanidine tris(trifluoroacetate)

Positive ion FAB-MS m/z: 488[M+H]$^+$

EXAMPLE 217

4-[((1RS,2SR)-2-{[amino(imino)methyl]amino}cyclohexyl)amino]-6-methyl-N-(pyridin-4-ylmethyl)quinazoline-2-carboxamide tris(trifluoroacetate)

Positive ion FAB-MS m/z: 433[M+H]$^+$

EXAMPLE 218

4-[((1RS,2SR)-2-{[amino(imino)methyl]amino}cyclohexyl)amino]-6-methyl-N-(pyridin-3-ylmethyl)quinazoline-2-carboxamide tris(trifluoroacetate)

Positive ion FAB-MS m/z: 433[M+H]$^+$

EXAMPLE 219

4-[((1RS,2SR)-2-{[amino(imino)methyl]amino}cyclohexyl)amino]-N-(1,3-benzodioxol-5-ylmethyl)-6-methylquinazoline-2-carboxamide bis(trifluoroacetate)

Positive ion FAB-MS m/z; 476[M+H]$^+$

EXAMPLE 220

4-[((1RS,2SR)-2-{[amino(imino)methyl]amino}cyclohexyl)amino]-N-(4-benzylphenyl)-6-methylquinazoline-2-carboxamide bis(trifluoroacetate)

Positive ion FAB-MS m/z: 508[M+H]$^+$

EXAMPLE 221

N-((1RS,2SR)-2-{[6-methyl-2-(decahydroquinolin-1-ylcarbonyl)quinazolin-4-yl]amino}cyclohexyl)guanidine bis(trifluoroacetate)

Positive ion FAB-MS m/z: 464[M+H]$^+$

EXAMPLE 222

1-({4-[((1RS,2SR)-2-{[amino(imino)methyl]amino}cyclohexyl)amino]-6-methylquinazolin-2-yl}carbonyl)-N,N-diethylpiperidine-3-carboxamide bis(trifluoroacetate)

Positive ion FAB-MS m/z: 509[M+H]$^+$

EXAMPLE 223

4-[((1RS,2SR)-2-{[amino(imino)methyl]amino}cyclohexyl)amino]-N-[2-(4-methoxyphenyl)ethyl]-6-methylquinazoline-2-carboxamide bis(trifluoroacetate)

Positive ion FAB-MS m/z: 476[M+H]$^+$

EXAMPLE 224

4-[((1RS,2SR)-2-{[amino(imino)methyl]amino}cyclohexyl)amino]-N-[4-(dimethylamino)benzyl]-6-methylquinazoline-2-carboxamide tris(trifluoroacetate)

Positive ion FAB-MS m/z: 475[M+H]$^+$

EXAMPLE 225

N-[(1RS,2SR)-2-({6-methyl-2-[(4-oxo-1-phenyl-1,3,8-triazaspiro[4.5]deca-8-yl)carbonyl]quinazolin-4-yl}amino)cyclohexyl]guanidine bis(trifluoroacetate)

Positive ion FAB-MS m/z: 556[M+H]$^+$

EXAMPLE 226

4-[((1RS,2SR)-2-{[amino(imino)methyl]amino}cyclohexyl)amino]-N-(2-furylmethyl)-6-methylquinazoline-2-carboxamide bis(trifluoroacetate)

Positive ion FAB-MS m/z: 422[M+H]$^+$

EXAMPLE 227

4-[((1RS,2SR)-2-{[amino(imino)methyl]amino}cyclohexyl)amino]-6-methyl-N-(3,4,5-trimethoxybenzyl)quinazoline-2-carboxamide bis(trifluoroacetate)

Positive ion FAB-MS m/z: 522[M+H]$^+$

EXAMPLE 228

4-{[({4-[((1RS,2SR)-2-{[amino(imino)methyl]amino}cyclohexyl)amino]-6-methylquinazolin-2-yl}carbonyl)amino]methyl}benzoic acid methyl ester bis(trifluoroacetate)

Positive ion FAB-MS m/z: 490[M+H]$^+$

EXAMPLE 229

N-[(1RS,2SR)-2-({6-methyl-2-[(4-(pyrazin-2-yl)piperazin-1-yl)carbonyl]quinazolin-4-yl}amino)cyclohexyl]guanidine tris(trifluoroacetate)

Positive ion FAB-MS m/z: 489[M+H]$^+$

EXAMPLE 230

N-[(1RS,2SR)-2-({6-methyl-2-[(4-(pyridin-2-yl)piperazin-1-yl)carbonyl]quinazolin-4-yl}amino)cyclohexyl]guanidine tris(trifluoroacetate)

Positive ion FAB-MS m/z: 488[M+H]$^+$

EXAMPLE 231

4-[((1RS,2SR)-2-{[amino(imino)methyl]amino}cyclohexyl)amino]-N-[(3R)-1-benzylpyrrolidin-3-yl]-6-methylquinazoline-2-carboxamide tris(trifluoroacetate)

Positive ion FAB-MS m/z: 501[M+H]$^+$

EXAMPLE 232

4-[((1RS,2SR)-2-{[amino(imino)methyl]amino}cyclohexyl)amino]-N-2,3-dihydro-1H-inden-1-yl-6-methylquinazoline-2-carboxamide bis(trifluoroacetate)

Positive ion FAB-MS m/z: 458[M+H]$^+$

EXAMPLE 233

4-[((1RS,2SR)-2-{[amino(imino)methyl]amino}cyclohexyl)amino]-N-[2-(4-fluorophenyl)ethyl]-6-methylquinazoline-2-carboxamide bis(trifluoroacetate)

Positive ion FAB-MS m/z: 464[M+H]$^+$

EXAMPLE 234

4[((1RS,2SR)-2-{[amino(imino)methyl]amino}cyclohexyl)amino]-N-[2-(1-benzylpyrrolidin-3-yl)ethyl]-6-methylquinazoline-2-carboxamide tris(trifluoroacetate)

Positive ion FAB-MS m/z: 529[M+H]$^+$

EXAMPLE 235

4-[((1RS,2SR)-2-{[amino(imino)methyl]amino}cyclohexyl)amino]-N-[2-(1H-indol-3-yl)ethyl]-6-methylquinazoline-2-carboxamide bis(trifluoroacetate)

Positive ion FAB-MS m/z: 485[M+H]$^+$

EXAMPLE 236

4-[((1RS,2SR)-2-{[amino(imino)methyl]amino}cyclohexyl)amino]-6-methyl-N-(1-phenylethyl)quinazoline-2-carboxamide bis(trifluoroacetate)

Positive ion FAB-MS m/z: 446[M+H]$^+$

EXAMPLE 237

(2R)-[({4-[((1RS,2SR)-2-{[(amino(imino)methyl]amino}cyclohexyl)amino]-6-methylquinazolin-2-yl}carbonyl)amino]phenylacetic acid methyl ester bis(trifluroacetate)

Positive ion FAB-MS m/z: 490[M+H]$^+$

EXAMPLE 238

4-[((1RS,2SR)-2-{[amino(imino)methyl]amino}cyclohexyl)amino]-N-[(1S)-1-benzyl-2-methoxyethyl]-6-methylquinazoline-2-carboxamide bis(trifluoroacetate)

Positive ion FAB-MS m/z: 490[M+H]$^+$

EXAMPLE 239

4-[((1RS,2SR)-2-{[amino(imino)methyl]amino}cyclohexyl)amino]-N-(2-chlorobenzyl)-6-methylquinazoline-2-carboxamide bis(trifluoroacetate)

Positive ion FAB-MS m/z; 466[M+H]$^+$

EXAMPLE 240

4-[((1RS,2SR)-2-{[amino(imino)methyl]amino}cyclohexyl)amino]-N-(3,4-difluorobenzyl)-6-methylquinazoline-2-carboxamide bis(trifluoroacetate)

Positive ion FAB-MS m/z: 468[M+H]$^+$

EXAMPLE 241

N-[(1RS,2SR)-2-({6-methyl-2-[(4-phenyl-1,2,5,6-tetrahydropyridin-1-yl)carbonyl]quinazolin-4-yl}amino)cyclohexyl]guanidine bis(trifluoroacetate)

Positive ion FAB-MS m/z: 484[M+H]$^+$

EXAMPLE 242

4-[((1RS,2SR)-2-{[amino(imino)methyl]amino}cyclohexyl)amino]-N-(4-fluorobenzyl)-6-methylquinazoline-2-carboxamide bis(trifluoroacetate)

Positive ion FAB-MS m/z: 450[M+H]$^+$

EXAMPLE 243

4-[((1RS,2SR)-2-{[amino(imino)methyl]amino}cyclohexyl)amino]-N-[(3S)-1-benzylpyrrolidin-3-yl]-6-methylquinazoline-2-carboxamide tris(trifluoroacetate)

Positive ion FAB-MS m/z: 501[M+H]$^+$

EXAMPLE 244

4-[((1RS,2SR)-2-{[(amino(imino)methyl]amino}cyclohexyl)amino]-N-(1-benzylpyrrolidin-3-yl)-N,6-dimethylquinazoline-2-carboxamide tris(trifluoroacetate)

Positive ion FAB-MS m/z: 515[M+H]$^+$

EXAMPLE 245

4-[((1RS,2SR)-2-{[amino(imino)methyl]amino}cyclohexyl)amino]-N-{2-[(2-furylmethyl)thio]ethyl}-6-methylquinazoline-2-carboxamide bis(trifluoroacetate)

Positive ion FAB-MS m/z: 482[M+H]$^+$

EXAMPLE 246

4-[((1RS,2SR)-2-{[amino(imino)methyl]amino}cyclohexyl)amino]-6-methyl-N-[(5-methylpyrazin-2-yl)methyl]quinazoline-2-carboxamide bis(trifluoroacetate)

Positive ion FAB-MS m/z: 448[M+H]$^+$

EXAMPLE 247

1-({4-[((1RS,2SR)-2-{[amino(imino)methyl]amino}cyclohexyl)amino]-6-methylquinazolin-2-yl}carbonyl)piperidine-4-carboxylic acid ethyl ester bis(trifluoroacetate)

Positive ion FAB-MS M/z: 482[M+H]$^+$

EXAMPLE 248

1-({4-[((1RS,2SR)-2-{[amino(imino)methyl]amino}cyclohexyl)amino]-6-methylquinazolin-2-yl}carbonyl)piperidine-4-carboxamide bis(trifluoroacetate)

Positive ion FAB-MS m/z: 453[M+H]$^+$

EXAMPLE 249

4-[((1RS,2SR)-2-{[(amino(imino)methyl]amino}cyclohexyl)amino]-6-methyl-N-1,2,3,4-tetrahydronaphthalen-1-ylquinazoline-2-carboxamide bis(trifluoroacetate)

Positive ion FAB-MS m/z: 472[M+H]$^+$

EXAMPLE 250

4-[((1RS,2SR)-2-{[amino(imino)methyl]amino}cyclohexyl)amino]-6-methyl-N-(tetrahydrofuran-2-ylmethyl)quinazoline-2-carboxamide bis(trifluoroacetate)

Positive ion FAB-MS m/z: 426[M+H]$^+$

EXAMPLE 251

4-[((1RS,2SR)-2-{[amino(imino)methyl]amino}cyclohexyl)amino]-6-methyl-N-[4-(trifluoromethyl)benzyl]quinazoline-2-carboxamide bis(trifluoroacetate)

Positive ion FAB-MS m/z: 500[M+H]$^+$

EXAMPLE 252

4-[((1RS,2SR)-2-{[amino(imino)methyl]amino}cyclohexyl)amino]-6-methyl-N-[4-(trifluoromethoxy)benzyl]quinazoline-2-carboxamide bis(trifluoroacetate)

Positive ion FAB-MS m/z: 516[M+H]$^+$

EXAMPLE 253

4[((1RS,2SR)-2-{[amino(imino)methyl]amino}cyclohexyl)amino]-N-(6-chloropyridin-3-yl)-6-methylquinazoline-2-carboxamide tris(trifluoroacetate)

Positive ion FAB-MS m/z: 453[M+H]$^+$

EXAMPLE 254

N-[1-(1-adamanthyl)ethyl]-4-[((1RS,2SR)-2-{[amino(imino)methyl]amino}cyclohexyl)amino]-6-methylquinazoline-2-carboxamide bis(trifluoroacetate)

Positive ion FAB-MS m/z: 504[M+H]$^+$

EXAMPLE 255

4-[((1RS,2SR)-2-{[amino(imino)methyl]amino}cyclohexyl)amino]-N-[4-(aminomethyl)benzyl]-6-methylquinazoline-2-carboxamide tris(trifluoroacetate)

Positive ion FAB-MS m/z: 461[M+H]$^+$

EXAMPLE 256

4-[((1RS,2SR)-2-{[amino(imino)methyl]amino}cyclohexyl)amino]-N-(3-chlorobenzyl)-6-methylquinazoline-2-carboxamide bis(trifluoroacetate)

Positive ion FAB-MS m/z: 466[M+H]J

EXAMPLE 257

4-[((1RS,2SR)-2-{[amino(imino)methyl]amino}cyclohexyl)amino]-N-(4-chlorobenzyl)-6-methylquinazoline-2-carboxamide bis(trifluoroacetate)

Positive ion FAB-MS m/z: 466[M+H]$^+$

EXAMPLE 258

4-[((1RS,2SR)-2-{[amino(imino)methyl]amino}cyclohexyl)amino]-N-(2-oxo-2-phenylethyl)-6-methylquinazoline-2-carboxamide bis(trifluoroacetate)

Positive ion FAB-MS m/z: 460[M+H]$^+$

EXAMPLE 259

4-[((1RS,2SR)-2-{[amino(imino)methyl]
amino}cyclohexyl)amino]-6-methyl-N-(2-(pyridin-
2-yl)ethyl)quinazoline-2-carboxamide tris(trifluoroacetate)

Positive ion FAB-MS m/z: 447[M+H]$^+$

EXAMPLE 260

4-[((1RS,2SR)-2-{[amino(imino)methyl]
amino}cyclohexyl)amino]-N-{[(2S)-1-ethylpyrrolidin-2-yl]methyl}-6-methylquinazoline-2-carboxamide tris(trifluoroacetate)

Positive ion FAB-MS m/z: 453[M+H]$^+$

EXAMPLE 261

N-[1-({4-[((1RS,2SR)-2-{[amino(imino)methyl]
amino}cyclohexyl)amino]-6-methylquinazolin-2-
yl}carbonyl)pyrrolidin-3-yl]acetamide bis(trifluoroacetate)

Positive ion FAB-MS m/z: 453[M+H]$^+$

EXAMPLE 262

4-[((1RS,2SR)-2-{[amino(imino)methyl]
amino}cyclohexyl)amino]-N-(3-fluorobenzyl)-6-
methylquinazoline-2-carboxamide bis(trifluoroacetate)

Positive ion FAB-MS m/z: 450[M+H]$^+$

EXAMPLE 263

4-[((1RS,2SR)-2-{[amino(imino)methyl]
amino}cyclohexyl)amino]-N-(2-fluorobenzyl)-6-
methylquinazoline-2-carboxamide bis(trifluoroacetate)

Positive ion FAB-MS m/z: 450[M+H]$^+$

EXAMPLE 264

4-[((1RS,2SR)-2-{[amino(imino)methyl]
amino}cyclohexyl)amino]-N-[3-fluoro-5-(trifluoromethyl)benzyl]-6-methylquinazoline-2-carboxamide bis(trifluoroacetate)

Positive ion FAB-MS m/z; 518[M+H]$^+$

EXAMPLE 265

N-[(1RS,2SR)-2-({2-[(4-benzylpiperidin-1-yl)carbonyl]-6-methylquinazolin-4-yl}amino)cyclohexyl]
guanidine bis(trifluoroacetate)

Positive ion FAB-MS m/z: 500[M+H]$^+$

EXAMPLE 266

4-[((1RS,2SR)-2-{[amino(imino)methyl]
amino}cyclohexyl)amino]-N-{2-[4-(aminosulfonyl)
phenyl]ethyl}-6-methylquinazoline-2-carboxamide
bis(trifluoroacetate)

Positive ion FAB-MS m/z: 525[M+H]$^+$

EXAMPLE 267

4-[((1RS,2SR)-2-{[amino(imino)methyl]
amino}cyclohexyl)amino]-N-[2-(1,3-benzodioxol-5-
yl)ethyl]-6-methylquinazoline-2-carboxamide bis
(trifluoroacetate)

Positive ion FAB-MS m/z: 490[M+H]$^+$

EXAMPLE 268

N-[(1RS,2SR)-2-({2-[(6,7-dimethoxy-1,2,3,4-tetrahydroisoquinolin-2-yl)carbonyl]-6-methylquinazolin-4-yl}amino)cyclohexyl]guanidine bis(trifluoroacetate)

Positive ion FAB-MS m/z: 518[M+H]$^+$

EXAMPLE 269

4-[((1RS,2SR)-2-{[amino(imino)methyl]
amino}cyclohexyl)amino]-6-methyl-N-[(1R)-1-phenylethyl]quinazoline-2-carboxamide bis(trifluoroacetate)

Positive ion FAB-MS m/z: 446[M+H]$^+$

EXAMPLE 270

N-[(1S,6R)-6-(aminocarbonyl)-3-cyclohexen-1-yl]-
4-[((1RS,2SR)-2-{[amino(imino)methyl]
amino}cyclohexyl)amino]-6-methylquinazoline-2-
carboxamide bis(trifluoroacetate)

Positive ion FAB-MS m/z: 465[M+H]$^+$

EXAMPLE 271

4-[((1RS,2SR)-2-{[amino(imino)methyl]
amino}cyclohexyl)amino]-6-methyl-N-(3-methylbenzyl)quinazoline-2-carboxamide bis(trifluoroacetate)

Positive ion FAB-MS m/z: 446[M+H]$^+$

EXAMPLE 272

N-[(1RS,2SR)-2-({2-[(2,5-dimethyl-2,5-dihydro-1H-
pyrrol-1-yl)carbonyl]-6-methylquinazolin-4-
yl}amino)cyclohexyl]guanidine bis(trifluoroacetate)

Positive ion FAB-MS m/z; 422[M+H]$^+$

EXAMPLE 273

4-[((1RS,2SR)-2-{[amino(imino)methyl]amino}cyclohexyl)amino]-6-methyl-N-(2-phenylpropyl)quinazoline-2-carboxamide bis(trifluoroacetate)

Positive ion FAB-MS m/z: 460[M+H]$^+$

EXAMPLE 274

4-[((1RS,2SR)-2-{[amino(imino)methyl]amino}cyclohexyl)amino]-N,6-dimethyl-N-(2-phenylethyl)quinazoline-2-carboxamide bis(trifluoroacetate)

Positive ion FAB-MS m/z: 460[M+H]$^+$

EXAMPLE 275

4-[((1RS,2SR)-2{-[amino(imino)methyl]amino}cyclohexyl)amino]-N-[2-(2,5-dimethoxyphenyl)ethyl]-6-methylquinazoline-2-carboxamide bis(trifluoroacetate)

Positive ion FAB-MS m/z: 506[M+H]$^+$

EXAMPLE 276

4-[((1RS,2SR)-2-{[amino(imino)methyl]amino}cyclohexyl)amino]-N-[2-(3,4-dimethoxyphenyl)ethyl]-N,6-dimethylquinazoline-2-carboxamide bis(trifluoroacetate)

Positive ion FAB-MS m/z: 520[M+H]$^+$

EXAMPLE 277

4-[((1RS,2SR)-2-{[amino(imino)methyl]amino}cyclohexyl)amino]-N-{2-[benzyl(methyl)amino]ethyl}-N,6-dimethylquinazoline-2-carboxamide tris(trifluoroacetate)

Positive ion FAB-MS m/z; 503 [M+H]$^+$

EXAMPLE 278

4-[((1RS,2SR)-2-{[amino(imino)methyl]amino}cyclohexyl)amino]-6-methyl-N-(thiophen-2-ylmethyl)quinazoline-2-carboxamide bis(trifluoroacetate)

Positive ion FAB-MS m/z: 438[M+H]$^+$

EXAMPLE 279

4-[((1RS,2SR)-2-{[amino(imino)methyl]amino}cyclohexyl)amino]-6-methyl-N-(1-methyl-3-phenylpropyl)quinazoline-2-carboxamide bis(trifluoroacetate)

Positive ion FAB-MS m/z: 474[M+H]$^+$

EXAMPLE 280

4-[((1RS,2SR)-2-{[amino(imino)methyl]amino}cyclohexyl)amino]-N-[2-(3,4-dimethoxyphenyl)ethyl]-6-methylquinazoline-2-carboxamide bis(trifluoroacetate)

Positive ion FAB-MS m/z: 506[M+H]$^+$

EXAMPLE 281

4-[((1RS,2SR)-2-{[amino(imino)methyl]amino}cyclohexyl)amino]-6-methyl-N-[2-(4-methylphenyl)ethyl]quinazoline-2-carboxamide bis(trifluoroacetate)

Positive ion FAB-MS m/z: 460[M+H]$^+$

EXAMPLE 282

4-[((1RS,2SR)-2-{[amino(imino)methyl]amino}cyclohexyl)amino]-N-[2-(2-chlorophenyl)ethyl]-6-methylquinazoline-2-carboxamide bis(trifluoroacetate)

Positive ion FAB-MS m/z: 480[M+H]$^+$

EXAMPLE 283

4-[((1RS,2SR)-2-{[amino(imino)methyl]amino}cyclohexyl)amino]-N-(1,1-diethyl-2-propynyl)-6-methylquinazoline-2-carboxamide bis(trifluoroacetate)

Positive ion FAB-MS m/z: 436[M+H]$^+$

EXAMPLE 284

4-[((1RS,2SR)-2-{[amino(imino)methyl]amino}cyclohexyl)amino]-6-methyl-N-[(1RS,2SR)-2-phenylcyclopropyl]quinazoline-2-carboxamide bis(trifluoroacetate)

Positive ion FAB-MS m/z: 458[M+H]$^+$

EXAMPLE 285

4-[((1RS,2SR)-2-{[amino(imino)methyl]amino}cyclohexyl)amino]-6-methyl-N-(2-methylbutyl)quinazoline-2-carboxamide bis(trifluoroacetate)

Positive ion FAB-MS m/z: 412[M+H]$^+$

EXAMPLE 286

N-({4-[((1RS,2SR)-2-{[amino(imino)methyl]amino}cyclohexyl)amino]-6-methylquinazolin-2-yl}carbonyl)-beta-alanine ethyl ester bis(trifluoroacetate)

Positive ion FAB-MS m/z: 442[M+H]$^+$

EXAMPLE 287

N-({4-[((1RS,2SR)-2-{[amino(imino)methyl]amino}cyclohexyl)amino-6-methylquinazolin-2-yl}carbonyl)-L-phenylalanine bis(trifluoroacetate)

Positive ion FAB-MS m/z: 490[M+H]$^+$

EXAMPLE 288

4-[((1RS,2SR)-2-{[amino(imino)methyl]amino}cyclohexyl)amino]-6-methyl-N-(2-methylcyclohexyl)quinazoline-2-carboxamide bis(trifluoroacetate)

Positive ion FAB-MS m/z: 438[M+H]$^+$

EXAMPLE 289

4-[((1RS,2SR)-2-{[amino(imino)methyl]amino}cyclohexyl)amino]-N-[2-(diisopropylamino)ethyl]-6-methylquinazoline-2-carboxamide bis(trifluoroacetate)

Positive ion FAB-MS m/z: 469[M+H]$^+$

EXAMPLE 290

4-[((1RS,2SR)-2-{[amino(imino)methyl]amino}cyclohexyl)amino]-N-[5-(ethylthio)-1,3,4-thiadiazol-2-yl]-6-methylquinazoline-2-carboxamide bis(trifluoroacetate)

Positive ion FAB-MS m/z: 486[M+H]$^+$

EXAMPLE 291

4-[((1RS,2SR)-2-{[amino(imino)methyl]amino}cyclohexyl)amino]-N-(3-n-butoxypropyl)-6-methylquinazoline-2-carboxamide bis(trifluoroacetate)

Positive ion FAB-MS m/z: 456[M+H]$^+$

EXAMPLE 292

4-[((1RS,2SR)-2-{[amino(imino)methyl]amino}cyclohexyl)amino]-N-(2-ethoxyethyl)-6-methylquinazoline-2-carboxamide bis(trifluoroacetate)

Positive ion FAB-MS m/z: 414[M+H]$^+$

EXAMPLE 293

N-{(1RS,2SR)-2-[(6-methyl-2-{[(1S,2SR)-1,3,3-trimethyl-6-azabicyclo[3.2.1]oct-6-yl]carbonyl}quinazolin-4-yl)amino]cyclohexyl}guanidine bis(trifluoroacetate)

Positive ion FAB-MS m/z: 478[M+H]$^+$

EXAMPLE 294

4-[((1RS,2SR)-2-{[amino(imino)methyl]amino}cyclohexyl)amino]-6-methyl-N-(1,7,7-trimethylbicyclo[2.2.1]hept-2-yl)quinazoline-2-carboxamide bis(trifluoroacetate)

Positive ion FAB-MS m/z: 478[M+H]$^+$

EXAMPLE 295

4-[((1RS,2SR)-2-{[amino(imino)methyl]amino}cyclohexyl)amino]-N-[2-(ethylthio)ethyl]-6-methylquinazoline-2-carboxamide bis(trifluoroacetate)

Positive ion FAB-MS m/z: 430[M+H]$^+$

EXAMPLE 296

4-[((1RS,2SR)-2-{[amino(imino)methyl]amino}cyclohexyl)amino]-N-benzhydryl-6-methylquinazoline-2-carboxamide bis(trifluoroacetate)

Positive ion FAB-MS m/z: 508[M+H]$^+$

EXAMPLE 297

4-[((1RS,2SR)-2-{[amino(imino)methyl]amino}cyclohexyl)amino]-N-bicyclo[2.2.1]hept-2-yl-6-methylquinazoline-2-carboxamide bis(trifluoroacetate)

Positive ion FAB-MS m/z: 436[M+H]$^+$

EXAMPLE 298

(1R,2R)-2-[({4-[((1RS,2SR)-2-{[amino(imino)methyl]amino}cyclohexyl)amino]-6-methylquinazolin-2-yl}carbonyl)amino]cyclohexanecarboxylic acid ethyl ester bis(trifluoroacetate)

Positive ion FAB-MS m/z: 496[M+H]$^+$

EXAMPLE 299

4-[((1RS,2SR)-2-{[amino(imino)methyl]amino}cyclohexyl)amino]-N-(1-ethynylcyclohexyl)-6-methylquinazoline-2-carboxamide bis(trifluoroacetate)

Positive ion FAB-MS m/z: 448[M+H]$^+$

EXAMPLE 300

4-[((1RS,2SR)-2-{[amino(imino)methyl]amino}cyclohexyl)amino]-N-(1-ethylpropyl)-6-methylquinazoline-2-carboxamide bis(trifluoroacetate)

Positive ion FAB-MS t/z: 412[M+H]$^+$

EXAMPLE 301

4-[((1RS,2SR)-2-{[amino(imino)methyl]amino}cyclohexyl)amino]-6-methyl-N-[2-(2-phenoxyphenyl)ethyl]quinazoline-2-carboxamide bis(trifluoroacetate)

Positive ion FAB-MS m/z: 538[M+H]$^+$

EXAMPLE 302

4-[((1RS,2SR)-2-{[amino(imino)methyl]amino}cyclohexyl)amino]-N-[2-(1,1'-biphenyl-4-yl)ethyl]-6-methylquinazoline-2-carboxamide bis(trifluoroacetate)

Positive ion FAB-MS m/z: 522[M+H]$^+$

EXAMPLE 303

N-({4-[((1RS,2SR)-2-{[amino(imino)methyl]amino}cyclohexyl)amino]-6-methylquinazolin-2-yl}carbonyl)isoleucine methyl ester bis(trifluoroacetate)

Positive ion FAB-MS m/z: 470[M+H]$^+$

EXAMPLE 304

4-[((1RS,2SR)-2-{[amino(imino)methyl]amino}cyclohexyl)amino]-N-[1-(4-fluorophenyl)ethyl]-6-methylquinazoline-2-carboxamide bis(trifluoroacetate)

Positive ion FAB-MS m/z: 464[M+H]$^+$

EXAMPLE 305

4-[((1RS,2SR)-2-{[amino(imino)methyl]amino}cyclohexyl)amino]-6-methyl-N-[1-(2-naphthyl)ethyl]quinazoline-2-carboxamide bis(trifluoroacetate)

Positive ion FAB-MS m/z: 496[M+H]$^+$

EXAMPLE 306

N-({4-[((1RS,2SR)-2-{[amino(imino)methyl]amino}cyclohexyl)amino]-6-methylquinazolin-2-yl}carbonyl)leucine ethyl ester bis(trifluoroacetate)

Positive ion FAB-MS m/z: 484[M+H]$^+$

EXAMPLE 307

{2-[({4-[((1RS,2SR)-2-{[amino(imino)methyl]amino}cyclohexyl)amino]-6-methylquinazolin-2-yl}carbonyl)amino]-1,3-thiazol-4-yl}acetic acid ethyl ester bis(trifluoroacetate)

Positive ion FAB-MS m/z: 511[M+H]$^+$

EXAMPLE 308

4-[((1RS,2SR)-2-{[amino(imino)methyl]amino}cyclohexyl)amino]-6-methyl-N-(4-phenylbutyl)quinazoline-2-carboxamide bis(trifluoroacetate)

Positive ion FAB-MS m/z: 474[M+H]$^+$

EXAMPLE 309

4-[((1RS,2SR)-2-{[amino(imino)methyl]amino}cyclohexyl)amino]-N-(1,3-dimethylbutyl)-6-methylquinazoline-2-carboxamide bis(trifluoroacetate)

Positive ion FAB-MS m/z; 426[M+H]$^+$

EXAMPLE 310

4-[((1RS,2SR)-2-{[amino(imino)methyl]amino}cyclohexyl)amino]-6-methyl-N-(1,2,2-trimethylpropyl)quinazoline-2-carboxamide bis(trifluoroacetate)

Positive ion FAB-MS m/z: 426[M+H]$^+$

EXAMPLE 311

4-[((1RS,2SR)-2-{[amino(imino)methyl]amino}cyclohexyl)amino]-6-methyl-N-(1,1,3,3-tetramethylbutyl)quinazoline-2-carboxamide bis(trifluoroacetate)

Positive ion FAB-MS m/z: 454[M+H]$^+$

EXAMPLE 312

4-[((1RS,2SR)-2-{[amino(imino)methyl]amino}cyclohexyl)amino]-6-methyl-N-(3,3,5-trimethylcyclohexyl)quinazoline-2-carboxamide bis(trifluoroacetate)

Positive ion FAB-MS m/z; 466[M+H]$^+$

EXAMPLE 313

4-[((1RS,2SR)-2-{[amino(imino)methyl]amino}cyclohexyl)amino]-N-(2,3-dimethylcyclohexyl)-6-methylquinazoline-2-carboxamide bis(trifluoroacetate)

Positive ion FAB-MS m/z: 452[M+H]$^+$

EXAMPLE 314

N-({4-[((1RS,2SR)-2-{[amino(imino)methyl]amino}cyclohexyl)amino]6-6-methylquinazolin-2-yl}carbonyl)-L-phenylalanine methyl ester bis(trifluoroacetate)

Positive ion FAB-MS m/z: 504[M+H]$^+$

EXAMPLE 315

4-[((1RS,2SR)-2-{[amino(imino)methyl]amino}cyclohexyl)amino]-6-methyl-N-n-propylquinazoline-2-carboxamide bis(trifluoroacetate)

Positive ion FAB-MS m/z; 384[M+H]$^+$

EXAMPLE 316

4-[((1RS,2SR)-2-{[amino(imino)methyl]amino}cyclohexyl)amino]-N-isopropyl-6-methylquinazoline-2-carboxamide bis(trifluoroacetate)

Positive ion FAB-MS m/z: 384[M+H]$^+$

EXAMPLE 317

4-[((1RS,2SR)-2-{[amino(imino)methyl]amino}cyclohexyl)amino]-N-(2-ethylhexyl)-6-methylquinazoline-2-carboxamide bis(trifluoroacetate)

Positive ion FAB-MS m/z: 454[M+H]$^+$

EXAMPLE 318

4-[((1RS,2SR)-2-{[amino(imino)methyl]amino}cyclohexyl)amino]-N-(3,3-dimethylbutyl)-6-methylquinazoline-2-carboxamide bis(trifluoroacetate)

Positive ion FAB-MS m/z: 426[M+H]$^+$

EXAMPLE 319

4-[((1RS,2SR)-2-{[amino(imino)methyl]amino}cyclohexyl)amino]-N-[2-(4-fluorophenyl)-1,1-dimethylethyl]-6-methylquinazoline-2-carboxamide bis(trifluoroacetate)

Positive ion FAB-MS m/z: 492[M+H]$^+$

EXAMPLE 320

4-[((1RS,2SR)-2-{[amino(imino)methyl]amino}cyclohexyl)amino]-6-methyl-N-(5-nitro-1,3-thiazol-2-yl)quinazoline-2-carboxamide bis(trifluoroacetate)

Positive ion FAB-MS m/z: 470[M+H]$^+$

EXAMPLE 321

4-[((1RS,2SR)-2-{[amino(imino)methyl]amino}cyclohexyl)amino]-N-[3,5-bis(trifluoromethyl)benzyl]-6-methylquinazoline-2-carboxamide bis(trifluoroacetate)

Positive ion FAB-MS m/z: 568[M+H]$^+$

EXAMPLE 322

4-[((1RS,2SR)-2-{[amino(imino)methyl]amino}cyclohexyl)amino]-N-(1,5-dimethylhexyl)-6-methylquinazoline-2-carboxamide bis(trifluoroacetate)

Positive ion FAB-MS m/z: 454[M+H]$^+$

EXAMPLE 323

4-[((1RS,2SR)-2-{[amino(imino)methyl]amino}cyclohexyl)amino]-6-methyl-N-(1-methylheptyl)quinazoline-2-carboxamide bis(trifluoroacetate)

Positive ion FAB-MS m/z: 454[M+H]$^+$

EXAMPLE 324

4-[((1RS,2SR)-2-{[amino(imino)methyl]amino}cyclohexyl)amino]-6-methyl-N-(1-methylhexyl)quinazoline-2-carboxamide bis(trifluoroacetate)

Positive ion FAB-MS m/z: 440[M+H]$^+$

EXAMPLE 325

4-[((1RS,2SR)-2-{[amino(imino)methyl]amino}cyclohexyl)amino]-6-methyl-N-(1-propylbutyl)quinazoline-2-carboxamide bis(trifluoroacetate)

Positive ion FAB-MS m/z: 440[M+H]$^+$

EXAMPLE 326

4-[((1RS,2SR)-2-{[amino(imino)methyl]amino}cyclohexyl)amino]-N-butyl-6-methylquinazoline-2-carboxamide bis(trifluoroacetate)

Positive ion FAB-MS m/z: 398[M+H]$^+$

EXAMPLE 327

4-[((1RS,2SR)-2-{[amino(imino)methyl]amino}cyclohexyl)amino]-N-[2-(3,4-dichlorophenyl)ethyl]-6-methylquinazoline-2-carboxamide bis(trifluoroacetate)

Positive ion FAB-MS m/z: 514[M+H]$^+$

EXAMPLE 328

4-[((1RS,2SR)-2-{[amino (imino)methyl]amino}cyclohexyl)amino]-6-methyl-N-[2-(2-methylphenyl)ethyl]quinazoline-2-carboxamide bis(trifluoroacetate)

Positive ion FAB-MS m/z: 460[M+H]$^+$

EXAMPLE 329

4-[((1RS,2SR)-2-{[amino(imino)methyl]amino}cyclohexyl)amino]-6-methyl-N-(3-(morpholin-4-yl)propyl)quinazoline-2-carboxamide bis(trifluoroacetate)

Positive ion FAB-MS m/z: 469[M+H]$^+$

EXAMPLE 330

4-[((1RS,2SR)-2-{[amino(imino)methyl]amino}cyclohexyl)amino]-N-(3,5-di-tert-butylphenyl)-6-methylquinazoline-2-carboxamide bis(trifluoroacetate)

Positive ion FAB-MS m/z: 530[M+H]$^+$

EXAMPLE 331

4-[((1RS,2SR)-2-{[amino(imino)methyl]amino}cyclohexyl)amino]-6-methyl-N-(4-methylbenzyl)quinazoline-2-carboxamide bis(trifluoroacetate)

Positive ion FAB-MS m/z: 446[M+H]$^+$

EXAMPLE 332

4-[((1RS,2SR)-2-{[(amino(imino)methyl]amino}cyclohexyl)amino]-N-(3,4-dichlorobenzyl)-6-methylquinazoline-2-carboxamide bis(trifluoroacetate)

Positive ion FAB-MS m/z: 500[M+H]$^+$

EXAMPLE 333

4-[((1RS,2SR)-2-{[amino(imino)methyl]amino}cyclohexyl)amino]-6-methyl-N-[(1S)-1-(4-methylphenyl)ethyl]quinazoline-2-carboxamide bis(trifluoroacetate)

Positive ion FAB-MS m/z: 460[M+H]$^+$

EXAMPLE 334

4-[((1RS,2SR)-2-{[amino(imino)methyl]amino}cyclohexyl)amino]-6-methyl-N-(2-methylbenzyl)quinazoline-2-carboxamide bis(trifluoroacetate)

Positive ion FAB-MS m/z: 446[M+H]$^+$

EXAMPLE 335

4-[((1RS,2SR)-2-{[amino(imino)methyl]amino}cyclohexyl)amino]-N-(6-methoxypyridin-3-yl)-6-methylquinazoline-2-carboxamide tris(trifluoroacetate)

Positive ion FAB-MS m/z: 449[M+H]$^+$

EXAMPLE 336

4-[((1RS,2SR)-2-{[amino(imino)methyl]amino}cyclohexyl)amino]-6-methyl-N-2-propynylquinazoline-2-carboxamide bis(trifluoroacetate)

Positive ion FAB-MS m/z: 380[M+H]$^+$

EXAMPLE 337

4-[((1RS,2SR)-2-{[amino(imino)methyl]amino}cyclohexyl)amino]-N-(2,6-difluorobenzyl)-6-methylquinazoline-2-carboxamide bis(trifluoroacetate)

Positive ion FAB-MS m/z: 468[M+H]$^+$

EXAMPLE 338

4-[((1RS,2SR)-2-{[amino(imino)methyl]amino}cyclohexyl)amino]-6-methyl-N-[3-(4-methylpiperazin-1-yl)propyl]quinazoline-2-carboxamide bis(trifluoroacetate)

Positive ion FAB-MS m/z: 482[M+H]$^+$

EXAMPLE 339

4-[((1RS,2SR)-2-{[amino(imino)methyl]amino}cyclohexyl)amino]-6-methyl-N-(2,2,2-trifluoroethyl)quinazoline-2-carboxamide bis(trifluoroacetate)

Positive ion FAB-MS m/z: 424[M+H]$^+$

EXAMPLE 340

N-({4-[((1RS,2SR)-2-{[amino(imino)methyl]amino}cyclohexyl)amino]-6-methylquinazolin-2-yl}carbonyl)glycine ethyl ester bis(trifluoroacetate)

Positive ion FAB-MS m/z: 428[M+H]$^+$

EXAMPLE 341

4-[((1RS,2SR)-2-{[(amino(imino)methyl]amino}cyclohexyl)amino]-N-(3,4-dimethoxyphenyl)-6-methylquinazoline-2-carboxamide bis(trifluoroacetate)

Positive ion FAB-MS m/z: 478[M+H]$^+$

EXAMPLE 342

4-[((1S,2R)-2-{[amino(imino)methyl]amino}cyclohexyl)amino]-N-(2-isopropoxyethyl)-6-methylquinazoline-2-carboxamide dihydrochloride Positive ion FAB-MS m/z: 428[M+H]$^+$

EXAMPLE 343

4-[((1S,2R)-2-{[amino(imino)methyl]amino}cyclohexyl)amino]-N-n-butyl-6-methylquinazoline-2-carboxamide dihydrochloride Positive ion FAB-MS m/z: 398[M+H]$^+$

EXAMPLE 344

4-[((1S,2R)-2-{[amino(imino)methyl]amino}cyclohexyl)amino]-6-methyl-N-(1-methyl-1-phenylethyl)quinazoline-2-carboxamide dihydrochloride Positive ion FAB-MS m/z: 460[M+H]$^+$

EXAMPLE 345

4-[((1S,2R)-2-{[amino(imino)methyl]amino}cyclohexyl)amino]-N-(4-methoxyphenyl)-8-methylquinazoline-2-carboxamide dihydrochloride Positive ion FAB-MS m/z; 448 [M+H]$^+$

EXAMPLE 346

4-[((1S,2R)-2-{[amino(imino)methyl]amino}cyclohexyl)amino]-N-(3-methoxypropyl)-6-methylquinazoline-2-carboxamide dihydrochloride Positive ion FAB-MS m/z: 414 [M+H]$^+$

EXAMPLE 347

4-[((1S,2R)-2-{[amino(imino)methyl]amino}cyclohexyl)amino]-N-[1-(methoxymethyl)cyclohexyl]-6-methylquinazoline-2-carboxamide dihydrochloride Positive ion FAB-MS m/z: 468[M+H]$^+$

EXAMPLE 348

4-[((1S,2R)-2-{[amino(imino)methyl]amino}cyclohexyl)amino]-6-methyl-N-(1,1,3,3-tetramethylbutyl)quinazoline-2-carboxamide dihydrochloride Positive ion FAB-MS m/z: 454[M+H]$^+$

EXAMPLE 349

4-[((1S,2R)-2-{[amino(imino)methyl]amino}cyclohexyl)amino]-6-methyl-N-(2-oxo-2,3-dihydro-1H-benzimidazol-5-yl)quinazoline-2-carboxamide dihydrochloride Positive ion FAB-MS m/z: 474[M+H]$^+$

EXAMPLE 350

4-[((1S,2R)-2-{[amino(imino)methyl]amino}cyclohexyl)amino]-N,N,6-trimethylquinazoline-2-carboxamide dihydrochloride Positive ion FAB-MS m/z; 370[M+H]J+

EXAMPLE 351

4-[((1S,2R)-2-{[amino(imino)methyl]amino}cyclohexyl)amino]-N-(1,1-dimethylpropyl)-6-methylquinazoline-2-carboxamide dihydrochloride Positive ion FAB-MS m/z: 412[M+H]$^+$

EXAMPLE 352

4-[((1S,2R)-2-{[amino(imino)methyl]amino}cyclohexyl)amino]-N-[2-(4-methoxyphenyl)ethyl]-6-methylquinazoline-2-carboxamide dihydrochloride Positive ion FA-MS m/z: 476[M+H]$^+$

EXAMPLE 353

4-[((1S,2R)-2-{[amino(imino)methyl]amino}cyclohexyl)amino]-6-methyl-N-(2-(pyridin-2-yl)ethyl)quinazoline-2-carboxamide trihydrochloride Positive ion FAB-MS t/z: 447[M+H]$^+$

EXAMPLE 354

4-[((1S,2R)-2-{[amino(imino)methyl]amino}cyclohexyl)amino]-6-methyl-N-(2-(morpholin-4-yl)ethyl)quinazoline-2-carboxamide trihydrochloride Positive ion FAB-MS m/z: 455[M+H]$^+$

EXAMPLE 355

4-[((1S,2R)-2-{[amino(imino)methyl]amino}cyclohexyl)amino]-6-methyl-N-n-pentylquinazoline-2-carboxamide dihydrochloride Positive ion FAB-MS m/z: 412[M+H]$^+$

EXAMPLE 356

4-[((1S,2R)-2-{[amino(imino)methyl]amino}cyclohexyl)amino]-N-n-hexyl-6-methylquinazoline-2-carboxamide dihydrochloride Positive ion FAB-MS m/z: 426[M+H]$^+$

EXAMPLE 357

4-[((1S,2R)-2-{[amino(imino)methyl]amino}cyclohexyl)amino]-N-cyclopentyl-6-methylquinazoline-2-carboxamide dihydrochloride Positive ion FAB-MS m/z: 410[M+H]$^+$

EXAMPLE 358

4-[((1S,2R)-2-{[amino(imino)methyl]amino}cyclohexyl)amino]-6-methyl-N-(3-methylbutyl)quinazoline-2-carboxamide dihydrochloride Positive ion FAB-MS m/z: 412[M+H]$^+$

EXAMPLE 359

4-[((1RS,2SR)-2-{[amino(imino)methyl]amino}cyclohexyl)amino]-6-methyl-N-[3-(methylthio)propyl]quinazoline-2-carboxamide dihydrochloride Positive ion FAB-MS m/z: 430[M+H]$^+$

EXAMPLE 360

4-[((1S,2R)-2-{[amino(imino)methyl]amino}cyclohexyl)amino]-6-methyl-N-(5-methyl-1,3-thiazol-2-yl)quinazoline-2-carboxamide trihydrochloride Positive ion FAB-MS m/z: 439[M+H]$^+$

EXAMPLE 361

4-[((1S,2R)-2-{[amino(imino)methyl]amino}cyclohexyl)amino]-6-methyl-N-[2-(2-thienyl)ethyl]quinazoline-2-carboxamide dihydrochloride Positive ion FAB-MS m/z: 452[M+H]$^+$

EXAMPLE 362

4-[((1S,2R)-2-{[amino(imino)methyl]amino}cyclohexyl)amino]-N-[(1S,2S)-2-methoxycyclohexyl]-6-methylquinazoline-2-carboxamide dihydrochloride Positive ion FAB-MS m/z: 454[M+H]$^+$

EXAMPLE 363

4-[((1S,2R)-2-{[amino(imino)methyl]amino}cyclohexyl)amino]-N-[(1R,2R)-2-methoxycyclohexyl]-6-methylquinazoline-2-carboxamide dihydrochloride Positive ion FAB-MS m/z: 454[M+H]$^+$

EXAMPLE 364

4-[((1S,2R)-2-{[amino(imino)methyl]amino}cyclohexyl)amino]-N-cycloheptyl-6-methylquinazoline-2-carboxamide dihydrochloride Positive ion FAB-MS m/z: 438[M+H]$^+$

EXAMPLE 365

4-[((1S,2R)-2-{[amino(imino)methyl]amino}cyclohexyl)amino]-N-(2-ethylbutyl)-6-methylquinazoline-2-carboxamide dihydrochloride Positive ion FAB-MS m/z: 426[M+H]$^+$

EXAMPLE 366

4-[((1S,2R)-2-{[amino(imino)methyl]amino}cyclohexyl)amino]-6-methyl-N-quinolin-6-ylquinazoline-2-carboxamide trihydrochloride Positive ion FAB-MS m/z: 469[M+H]$^+$

EXAMPLE 367

4-[((1S,2R)-2-{[amino(imino)methyl]amino}cyclohexyl)amino]-N-(1H-benzimidazol-2-ylmethyl)-6-methylquinazoline-2-carboxamide trihydrochloride Positive ion FAB-MS m/z: 472[M+H]$^+$

EXAMPLE 368

4-[((1S,2R)-2-{[amino(imino)methyl]amino}cyclohexyl)amino]-N-(cyclohexylmethyl)-6-methylquinazoline-2-carboxamide dihydrochloride Positive ion FAB-MS m/z: 438[M+H]$^+$

EXAMPLE 369

4-[((1S,2R)-2-{[amino(imino)methyl]amino}cyclohexyl)amino]-6-methyl-N-[(2S)-2-methylbutyl]quinazoline-2-carboxamide dihydrochloride Positive ion FAB-MS m/z; 412[M+H]$^+$

EXAMPLE 370

4-[((1S,2R)-2-{[amino(imino)methyl]amino}cyclohexyl)amino]-N-(2-cyclohexylethyl)-6-methylquinazoline-2-carboxamide dihydrochloride Positive ion FAB-MS m/z: 452[M+H]$^+$

EXAMPLE 371

4-[((1S,2R)-2-{[amino(imino)methyl]amino}cyclohexyl)amino]-6-methyl-N-(1-n-propylbutyl)quinazoline-2-carboxamide dihydrochloride Positive ion FAB-MS m/z: 440[M+H]$^+$

EXAMPLE 372

4-[((1S,2R)-2-{[amino(imino)methyl]amino}cyclohexyl)amino]-N-(2-ethoxyethyl)-6-methylquinazoline-2-carboxamide dihydrochloride Positive ion FAB-MS m/z: 414[M+H]$^+$

EXAMPLE 373

4-[((1S,2R)-2-{[amino(imino)methyl]amino}cyclohexyl)amino]-N-[2-(2-methoxyphenyl)ethyl]-6-methylquinazoline-2-carboxamide dihydrochloride Positive ion FAB-MS m/z: 476[M+H]$^+$

EXAMPLE 374

4-[((1S,2R)-2-{[amino(imino)methyl]amino}cyclohexyl)amino]-6-methyl-N-[(1-(pyridin-2-yl)pyrrolidin-2-yl)methyl]quinazoline-2-carboxamide trihydrochloride Positive ion FAB-MS m/z: 502[M+H]$^+$

EXAMPLE 375

4-[((1S,2R)-2-{[amino(imino)methyl]amino}cyclohexyl)amino]-6-methyl-N-[2-(4-methyl-1,3-thiazol-5-yl)ethyl]quinazoline-2-carboxamide trihydrochloride Positive ion FAB-MS m/z: 467[M+H]$^+$

EXAMPLE 376

4-[((S,2R)-2-{[amino(imino)methyl]amino}cyclohexyl)amino]-N-[2-(3,5-dimethylisoxazol-4-yl)ethyl]-6-methylquinazoline-2-carboxamide Positive ion FAB-MS m/z: 465[M+H]$^+$

EXAMPLE 377

4-[((1S,2R)-2-{[amino(imino)methyl]amino}cyclohexyl)amino]-N-(trans-4-methoxycyclohexyl)-6-methylquinazoline-2-carboxamide dihydrochloride Positive ion FAB-MS m/z: 454[M+H]$^+$

EXAMPLE 378

4-[((1S,2R)-2-{[amino(imino)methyl]amino}cyclohexyl)amino]-N-(2,3-dihydro-1H-inden-2-yl)-6-methylquinazoline-2-carboxamide dihydrochloride Positive ion FAB-MS m/z: 458[M+H]$^+$

EXAMPLE 379

4-[((1S,2R)-2-{[amino(imino)methyl]amino}cyclohexyl)amino]-6-methyl-N-[4-(trifluoromethoxy)benzyl]quinazoline-2-carboxamide dihydrochloride Positive ion FAB-MS m/z: 516[M+H]$^+$

EXAMPLE 380

4-[((1S,2R)-2-{[amino(imino)methyl]amino}cyclohexyl)amino]-N-(3-ethoxy-2,2-dimethylpropyl)-6-methylquinazoline-2-carboxamide dihydrochloride Positive ion FAB-MS m/z: 456[M+H]$^+$

EXAMPLE 381

4-[((1S,2R)-2-{[amino(imino)methyl]amino}cyclohexyl)amino]-6-methyl-N-[2-(3-thienyl)ethyl]quinazoline-2-carboxamide dihydrochloride Positive ion FAB-MS m/z: 452[M+H]$^+$

EXAMPLE 382

4-[((1S,2R)-2-{[amino(imino)methyl]amino}cyclohexyl)amino]-6-methyl-N-n-propylquinazoline-2-carboxamide dihydrochloride Positive ion FAB-MS m/z: 384[M+H]$^+$

EXAMPLE 383

4-[((1S,2R)-2-{[amino(imino)methyl]amino}cyclohexyl)amino]-N-isobutyl-6-methylquinazoline-2-carboxamide dihydrochloride Step 1 4-{[(1S,2R)-2-({[(tert-butoxycarbonyl)amino][(tert-butoxycarbonyl)imino]methyl}amino)cyclohexyl]amino}-N-isobutyl-6-methylquinazoline-2-carboxamide To a solution of 400 mg of 4-{[(1S,2R)-2-({[(tert-butoxycarbonyl)amino][(tert-butoxycarbonyl)imino]methyl}amino)cyclohexyl]amino}-6-methylquinazoline-2-carboxylic acid, 0.15 ml of isobutylamine, 285 mg of 1-(3-dimethylaminopropyl)-3-ethylcarbodiimide hydrochloride and 200 mg of 1-hydroxybenzotriazole in 7 ml of N,N'-dimethylformamide, 0.41 ml of triethylamine was added, and then the mixture was stirred at room temperature for 24 hours. The reaction solution was mixed with water and then extracted with ethyl acetate. The organic layer was washed with water and saturated brine and then dried over magnesium sulfate. The solvent was distilled off and the residue was purified by silica gel column chromatography (chloroform) to obtain 242 mg of the desirable compound as a white powder.

Step 2 4-[((1S,2R)-2-{[amino(imino)methyl]amino}cyclohexyl)amino]-N-isobutyl-6-methylquinazoline-2-carboxamide dihydrochloride To a solution of 242 mg of 4-{[(1S,2R)-2-({(tert-butoxycarbonyl)amino[(tert-butoxycarbonyl)imino]methyl}amino)cyclohexyl]amino}-N-isobutyl-6-methylquinazoline-2-carboxamide in 6 ml of methylene chloride, 6 ml of trifluoroacetic acid was added, and then the mixture was reacted at room temperature for 15 hours. After the reaction solution was concentrated, the residue was purified by Fuji Silysia NH silica gel column chromatography (chloroform:methanol=5:1) to obtain a white powder (160 mg). The resulting powder was suspended in 2 ml of ethyl acetate and 5 ml of a 4N-hydrogen chloride-ethyl acetate solution was added, followed by stirring for one hour. The deposit was collected by filtration, washed with ethyl acetate and then dried to obtain 151 mg of the desirable compound as a white powder.

Elemental analysis for $C_{21}H_{31}N_7O_2HCl.0.2H_2O$ Calcd. (%): C, 53.21; H, 7.10; N, 20.68. Found (%): C, 53.02; H, 6.99; N, 20.97.

Positive ion FAB-MS m/z: 398[M+H]$^+$

Specific rotation $[\alpha]^{20}_D$=+18.18 (c=0.5 methanol).

In the same manner as in Example 1, 2 or 383, the following compounds were obtained.

EXAMPLE 384

4-[((1S,2R)-2-{[amino(imino)methyl]amino}cyclohexyl)amino]-6-methyl-N-[2-(methylthio)ethyl]quinazoline-2-carboxamide dihydrochloride Positive ion FAB-MS m/z: 416[M+H]$^+$

EXAMPLE 385

4-[((1S,2R)-2-{[amino(imino)methyl]amino}cyclohexyl)amino]-N-(cyclopropylmethyl)-6-methylquinazoline-2-carboxamide dihydrochloride Positive ion FAB-MS m/z: 396[M+H]$^+$

EXAMPLE 386

4-[((1S,2R)-2-{[amino(imino)methyl]amino}cyclohexyl)amino]-6-methyl-N-(2-propyn-1-yl)quinazoline-2-carboxamide dihydrochloride Positive ion FAB-MS m/z: 380[M+H]$^+$

EXAMPLE 387

4-[((1S,2R)-2-{[amino(imino)methyl]amino}cyclohexyl)amino]-6-methyl-N-(2-(pyridin-4-yl)ethyl)quinazoline-2-carboxamide trihydrochloride Positive ion FAB-MS m/z: 447[M+H]$^+$

EXAMPLE 388

4-[((1S,2R)-2-{[amino(imino)methyl]amino}cyclohexyl)amino]-N-isopropyl-6-methylquinazoline-2-carboxamide dihydrochloride Positive ion FAB-MS m/z: 384[M+H]$^+$

EXAMPLE 389

4-[((1S,2R)-2-{[amino(imino)methyl]amino}cyclohexyl)amino]-N-[2-(4-fluorophenyl)ethyl]-6-methylquinazoline-2-carboxamide dihydrochloride Positive ion FAB-MS m/z: 464[M+H]$^+$

EXAMPLE 390

4-[((1S,2R)-2-{[amino(imino)methyl]amino}cyclohexyl)amino]-6-methyl-N-(3-pyridin-3-ylpropyl)quinazoline-2-carboxamide trihydrochloride Positive ion FAB-MS m/z: 461[M+H]$^+$

EXAMPLE 391

4-[((1S,2R)-2-{[amino(imino)methyl]amino}cyclohexyl)amino]-N-(2-cyclopropylethyl)-6-methylquinazoline-2-carboxamide Positive ion FAB-MS m/z: 410[M+H]$^+$

EXAMPLE 392

4-[((1S,2R)-2-{[amino(imino)methyl]amino}cyclohexyl)amino]-6-methyl-N-[2-(trifluoromethyl)benzyl]quinazoline-2-carboxamide dihydrochloride Positive ion FAB-MS m/z: 500[M+H]$^+$

EXAMPLE 393

4-[((1S,2R)-2-{[amino(imino)methyl]amino}cyclohexyl)amino]-N-(3-chlorobenzyl)-6-methylquinazoline-2-carboxamide dihydrochloride Positive ion FAB-MS m/z: 466[M+H]$^+$

EXAMPLE 394

4-[((1S,2R)-2-{[amino(imino)methyl]amino}cyclohexyl)amino]-N-n-butyl-N,6-dimethylquinazoline-2-carboxamide dihydrochloride Positive ion FAB-MS m/z: 412[M+H]$^+$

EXAMPLE 395

4-[((1S,2R)-2-{[amino(imino)methyl]amino}cyclohexyl)amino]-N-(cyclobutylmethyl)-6-methylquinazoline-2-carboxamide dihydrochloride Positive ion FAB-MS m/z: 410[M+H]$^+$

EXAMPLE 396

4-[((1S,2R)-2-{[amino(imino)methyl]amino}cyclohexyl)amino]-N-(3-n-butoxypropyl)-6-methylquinazoline-2-carboxamide dihydrochloride Positive ion FAB-MS m/z; 456[M+H]$^+$

EXAMPLE 397

4-[((1S,2R)-2-{[amino(imino)methyl]amino}cyclohexyl)amino]-N-(3-fluorobenzyl)-6-methylquinazoline-2-carboxamide dihydrochloride Positive ion FAB-MS m/z: 450[M+H]$^+$

EXAMPLE 398

N-{(1R,2S)-2-[(2-{[(2S)-2-(methoxymethyl)pyrrolidin-1-yl]carbonyl}-6-methylquinazolin-4-yl)amino]cyclohexyl}guanidine dihydrochloride Positive ion FAB-MS m/z: 440[M+H]$^+$

EXAMPLE 399

4-[((1S,2R)-2-{[amino(imino)methyl]amino}cyclohexyl)amino]-N-{[1-(methoxymethyl)cyclopropyl]methyl}-6-methylquinazoline-2-carboxamide dihydrochloride Positive ion FAB-MS m/z: 440[M+H]$^+$

EXAMPLE 400

4-[((1S,2R)-2-{[amino(imino)methyl]amino}cyclohexyl)amino]-6-methyl-N-[(1-methylcyclohexyl)methyl]quinazoline-2-carboxamide dihydrochloride Positive ion FAB-MS m/z; 452[M+H]$^+$

EXAMPLE 401

4-[((1S,2R)-2-{[amino(imino)methyl]amino}cyclohexyl)amino]-N-[3,5-bis(trifluoromethyl)benzyl]-G-methylquinazoline-2-carboxamide dihydrochloride Positive ion FAB-MS m/z: 568[M+H]

EXAMPLE 402

4-[((1S,2R)-2-{[amino(imino)methyl]amino}cyclohexyl)amino]6-methyl-N-[3-(trifluoromethyl)benzyl]quinazoline-2-carboxamide dihydrochloride Positive ion FAB-MS m/z: 500[M+H]$^+$

EXAMPLE 403

4-[((1RS,2SR)-2-{[amino(imino)methyl]amino}cyclohexyl)amino]-N-cyclooctyl-6-methylquinazoline-2-carboxamide bis(trifluoroacetate)

Positive ion FAB-MS m/z: 452[M+H]$^+$

EXAMPLE 404

4-[((1RS,2SR)-2-{[amino(imino)methyl]amino}cyclohexyl)amino]-N-{(2-[ethyl(3-methylphenyl)amino]ethyl}-6-methylquinazoline-2-carboxamide bis(trifluoroacetate)

Positive ion FAB-MS m/z: 503[M+H]$^+$

EXAMPLE 405

4-[((1RS,2SR)-2-{[amino(imino)methyl]amino}cyclohexyl)amino]-6-methyl-N-(2-(pyridin-4-yl)ethyl)quinazoline-2-carboxamide tris(trifluoroacetate)

Positive ion FAB-MS m/z: 447[M+H]$^+$

EXAMPLE 406

4-[((1RS,2SR)-2-{[amino(imino)methyl]amino}cyclohexyl)amino]-N-cyclopentyl-6-methylquinazoline-2-carboxamide bis(trifluoroacetate)

Positive ion FAB-MS m/z; 410[M+H]$^+$

EXAMPLE 407

4-[((1RS,2SR)-2{[amino(imino)methyl]amino}cyclohexyl)amino]-N-(2,4-dichlorobenzyl)-6-methylquinazoline-2-carboxamide bis(trifluoroacetate)

Positive ion FAB-MS m/z: 500[M+H]$^+$

EXAMPLE 408

4-[((1RS,2SR)-2-{[amino(imino)methyl]amino}cyclohexyl)amino]-N-(2-furylmethyl)-6-methylquinazoline-2-carboxamide bis(trifluoroacetate)

Positive ion FAB-MS m/z: 422[M+H]$^+$

EXAMPLE 409

4-[((1RS,2SR)-2-{[amino(imino)methyl]amino}cyclohexyl)amino]-6-methyl-N-(4-methylcyclohexyl)quinazoline-2-carboxamide bis(trifluoroacetate)

Positive ion FAB-MS m/z: 438[M+H]$^+$

EXAMPLE 410

4-[((1RS,2SR)-2-{[amino(imino)methyl]amino}cyclohexyl)amino]-N-isobutyl-6-methylquinazoline-2-carboxamide bis(trifluoroacetate)

Positive ion FAB-MS m/z: 398[M+H]$^+$

EXAMPLE 411

4-[((1RS,2SR)-2-{[amino(imino)methyl]amino}cyclohexyl)amino]-6-methyl-N-[3-(methylthio)propyl]quinazoline-2-carboxamide bis(trifluoroacetate)

Positive ion FAB-MS m/z: 430[M+H]$^+$

EXAMPLE 412

4-[((1RS,2SR)-2-{[amino(imino)methyl]amino}cyclohexyl)amino]-6-methyl-N-(3-methylbutyl)quinazoline-2-carboxamide bis(trifluoroacetate)

Positive ion FAB-MS m/z: 412[M+H]$^+$

EXAMPLE 413

4-[((1RS,2SR)-2-{[(amino(imino)methyl]amino}cyclohexyl)amino]-N-(1,1-dimethylpropyl)-6-methylquinazoline-2-carboxamide bis(trifluoroacetate)

Positive ion FAS-MS m/z: 412[M+H]$^+$

EXAMPLE 414

4-[((1RS,2SR)-2-{[amino(imino)methyl]amino}cyclohexyl)amino]-6-methyl-N-n-octylquinazoline-2-carboxamide bis(trifluoroacetate)

Positive ion FAS-MS m/z: 454[M+H]$^+$

EXAMPLE 415

4-[((1RS,92SR)-2-{[amino(imino)methyl]amino}cyclohexyl)amino]-N-(2-bromobenzyl)-6-Methylquinazoline-2-carboxamide bis(trifluoroacetate)

Positive ion FAB-MS m/z: 510[M+H]$^+$

EXAMPLE 416

4-[((1RS,2SR)-2-{[amino(imino)methyl]amino}cyclohexyl)amino]-N-[1-(methoxymethyl)propyl]-6-methylquinazoline-2-carboxamide bis(trifluoroacetate)

Positive ion FAB-MS m/z: 428[M+H]$^+$

EXAMPLE 417

4-[((1RS,2SR)-2-{[amino(imino)methyl]amino}cyclohexyl)amino]-N-(3-n-butoxypropyl)-6-methylquinazoline-2-carboxamide bis(trifluoroacetate)

Positive ion FAB-MS m/z: 456[M+H]$^+$

EXAMPLE 418

4-[((1RS,2SR)-2-{[amino(imino)methyl]amino}cyclohexyl)amino]-N-(2-methoxybenzyl)-6-methylquinazoline-2-carboxamide bis(trifluoroacetate)

Positive ion FAB-MS m/z: 462[M+H]$^+$

EXAMPLE 419

4-[((1RS,2SR)-2-{[amino(imino)methyl]amino}cyclohexyl)amino]-N-[2-(1-cyclohexen-1-yl)ethyl]-6-methylquinazoline-2-carboxamide bis(trifluoroacetate)

Positive ion FAB-MS m/z: 450[M+H]$^+$

EXAMPLE 420

4-[((1RS,2SR)-2-{[amino(imino)methyl]amino}cyclohexyl)amino]-N-(1H-benzimidazol-2-ylmethyl)-6-methylquinazoline-2-carboxamide tris(trifluoroacetate)

Positive ion FAB-MS m/z: 472[M+H]$^+$

EXAMPLE 421

4-[((1RS,2SR)-2-{[amino(imino)methyl]amino}cyclohexyl)amino]-6-methyl-N-(2-(pyridin-3-yl)ethyl)quinazoline-2-carboxamide tris(trifluoroacetate)

Positive ion FAB-MS m/z: 447[M+H]

EXAMPLE 422

4-[((1RS,2SR)-2-{[amino(imino)methyl]amino}cyclohexyl)amino]-6-methyl-N-[(5-methylpyrazin-2-yl)methyl]quinazoline-2-carboxamide tris(trifluoroacetate)

Positive ion FAB-MS m/z: 448[M+H]$^+$

EXAMPLE 423

N-({4-[((1RS,2SR)-2-{[amino(imino)methyl]amino}cyclohexyl)amino]-6-methylquinazolin-2-yl}carbonyl)-4-chlorophenylalanine ethyl ester bis(trifluoroacetate)

Positive ion FAB-MS m/z: 552[M+H]$^+$

EXAMPLE 424

N-({4-[((1RS,2SR)-2-{[amino(imino)methyl]amino}cyclohexyl)amino]-6-methylquinazolin-2-yl}carbonyl)tyrosine methyl ester bis(trifluoroacetate)

Positive ion FAB-MS m/z: 520[M+H]$^+$

EXAMPLE 425

N-({4-[((1RS,2SR)-2-{[amino(imino)methyl]amino}cyclohexyl)amino]-6-methylquinazolin-2-yl}carbonyl) valine benzyl ester bis(trifluoroacetate)

Positive ion FAB-MS m/z: 532[M+H]$^+$

EXAMPLE 426

N-({4-[((1RS,2SR)-2-{[amino(imino)methyl]amino}cyclohexyl)amino]-6-methylquinazolin-2-yl}carbonyl)-S-benzylcysteine benzyl ester bis(trifluoroacetate)

Positive ion FAB-MS m/z: 626[M+H]$^+$

EXAMPLE 427

N-({4-[((1RS,2SR)-2-{[amino(imino)methyl]amino}cyclohexyl)amino]-6-methylquinazolin-2-yl}carbonyl)serine methyl ester bis(trifluoroacetate)

Positive ion FAB-MS m/z: 444[M+H]$^+$

EXAMPLE 428

N-({4-[((1RS,2SR)-2-{[amino(imino)methyl]amino}cyclohexyl)amino]-6-methylquinazolin-2-yl}carbonyl)histidine methyl ester tris(trifluoroacetate)

Positive ion FAB-MS m/z: 494[M+H]$^+$

EXAMPLE 429

4-[((1RS,2SR)-2-{[amino(imino)methyl]amino}cyclohexyl)amino]-N-[(2E)-3,7-dimethylocta-2,6-dien-1-yl]-6-methylquinazoline-2-carboxamide bis(trifluoroacetate)

Positive ion FAB-MS m/z: 478[M+H]$^+$

EXAMPLE 430

4-[((1RS,2SR)-2-{[amino(imino)methyl]amino}cyclohexyl)amino]-6-methyl-N-(2-oxotetrahydrofuran-3-yl)quinazoline-2-carboxamide bis(trifluoroacetate)

Positive ion FAB-MS m/z: 426[M+H]$^+$

EXAMPLE 431

4-[((1RS,2SR)-2-{[amino(imino)methyl]amino}cyclohexyl)amino]-N-[2-(2,4-dichlorophenyl)ethyl]-6-methylquinazoline-2-carboxamide bis(trifluoroacetate)

Positive ion FAB-MS m/z: 514[M+H]$^+$

EXAMPLE 432

4-[((1RS,2SR)-2-{[amino(imino)methyl]amino}cyclohexyl)amino]-N-[2-(dimethylamino)ethyl]-6-methylquinazoline-2-carboxamide tris(trifluoroacetate)

Positive ion FAB-MS m/z: 413[M+H]$^+$

EXAMPLE 433

4-[((1RS,2SR)-2-{[amino(imino)methyl]amino}cyclohexyl)amino]-6-methyl-N-n-pentylquinazoline-2-carboxamide bis(trifluoroacetate)

Positive ion PAD-MS m/z: 412[M+H]$^+$

EXAMPLE 434

4-[((1RS,2SR)-2-{[amino(imino)methyl]amino}cyclohexyl)amino]-6-methyl-N-(2-(pyrrolidin-1-yl)ethyl)quinazoline-2-carboxamide tris(trifluoroacetate)

Positive ion FAB-MS m/z: 439[M+H]$^+$

EXAMPLE 435

4-[((1RS,2SR)-2-{[amino(imino)methyl]amino}cyclohexyl)amino]-N-[3-(dimethylamino)propyl]-6-methylquinazoline-2-carboxamide tris(trifluoroacetate)

Positive ion FAB-MS m/z: 427[M+H]$^+$

EXAMPLE 436

4-[((1RS,2SR)-2-{[amino(imino)methyl]amino}cyclohexyl)amino]-6-methyl-N-(2-phenoxyethyl)quinazoline-2-carboxamide bis(trifluoroacetate)

Positive ion FAB-MS m/z: 462[M+H]$^+$

EXAMPLE 437

4-[((1RS,2SR)-2-{[amino(imino)methyl]amino}cyclohexyl)amino]-6-methyl-N-(3-n-propyloxypropyl)quinazoline-2-carboxamide bis(trifluoroacetate)

Positive ion FAB-MS m/z: 442[M+H]$^+$

EXAMPLE 438

4-[((1RS,2SR)-2-{[amino(imino)methyl]amino}cyclohexyl)amino]-6-methyl-N-(1-methylbutyl)quinazoline-2-carboxamide bis(trifluoroacetate)

Positive ion FAB-MS m/z: 412[M+H]$^+$

EXAMPLE 439

4-[((1S,2R)-2-{[amino(imino)methyl]amino}cyclohexyl)amino]-N-{[-(methoxymethyl)cyclohexyl]methyl}-6-methylquinazoline-2-carboxamide dihydrochloride Positive ion FAB-MS m/z: 482[M+H]$^+$

EXAMPLE 440

4-[((1R,2S)-2-{[amino(imino)methyl]amino}cyclohexyl)amino]-N-isobutyl-6-methylquinazoline-2-carboxamide dihydrochloride Positive ion FAB-MS m/z: 398[M+H]$^+$

EXAMPLE 441

4-[((1S,2R)-2-{[amino(imino)methyl]amino}cyclohexyl)amino]-N-(cyclopentylmethyl)-6-methylquinazoline-2-carboxamide dihydrochloride Positive ion FAB-MS m/z: 424[M+H]$^+$

EXAMPLE 442

4-[(2-{[amino(imino)methyl]amino}phenyl)amino]-N-(4-methoxyphenyl)-6-methylquinazoline-2-carboxamide dihydrochloride Positive ion FAB-MS m/z: 442[M+H]$^+$

TEST EXAMPLE 1

Nociceptin Receptor Binding Assay

A cell membrane suspension obtained from a human nociceptin receptor-expressing cell was prepared so that it contained 5 to 10 µg/mL of the membrane protein in a Tris buffer [50 mM Tris-HCl (pH7.8), 5 mM MgCl$_2$, 1 mM EGTA [Ethylene Glycol Bis(β-aminoethylether)-N,N,N',N'-tetraacetic Acid], 0.1% BSA (Bovine Serum Alubumin)]. To this, [$^3$H]nociceptin (diluted at the final concentration of 0.08 nM with the Tris buffer) and each test compound was added and the mixture was incubated at 25° C. for 60 minutes. Using a cell harvester and a washing solution [50 mM Tris-HCl (pH7.8), 4° C.], the membrane was recovered onto a GF/B filter which had been pretreated with 0.3% PEI (polyethylenimine), which was then washed further 3 times. The filter was transferred to a vial, to which a scintillator was added, and the radioactivity was measured using a liquid scintillation counter. Noted that a non-specific binding was regarded as a binding in the presence of 10 µM nociceptin, and a specific binding was obtained by subtracting the non-specific binding from the total binding. From a ratio of binding inhibition in the presence of the tested substance, an IC$_{50}$ value was obtained, and was then used together with the Kd value for [$^3$H]nociceptin to calculate the Ki value for the tested substance. The results were shown in Table 1.

TABLE 1

| Test compounds (Example No.) | Affinity for nociceptin receptors Ki value (µM) |
|---|---|
| 1 | 0.00015 |
| 3 | 0.00014 |
| 6 | 0.00067 |
| 7 | 0.00065 |
| 12 | 0.00057 |

TEST EXAMPLE 2

µ Opioid Receptor Binding Assay

A rat µ opioid receptor-expressing cell membrane preparation was prepared so that it contained 8.5 µg/mL of the membrane protein in a Tris buffer [50 mM Tris-HCl (pH7.8), 5 mM MgCl$_2$, 1 mM EGTA, 0.1% BSA]. To this, [$^3$H]diprenorphine (diluted at the final concentration of 0.5 nM with the Tris buffer) and each test compound was added and the mixture was incubated at 25° C. for 60 minutes. Using a cell harvester and a washing solution [50 mM Tris-HCl (pH7.8), 4° C.], the membrane was recovered onto a GF/B filter which had been pretreated with 0.3% PEI, which was then washed further 3 times. The filter was transferred to a vial, to which a scintillator was added, and the radioactivity was measured using a liquid scintillation counter. Noted that a non-specific binding was regarded as a binding in the presence of 100 µM nociceptin, and a specific binding was obtained by subtracting the non-specific binding from the total binding. From a ratio of binding inhibition in the presence of the tested substance, an IC$_{50}$ value was obtained, and was then used together with the Kd value for [$^3$H]diprenorphine to calculate the Ki value for the tested substance. The results were shown in Table 2.

TABLE 2

| Test compounds (Example No.) | Affinity for µ receptors Ki value (µM) |
|---|---|
| 1 | 0.18 |
| 3 | 0.26 |
| 6 | 0.55 |
| 7 | 0.57 |
| 12 | 0.68 |

As is apparent from the results shown in Table 1 and Table 2, the inventive compounds have a selective binding effect on the nociceptin receptor.

TEST EXAMPLE 3

Effect on Mouse Eye-scratching Behavior Induced by Serotonin

After dropping 10 μl of 1% serotonin hydrochloride (hereinafter referred to as serotonin) into right eye of ICR male mice (4 to 6 weeks old), the number of eye-scratcing behavior induced by dropping of serotonin was measured for 10 minutes.

As the test compound, inventive compounds of Example 1, Example 2, Example 3, Example 6, Example 12, Example 29, Example 52, Example 364, Example 381 and Example 383 were used. Five minutes before dropping serotonin, 10 μl of each test compound was dropped. Distilled water as a solvent of the test compound was dropped as a control group.

The results are shown in Table 3.

TABLE 3

| Test compounds | | Average number of scratching behavior | Standard error | Number of test animals (n =) |
| --- | --- | --- | --- | --- |
| Control group | | 26.57 | 4.06 | 7 |
| Example 1 | 0.5% | 9.57 | 2.57 | 7 |
| Example 2 | 0.5% | 7.25 | 2.24 | 8 |
| Example 3 | 0.5% | 2.33 | 0.84 | 6 |
| Example 6 | 0.5% | 2.38 | 0.68 | 8 |
| Example 12 | 0.5% | 8.17 | 3.08 | 6 |
| Example 29 | 0.5% | 1.67 | 0.92 | 6 |
| Example 52 | 0.5% | 4.50 | 1.34 | 6 |
| Example 364 | 0.5% | 5.17 | 1.60 | 6 |
| Example 381 | 0.5% | 5.00 | 1.71 | 6 |
| Example 383 | 0.5% | 2.33 | 1.28 | 6 |

The test compounds strongly suppressed eye-scratching behavior induced by dropping of serotonin. This fact shows that the inventive compounds are effective for eye itching when used as an ophthalmic solution or an ophthalmic ointment.

TEST EXAMPLE 4

Effect on Mouse Spontaneous Scratching Behavior Induced by Cutaneous Barrier Disruption After shaving backs of ICR male mice (5 weeks old) under ether anesthesia, the cutaneous barrier was disrupted by carrying out a treatment of applying a solution mixture of acetone and ether in a ratio of 1:1 was applied on the shaved site and then applying distilled water twice a day everyday (10 days). Spontaneous scratching behavior to the vicinity of the shaved site induced by cutaneous barrier disruption was observed before and after administration of the test drug using a video system under an unmanned condition and change (%) in number of scratching behavior was measured. As the solvent, 100% ethanol was used. As the test compound, the inventive compounds of Example 1, Example 2, Example 3, Example 6, Example 12, Example 29, Example 52, Example 364, Example 381 and Example 383 were used. The drug was applied to the vicinity of the shaved site (100 μl).

The results are shown in Table 4.

TABLE 4

| Test compounds | | Average number of scratching behavior | Standard error | Number of test animals (n =) |
| --- | --- | --- | --- | --- |
| Control group | | 143.03 | 45.34 | 9 |
| Example 1 | 0.10% | 16.47 | 5.94 | 9 |
| Example 2 | 0.10% | 30.24 | 8.65 | 8 |
| Example 3 | 0.10% | 14.81 | 4.64 | 8 |
| Example 6 | 0.10% | 45.41 | 20.19 | 7 |
| Example 12 | 0.10% | 20.82 | 6.39 | 8 |
| Example 29 | 0.10% | 15.74 | 6.02 | 6 |
| Example 52 | 0.10% | 24.74 | 14.38 | 5 |
| Example 364 | 0.01% | 53.36 | 21.47 | 8 |
| Example 381 | 0.01% | 68.73 | 13.64 | 6 |
| Example 383 | 0.01% | 20.73 | 7.23 | 8 |

The test compounds strongly suppressed spontaneous scratching behavior induced by cutaneous barrier disruption. This fact shows that the inventive compounds are also effective for xeroderma, atopic dermatitis and systemic itching when used as an external agent.

FORMULATION EXAMPLE 1

100 g of the inventive compound of Example 1, 292 g of D-mannitol, 120 g of corn starch and 28 g of a low substituted hydroxypropyl cellulose are placed in a fluidized bed granulator (STREA; PAUREC) and granulated with spraying a certain amount of an aqueous 5% hydroxypropyl cellulose solution. After drying and then milling by a grinding/milling machine (COMIL; PAULEC), a certain amount of magnesium stearate is admixed by a mixer (BOHRE container mixer Model MC20, KOTOBUKI-GIKEN), and the mixture is subjected to a rotary tablet compacting machine (CORRECT 12HUK; KIKUSUI) to mold into tablets each 7 mm in diameter weighing 140 mg per tablet, thereby obtaining a tablet containing 25 mg of the inventive compound.

FORMULATION EXAMPLE 2

75 g of the inventive compound of Example 1, 180 g of lactose, 75 g of corn starch and 18 g of croscarmellose calcium are placed in a stirring granulator (vertical granulator model VG-01), combined with a certain amount of an aqueous 5% hydroxypropylmethyl cellulose solution and granulated, and then dried by a fluidized bed granulating drier (STREA; PAUREC) and then milled by a grinding/milling machine (COMIL; manufactured by PAULEC). Each 120 mg of the milled material is filled into a #3 capsule using a capsule filling machine (capsule filler; SHIONOGI QUALI-CAPS), thereby obtaining a capsule containing 25 mg of the inventive compound.

FORMULATION EXAMPLE 3

2.5 g of the inventive compound of Example 1 and 4.5 g of sodium chloride are weighed, combined with 450 mL of water for injection and stirred and dissolved, and adjusted at pH 6.5 with 0.1 mol/L hydrochloric acid or 0.1 mol/L sodium hydroxide. Then water for injection is added to make the entire quantity 500 mL. The solution thus formulated is filtered under pressure through a membrane filter (pore size: 0.22 μm). Then 5.3 mL is filled aseptically to a sterilized 5 mL brown ampoule, thereby obtaining an injection formulation containing 25 mg of the inventive compound. The procedure from the preparation through the filling is performed aseptically.

FORMULATION EXAMPLE 4

99.75 g of UITEPSOL H-15 (manufactured by HIRTH) is dissolved at 45° C. and combined with 0.25 g of the inventive compound of Example 1, and dispersed by stirring. This was infused into a 1 g suppository mold carefully to prevent sedimentation while hot, solidified and taken out from the mold, thereby obtaining a suppository containing 25 mg of the inventive compound.

FORMULATION EXAMPLE 5

0.5 g of the inventive compound of Example 1, 5.2 g of sodium dihydrogenphosphate, 11.9 g of sodium monohydrogenphosphate, 2.5 g of sodium chloride and 0.3 g of benzalkonium chloride were weighed, combined with 950 ml of purified water, and stirred and dissolved. Then purified water is added to make the entire quantity 1000 mL. The solution thus formulated is filtered under pressure through a membrane filter (pore size: 0.2 μm). Then 5 mL is filled aseptically to a sterilized 5 mL eye drop bottle, thereby obtaining an ophthalmic solution (5 ml) containing 0.5 mg/mL of the inventive compound. The procedure from the preparation through the filling is performed aseptically.

FORMULATION EXAMPLE 6

80 g of olive oil, 15 g of cetanol and 15 g of stearyl alcohol are weighed, stirred and dissolved while heating to 70° C. on a water bath (oil phase). Separately, 1 g of the inventive compound of Example 1, 10 g of Polysolvate 80, 5 g of sodium lauryl sulfate, 0.25 g of methyl paraoxybenzoate, 0.15 g of propyl paraoxybenzoate and 880 g of purified water are weighed, stirred and dissolved while heating to 70° C. on a water bath (aqueous phase). The oil phase and the aqueous phase are placed in a vacuum emulsifying apparatus and then emulsified while stirring at high speed in a homomixer at 70° C. under vacuum. Then, the emulsion is water-cooled to 35° C. while stirring at low speed. Then 50 mL is filled to a 50 mL container for lotion, thereby obtaining a lotion (50 mL) containing 1.0 mg/mL of the inventive compound.

FORMULATION EXAMPLE 7

250 g of white vaseline 250 g of stearyl alcohol and 40 g of polyoxyethylene hardened castor oil 60 are weighed, stirred and dissolved while heating to 70° C. on a water bath (oil phase). Separately, 1 g of the inventive compound of Example 1, 120 g of propylene glycol, 0.25 g of methyl paraoxybenzoate, 0.15 g of propyl paraoxybenzoate and 340 g of purified water are weighed, stirred and dissolved while heating to 70° C. on a water bath (aqueous phase). The oil phase and the aqueous phase are placed in a vacuum mixing apparatus and then emulsified while stirring at 70° C. under vacuum. An ointment obtained by cooling the emulsion and slowly stirring until the emulsion is solidified is filled to a 10 g ointment bottle or a 10 g ointment tube, thereby obtaining an ointment containing 1.0 mg/g of the inventive compound.

FORMULATION EXAMPLE 8

110 g of gelatin, 25 g of polyvinyl alcohol and 10 g of methylcellulose are weighed and mixed to obtain a mixture. The mixture is dispersed in 13 g of glycerin using a small-sized mixer. The mixture is dissolved in 100 g of purified water while heating to 60° C. Furthermore, 85 g of kaolin is added and dispersed at 60° C. A dispersion obtained by mixing 20 g of glycerin with 5 g of sodium acrylate is added, and dissolved and dispersed at 60° C. Then 15 g of polybutene is added and dispersed at 60° C. To the dispersion, 0.5 g of the inventive compound of Example 1 is added and dispersed at 50° C. to obtain a paste (containing 0.5 g of the inventive compound in 500 g). The paste is spread over a support (nonwoven fabric) in a coating weight of 100 g/700 cm², and then the coated support is covered with a liner made of a polyethylene film (50 μm) and cut to obtain a patch. 1 mg of the inventive compound is contained in 7 cm² of the patch.

INDUSTRIAL APPLICABILITY

As described above, the inventive compounds can be used as a preventive or remedy for diseases associated with itching, for example, atopic dermatitis, urticaria, psoriasis, xeroderma, trichophytia and vitiligo vulgaris, local pruritus cutaneous caused by insect excretion and secretion, nodular prurigo, kidney dialysis, diabetes, blood disease, liver disease, kidney disease, incretion and metabolic disorder, viscera malignant tumor, hyperthyroidism, autoimmune disease, multiple sclerosis, neurologic disease, psychoneurosis, allergic conjunctivitis, spring catarrh, atopic keratoconjunctivitis, or itching caused by excess use of laxuries and drugs because it has excellent scratching behavior suppressing effect, for example, antipruritic effect. Since the inventive compounds have a nociceptin antagonism, they can be used as a remedy for diseases associated with pain, for example, cancer pain, postoperative pain, migraine, rheumatoid arthritis, and neurogenic pains such as herpes zoster and girdle pain; a remedy for mental disorder and biological disorder, especially a remedy for anxiety and stress disorder, depression, traumatic disorder, and memory disorder due to Alzheimer's disease or other dementia; a remedy for dietic disorder such as obesity; a remedy for arterial blood pressure disorder; and an agent for overcoming resistance to morphine.

The invention claimed is:

1. A quinazoline derivative represented by general formula (1b) or a salt thereof:

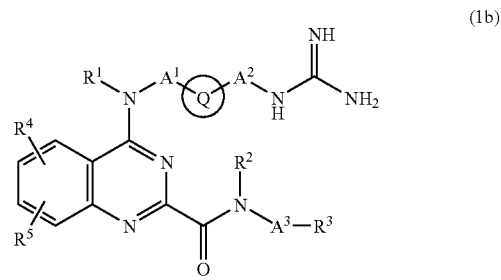

(1b)

wherein $R^1$ represents a hydrogen atom or alkyl;
the ring Q represents a cyclohexylene group or a phenylene group;
$A^1$ and $A^2$ are the same or different and each represents a single bond or an alkylene group;
$R^2$ represents a hydrogen atom or alkyl;
$A^3$ represents $A^{31}$-$A^{32}$-$A^{33}$,
$A^{31}$ and $A^{33}$ are the same or different and each represents a single bond, or a divalent saturated or unsaturated aliphatic hydrocarbon group having 1to 6 carbon atoms which may have the same or different 1 or 2 substituents at a substitutable position; wherein the substituents are selected from alkyl, alkoxy, phenyl, alkoxyalkyl, alkoxycarbonyl, dialkylamino, and oxo; or when one carbon atom has two branched chains, the branched chains may be taken together with the carbon atom to form divalent cycloalkyl;

$A^{32}$ represents a single bond, an oxygen atom, a sulfur atom, or —N($R^{32}$)—, wherein $R^{32}$ represents a hydrogen atom or alkyl;

$R^3$ represents an optionally substituted non-cyclic aliphatic hydrocarbon group having 1 to 8 carbon atoms, wherein the substituents are selected from alkyl, hydroxy, alkoxy, phenyl, alkoxy-substituted phenyl, halogen-substituted phenyl, hydroxy-substituted phenyl, phenoxy, alkylthio, carboxy, alkoxycarbonyl, acyl, amino, monoalkylamino, dialkylamino, acyl amino, alkylsulfonyl, alkylsulfonylamino, phenylsulfonyl, oxo, cyano, trifluoromethyl, benzoyl, benzyloxycarbonyl, benzylthio and imidazol-4-yl; an optionally substituted cyclic aliphatic hydrocarbon group having 3 to 10 carbon atoms which is mono- to tricyclic, wherein the substituents are selected from alkyl, alkynyl, alkoxy, alkoxycarbonyl, carbamoyl, aryl, alkoxyalkyl, acyl and oxo, and wherein the cyclic aliphatic hydrocarbon group may be fused with 1 or 2 benzene rings; or an optionally substituted aromatic hydrocarbon group having 6 to 12 carbon atoms which is mono- or dicyclic, wherein the substituents are selected from alkyl, arylalkyl, arylalkenyl, alkenyl, cinnamyl, alkoxy, phenyl, phenoxy, acyl, acylamino, alkoxycarbonyl, amino, aminoalkyl, monoalkylamino, dialkylamino, dialkylaminosulfonyl, alkylsulfonyl, alkylsulfonylamino, phenylsulfonyl, oxo, cyano, nitro, aminosulfonyl, halogen, trifluoromethyl, trifluoromethoxy, alkylthio, 1H-pyrrol-1-yl, 5-oxo-4,5-dihydro-1H-pyrazol-1-yl and aminosulfonyl; or the —N($R^2$)— may be taken together with -$A^3$-$R^3$ to form a mono- to tricyclic amino group; wherein the mono- to tricyclic amino group may have the same or different 1 to 3 substituents selected from the group consisting of alkyl, alkoxy, alkoxyalkyl, acyl, acylamino, alkoxycarbonyl, carbamoyl, monoalkylcarbamoyl, dialkylcarbamoyl, aryl optionally substituted with alkoxy, arylalkyl, arylalkenyl, piperidino, pyridyl, pyrimidinyl, pyrazinyl, and 1,3-benzodioxol-5-ylmethyl;

provided that $R^3$ is not an optionally substituted phenyl group; and $R^4$ and $R^5$ are the same or different and each represents a hydrogen atom, alkyl, alkoxy or halogen.

2. The quinazoline derivative according to claim 1 or a salt thereof, wherein $R^1$ is a hydrogen atom.

3. The quinazoline derivative according to claim 1 or a salt thereof, wherein the ring Q is a cyclohexylene group.

4. The quinazoline derivative according to claim 1, or a salt thereof, wherein $A^1$ and $A^2$ represent a single bond.

5. The quinazoline derivative according to claim 1 or a salt thereof, wherein $A^{31}$, $A^{32}$ and $A^{33}$ represent a single bond.

6. The quinazoline derivative according to claim 1 or a salt thereof, wherein $R^2$ is a hydrogen atom.

7. The quinazoline derivative according to claim 1 or a salt thereof, wherein $R^3$ is an optionally substituted non-cyclic aliphatic hydrocarbon group having 1 to 8 carbon atoms, or an optionally substituted cyclic aliphatic hydrocarbon group having 3 to 10 carbon atoms which is mono- to tricyclic.

8. The quinazoline derivative according to claim 1 or a salt thereof, wherein $R^4$ and $R^5$ are the same or different and each represents a hydrogen atom or alkyl.

9. The quinazoline derivative according to claim 1 or a salt thereof, wherein $R^1$ is a hydrogen atom, the ring Q is a cyclohexylene group, $A^1$ and $A^2$ represent a single bond, $A^{31}$, $A^{32}$ and $A^{33}$ represent a single bond, $R^2$ is a hydrogen atom, $R^3$ is an optionally substituted non-cyclic aliphatic hydrocarbon group having 1 to 8 carbon atoms or an optionally substituted cyclic aliphatic hydrocarbon group having 3 to 10 carbon atoms which is mono- to tricyclic, and $R^4$ and $R^5$ are the same or different and each represents a hydrogen atom or alkyl.

10. A quinazoline derivative or a salt thereof, wherein the quinazoline derivative is a compound selected from the group consisting of 4-[((1S,2R)-2-{[amino(imino)methyl]amino}cyclohexyl)amino]-6-methyl-N-neopentylquinazoline-2-carboxamide, 4-[((1S,2R)-2-{[amino(imino)methyl]amino}cyclohexyl)amino]-N-(3,3-dimethylbutyl)-6-methylquinazoline-2-carboxamide, 4-[((1S,2R)-2-{[amino(imino)methyl]amino}cyclohexyl)amino]-N-cycloheptyl-6-methylquinazoline-2-carboxamide, 4-[((1S,2R)-2-{[amino(imino)methyl]amino}cyclohexyl)amino]-N-(2ethylbutyl)-6-methylquinazoline-2-carboxamide, 4-[((1S,2R)-2-{[amino(imino)methyl]amino}cyclohexyl)amino]-6-methyl-N-n-propylquinazoline-2-carboxamide, and 4-[((1S,2R)-2-{[amino(imino)methyl]amino}cyclohexyl)amino]-N-isobutyl-6-methylquinazoline-2-carboxamide.

11. An antipruritic composition comprising the quinazoline derivative represented by the general formula (1b) of claim 1 or a salt thereof as an active ingredient, and a pharmaceutically acceptable carrier.

12. A method for treating itching, which comprises administering to a subject in need thereof an effective amount of the quinazoline derivative represented by the general formula (1b) of claim 1 or a salt thereof.

13. The quinazoline derivative according to claim 1, wherein the pyridyl substituent is selected from pyridin-2-yl and pyridin-4-yl.

14. The quinazoline derivative according to claim 1, wherein the pyrimidinyl substituent is pyrimidin-2-yl.

15. The quinazoline derivative according to claim 1, wherein the pyrazinyl substituent is pyrazin-2-yl.

16. A quinazoline derivative or a salt thereof, which is selected from the group consisting of:

4-[((1S,2R)-2-{[amino(imino)methyl]amino}cyclohexyl)amino]-N-(4-methoxyphenyl)-6-methylquinazoline-2-carboxamide dihydrochloride;

4-[((1S,2R)-2-{[amino(imino)methyl]amino}cyclohexyl)amino]-N-(4-bromophenyl)-6-methylquinazoline-2-carboxamide dihydrochloride;

4-[((1S,2R)-2-[amino(imino)methyl]amino}cyclohexyl)amino]-6-methyl-N-{4-[(methylsulfonyl)aminophenyl]quinazoline-2-carboxamide dihydrochloride;

4-[((1S,2R)-2-{[amino(imino)methyl]amino}cyclohexyl)amino]-N-(4-methoxyphenyl)-N,6-dimethylquinazoline-2-carboxamide dihydrochloride;

4-[((1S,2R)-2-{[amino(imino)methyl]amino}cyclohexyl)amino]-N-1-benzothiophen-2-yl-6-methylquinazoline-2-carboxamide dihydrochloride;

4-[((1S,2R)-2-{[amino(imino)methyl]amino}cyclohexyl)amino]-6-methyl-N-thiophen-3-ylquinazoline-2-carboxamide dihydrochloride;

4-((1S,2R)-2-{[amino(imino)methyl]amino}cyclohexyl)amino]-6-methyl-N-pyridin-2-ylquinazoline-2-carboxamide trihydrochloride;

4-[((1S,2R)-2-{[amino(imino)methyl]amino}cyclohexyl)amino]-6-methyl-N-quinolin-3-ylquinazoline-2-carboxamide trihydrochloride;

4-[((1S,2R)-2-{[amino(imino)methyl]amino}cyclohexyl)amino]-N-(4-chlorophenyl)-6-methylquinazoline-2-carboxamide dihydrochloride;

4-[((1S,2R)-2-{[amino(imino)methyl]amino}cyclohexyl)amino]-6-chloro-N-(4-methoxyphenyl)quinazoline-2-carboxamide dihydrochloride;

4-[((1S,2R)-2-{[amino(imino)methyl]amino}cyclohexyl)amino]-6-methoxy-N-(4-methoxyphenyl)quinazoline-2-carboxamide dihydrochloride;

4-[((1S,2R)-2-{[amino(imino)methyl]amino}cyclohexyl)amino]-6-methyl-N-(1-methyl-1H-benzimidazol-2-yl)quinazoline-2-carboxamide trihydrochloride;

4-[((1S,2R)-2-{[amino(imino)methyl]amino}cyclohexyl)amino]-6-methyl-N-thiophen-2-ylquinazoline-2-carboxamide dihydrochloride; 4-[((1S,2R)-2-{[amino(imino)methyl]amino}cyclohexyl)amino]-N-(4-methoxyphenyl)quinazoline-2-carboxamide dihydrochloride;

4-[((1S,2R)-2-{[amino(imino)methyl]amino}cyclohexyl)amino]-6-methyl-N-[4-(trifluoromethoxy)phenyl]quinazoline-2-carboxamide dihydrochloride;

4-[((1S,2R)-2-{[amino(imino)methyl]amino}cyclohexyl)amino]-N-(3,5-dimethylphenyl)-6-methylquinazoline-2-carboxamide dihydrochloride;

4-[((1S,2R)-2-{[amino(imino)methyl]amino}cyclohexyl)amino]-N-(2,6-dimethylphenyl)-6-methylquinazoline-2-carboxamide dihydrochloride;

4-[((1S,2R)-2-{[amino(imino)methyl]amino}cyclohexyl)amino]-N-(3,4-dimethylphenyl)-6-methylquinazoline-2-carboxamide dihydrochloride;

4-[((1S,2R)-2-{[amino(imino)methyl]amino}cyclohexyl)amino]-6-methyl-N-(2-oxo-2H-chromen-6-yl)quinazoline-2-carboxamide dihydrochloride;

4-[((1S,2R)-2-{[amino(imino)methyl]amino}cyclohexyl)amino]-N-(3-chloro-4-methoxyphenyl)-6-methylquinazoline-2-carboxamide dihydrochloride;

4-[((1S,2R)-2-{[amino(imino)methyl]amino}cyclohexyl)amino]-6-methyl-N-(3-oxo-3,4-dihydro-2H-1,4-benzoxazin-6-yl)quinazoline-2-carboxamide dihydrochloride;

4-[((1S,2R)-2-{[amino(imino)methyl]amino}cyclohexyl)amino]-N-(6-chloropyridin-3-yl)-6-methylquinazoline-2-carboxamide trihydrochloride;

4-[((1S,2R)-2-{[amino(imino)methyl]amino}cyclohexyl)amino]-N-(3,3-dimethylbutyl)-6-methylquinazoline-2-carboxamide trihydrochloride;

4-[((1S,2R)-2-{[amino(imino)methyl]amino}cyclohexyl)amino]-6-methyl-N-{4-[(E)-2-phenylvinyl]phenyl}quinazoline-2-carboxamide dihydrochloride;

4-[((1S,2R)-2-{[amino(imino)methyl]amino}cyclohexyl)amino]-6,7-dimethoxy-N-(4-methoxyphenyl)quinazoline-2-carboxamide dihydrochloride;

4-[(2-{[amino(imino)methyl]amino}cyclohexyl)amino]-6-methyl-N-quinolin-6-ylquinazoline-2-carboxamide tris(trifluoroacetate);

4-[(2-{[amino(imino)methyl]amino}cyclohexyl)amino]-N-(4-chlorophenyl)-6-methylquinazoline-2-carboxamide bis(trifluoroacetate);

4(2-{[amino(imino)methyl]amino}cyclohexyl)amino]-6-methyl-N-(2-thiophen-2-ylethyl)quinazoline-2-carboxamide bis(trifluoroacetate);

4-[(2-{[amino(imino)methyl]amino}cyclohexyl)amino]-6-methyl-N-[3-(trifluoromethyl)benzyl]quinazoline-2-carboxamide bis(trifluoroacetate);

4-[((1RS,2SR)-2-{[amino(imino)methyl]amino}cyclohexyl)amino]-N,6-dimethyl-N-(1-methylpiperidin-4-yl)quinazoline-2-carboxamide tris(trifluoroacetate);

4-[((1RS,2SR)-2-{[amino(imino)methyl]amino}cyclohexyl)amino]-N-2,3-dihydro-1,4-benzodioxan-6-yl-6-methylquinazoline-2-carboxamide bis(trifluoroacetate);

4-[((1RS,2SR)-2-{[amino(imino)methyl]amino}cyclohexyl)amino]-N-(1-benzylpiperidin-4-yl)-6-methylquinazoline-2-carboxamide tris(trifluoroacetate);

4-[((1RS,2SR)-2-{[amino(imino)methyl]amino}cyclohexyl)amino]-N-1,3-benzothiazol-2-yl-6-methylquinazoline-2-carboxamide bis(trifluoroacetate);

4-[((1RS,2SR)-2-{[amino(imino)methyl]amino}cyclohexyl)amino]-N-1-azabicyclo[2.2.2]oct-3-yl-6-methylquinazoline-2-carboxamide tris(trifluoroacetate);

N-((1RS,2SR)-2-{[6-methyl-2-(1,3-thiazolidin-3-ylcarbonyl)quinazolin-4-yl]amino}cyclohexyl)guanidine bis(trifluoroacetate);

4-[((1RS,2SR)-2-{[amino(imino)methyl]amino}cyclohexyl)amino]-6-methyl-N-(3-(2-methylpiperidin-1-yl)propyl)quinazoline-2-carboxamide tris(trifluoroacetate);

4-[((1RS,2SR)-2-{[amino(imino)methyl]amino}cyclohexyl)amino]-6-methyl-N-(2-(pyridin-2-yl)ethyl)quinazoline-2-carboxamide tris(trifluoroacetate);

4-[((1RS,2SR)-2-{[amino(imino)methyl]amino}cyclohexyl)amino]-6-methyl-N-{3-[methyl(phenyl)amino]propyl}quinazoline-2-carboxamide tris(trifluoroacetate);

4-[((1RS,2SR)-2-{[amino(imino)methyl]amino}cyclohexyl)amino]-N-(3-methoxyphenyl)-6-methylquinazoline-2-carboxamide bis(trifluoroacetate);

4-[((1RS,2SR)-2-{[amino(imino)methyl]amino}cyclohexyl)amino]-6-methyl-N-(pyridin-3-yl)quinazoline-2-carboxamide tris(trifluoroacetate);

4-[((1RS,2SR)-2-{[amino(imino)methyl]amino}cyclohexyl)amino]-6-methyl-N-(2-(morpholin-4-yl)ethyl)quinazoline-2-carboxamide tris(trifluoroacetate);

4-[((1RS,2SR)-2-{[amino(imino)methyl]amino}cyclohexyl)amino]-N-2,3-dihydro-1H-inden-5-yl-6-methylquinazoline-2-carboxamide bis(trifluoroacetate);

4-[((1RS,2SR)-2-{[amino(imino)methyl]amino}cyclohexyl)amino]-6-methyl-N-(3-phenoxyphenyl)quinazoline-2-carboxamide bis(trifluoroacetate);

4-[((1RS,2SR)-2-{[amino(imino)methyl]amino}cyclohexyl)amino]-6-methyl-N-(tetrahydrofuran-2-ylmethyl)quinazoline-2-carboxamide bis(trifluoroacetate);

4-[((1RS,2SR)-2-{[amino(imino)methyl]amino}cyclohexyl)amino]-N-(6-ethoxy-1,3-benzothiazol-2-yl)-6-methylquinazoline-2-carboxamide bis(trifluoroacetate);

4-[((1RS,2SR)-2-{[amino(imino)methyl]amino}cyclohexyl)amino]-6-methyl-N-(pyridin-2-ylmethyl)quinazoline-2-carboxamide tris(trifluoroacetate);

4-[((1RS,2SR)-2-{[amino(imino)methyl]amino}cyclohexyl)amino]-6-methyl-N-(pyridin-4-ylmethyl)quinazoline-2-carboxamide tris(trifluoroacetate);

4-[((1RS,2SR)-2-{[amino(imino)methyl]amino}cyclohexyl)amino]-6-methyl-N-(pyridin-3-ylmethyl)quinazoline-2-carboxamide tris(trifluoroacetate);

4-[((1RS,2SR)-2-{[amino(imino)methyl]amino}cyclohexyl)amino]-N-(1,3-benzodioxol-5-ylmethyl)-6-methylquinazoline-2-carboxamide bis(trifluoroacetate);

4-[((1RS,2SR)-2-{[amino(imino)methyl]amino}cyclohexyl)amino]-N-(4-benzylphenyl)-6-methylquinazoline-2-carboxamide bis(trifluoroacetate);

4-[((1RS,2SR)-2-{[amino(imino)methyl]amino}cyclohexyl)amino]-N-[4-(dimethylamino)benzyl]-6-methylquinazoline-2-carboxamide tris(trifluoroacetate);

4-[((1RS,2SR)-2-{[amino(imino)methyl]amino}cyclohexyl)amino]-N-(2-furylmethyl)-6-methylquinazoline-2-carboxamide bis(trifluoroacetate);

4-[((1RS,2SR)-2-{[amino(imino)methyl]amino}cyclohexyl)amino]-N-[(3R)-1-benzylpyrrolidin-3-yl]-6-methylquinazoline-2-carboxamide tris(trifluoroacetate);

4[((1RS,2SR)-2-{[amino(imino)methyl]amino}cyclohexyl)amino]-N-[2-(1-benzylpyrrolidin-3-yl)ethyl]-6-methylquinazoline-2-carboxamide tris(trifluoroacetate);

4-[((1RS,2SR)-2-{[amino(imino)methyl]amino}cyclohexyl)amino]-N-[2-(1H-indol-3-yl)ethyl]-6-methylquinazoline-2-carboxamide bis(trifluoroacetate);

4-[((1RS,2SR)-2-{[amino(imino)methyl]amino}cyclohexyl)amino]-N-[(3S)-1-benzylpyrrolidin-3-yl]-6-methylquinazoline-2-carboxamide tris(trifluoroacetate);

4-[((1RS,2SR)-2-{[(amino(imino)methyl]amino}cyclohexyl)amino]-N-(1-benzylpyrrolidin-3-yl)-N,6-dimethylquinazoline-2-carboxamide tris(trifluoroacetate);

4-[((1RS,2SR)-2-{[amino(imino)methyl]amino}cyclohexyl)amino]-N-{2-[(2-furylmethyl)thio]ethyl}-6-methylquinazoline-2-carboxamide bis(trifluoroacetate);

4-[((1RS,2SR)-2-{[amino(imino)methyl]amino}cyclohexyl)amino]-6-methyl-N-[(5-methylpyrazin-2-yl)methyl]quinazoline-2-carboxamide bis(trifluoroacetate);

4-[((1RS,2SR)-2-{[amino(imino)methyl]amino}cyclohexyl)amino]-6-methyl-N-(tetrahydrofuran-2-ylmethyl)quinazoline-2-carboxamide bis(trifluoroacetate);

4-[((1RS,2SR)-2-{[amino(imino)methyl]amino}cyclohexyl)amino]-6-methyl-N-[4-(trifluoromethyl)benzyl]quinazoline-2-carboxamide bis(trifluoroacetate);

4-[((1RS,2SR)-2-{[amino(imino)methyl]amino}cyclohexyl)amino]-6-methyl-N-[4-(trifluoromethoxy)benzyl]quinazoline-2-carboxamide bis(trifluoroacetate);

4[((1RS,2SR)-2-{[amino(imino)methyl]amino}cyclohexyl)amino]-N-(6-chloropyridin-3-yl)-6-methylquinazoline-2-carboxamide tris(trifluoroacetate);

4-[((1RS,2SR)-2-{[amino(imino)methyl]amino}cyclohexyl)amino]-N-[4-(aminomethyl)benzyl]-6-methylquinazoline-2-carboxamide tris(trifluoroacetate);

4-[((1RS,2SR)-2-{[amino(imino)methyl]amino}cyclohexyl)amino]-6-methyl-N-(2-(pyridin-2-yl)ethyl) quinazoline-2-carboxamide tris(trifluoroacetate);

4-[((1RS,2SR)-2-{[amino(imino)methyl]amino}cyclohexyl)amino]-N-{[(2S)-1-ethylpyrrolidin-2-yl]methyl}-6-methylquinazoline-2-carboxamide tris(trifluoroacetate);

4-[((1RS,2SR)-2-{[amino(imino)methyl]amino}cyclohexyl)amino]-N-[3-fluoro-5-(trifluoromethyl)benzyl]-6-methylquinazoline-2-carboxamide bis(trifluoroacetate);

4-[((1RS,2SR)-2-{[amino(imino)methyl]amino}cyclohexyl)amino]-N-{2-[4-(aminosulfonyl)phenyl]ethyl}-6-methylquinazoline-2-carboxamide bis(trifluoroacetate);

4-[((1RS,2SR)-2-{[amino(imino)methyl]amino}cyclohexyl)amino]-N-[2-(1,3-benzodioxol-5-yl)ethyl]-6-methylquinazoline-2-carboxamide bis(trifluoroacetate);

4-[((1RS,2SR)-2-{[amino(imino)methyl]amino}cyclohexyl)amino]-N-{2-[benzyl(methyl)amino]ethyl}-N,6-dimethylquinazoline-2-carboxamide tris(trifluoroacetate);

4-[((1RS,2SR)-2-{[amino(imino)methyl]amino}cyclohexyl)amino]-6-methyl-N-(thiophen-2-ylmethyl) quinazoline-2-carboxamide bis(trifluoroacetate);

4-[((1RS,2SR)-2-{[amino(imino)methyl]amino}cyclohexyl)amino]-N-[5-(ethylthio)-1,3,4-thiadiazol-2-yl]-6-methylquinazoline-2-carboxamide bis(trifluoroacetate);

4-[((1RS,2SR)-2-{[amino(imino)methyl]amino}cyclohexyl)amino]-6-methyl-N-[2-(2-phenoxyphenyl)ethyl] quinazoline-2-carboxamide bis(trifluoroacetate);

4-[((1RS,2SR)-2-{[amino(imino)methyl]amino}cyclohexyl)amino]-N-[2-(1,1'-biphenyl-4-yl) ethyl]-6-methylquinazoline-2-carboxamide bis(trifluoroacetate);

4-[((1RS,2SR)-2-{[amino(imino)methyl]amino}cyclohexyl)amino]-6-methyl-N-(5-nitro-1,3-thiazol-2-yl) quinazoline-2-carboxamide bis(trifluoroacetate);

4-[((1RS,2SR)-2-{[amino(imino)methyl]amino}cyclohexyl)amino]-N-[3,5-bis(trifluoromethyl)benzyl]-6-methylquinazoline-2-carboxamide bis(trifluoroacetate);

4-[((1RS,2SR)-2-{[amino(imino)methyl]amino}cyclohexyl)amino]-6-methyl-N-[2-(2-methylphenyl)ethyl] quinazoline-2-carboxamide bis(trifluoroacetate);

4-[((1RS,2SR)-2-{[amino(imino)methyl]amino}cyclohexyl)amino]-6-methyl-N-(3-(morpholin-4-yl)propyl) quinazoline-2-carboxamide bis(trifluoroacetate);

4-[((1RS,2SR)-2-{[amino(imino)methyl]amino}cyclohexyl)amino]-N-(3,5-di-tert-butylphenyl)-6-methylquinazoline-2-carboxamide bis(trifluoroacetate);

4-[((1RS,2SR)-2-{[amino(imino)methyl]amino}cyclohexyl)amino]-N-(6-methoxypyridin-3-yl)-6-methylquinazoline-2-carboxamide tris(trifluoroacetate);

4-[((1RS,2SR)-2-{[amino(imino)methyl]amino}cyclohexyl)amino]-6-methyl-N-[3-(4-methylpiperazin-1-yl) propyl]quinazoline-2-carboxamide bis(trifluoroacetate);

4-[((1RS,2SR)-2-{[(amino(imino)methyl]amino}cyclohexyl)amino]-N-(3,4-dimethoxyphenyl)-6-methylquinazoline-2-carboxamide bis(trifluoroacetate);

4-[((1S,2R)-2-{[amino(imino)methyl]amino}cyclohexyl) amino]-N-(4-methoxyphenyl)-8-methylquinazoline-2-carboxamide dihydrochloride;

4-[((1S,2R)-2-{[amino(imino)methyl]amino}cyclohexyl) amino]-6-methyl-N-(2-oxo-2,3-dihydro-1H-benzimidazol-5-yl)quinazoline-2-carboxamide dihydrochloride;

4-[((1S,2R)-2-{[amino(imino)methyl]amino}cyclohexyl) amino]-6-methyl-N-(2-(pyridin-2-yl)ethyl)quinazoline-2-carboxamide trihydrochloride;

4-[((1S,2R)-2-{[amino(imino)methyl]amino}cyclohexyl) amino]-6-methyl-N-(2-(morpholin-4-yl)ethyl)quinazoline-2-carboxamide trihydrochloride;

4-[((1S,2R)-2-{[amino(imino)methyl]amino}cyclohexyl) amino]-6-methyl-N-(5-methyl-1,3-thiazol-2-yl) quinazoline-2-carboxamide trihydrochloride;

4-[((1S,2R)-2-{[amino(imino)methyl]amino}cyclohexyl) amino]-6-methyl-N-quinolin-6-ylquinazoline-2-carboxamide trihydrochloride;

4-[((1S,2R)-2-{[amino(imino)methyl]amino}cyclohexyl) amino]-N-(1H-benzimidazol-2-ylmethyl)-6-methylquinazoline-2-carboxamide trihydrochloride;

4-[((1S,2R)-2-{[amino(imino)methyl]amino}cyclohexyl) amino]-6-methyl-N-[(1-(pyridin-2-yl)pyrrolidin-2-yl) methyl]quinazoline-2-carboxamide trihydrochloride;

4-[((1S,2R)-2-{[amino(imino)methyl]amino}cyclohexyl) amino]-6-methyl-N-[2-(4-methyl-1,3-thiazol-5-yl) ethyl]quinazoline-2-carboxamide trihydrochloride;

4-[((S,2R)-2-{[amino(imino)methyl]amino}cyclohexyl)amino]-N-[2-(3,5-dimethylisoxazol-4-yl)ethyl]-6-methylquinazoline-2-carboxamide;

4-[((1S,2R)-2-{[amino(imino)methyl]amino}cyclohexyl)amino]-6-methyl-N-[4-(trifluoromethoxy)benzyl]quinazoline-2-carboxamide dihydrochloride;

4-[((1S,2R)-2-{[amino(imino)methyl]amino}cyclohexyl)amino]-6-methyl-N-[2-(3-thienyl)ethyl]quinazoline-2-carboxamide dihydrochloride;

4-[((1S,2R)-2-{[amino(imino)methyl]amino}cyclohexyl)amino]-6-methyl-N-(2-(pyridin-4-yl)ethyl)quinazoline-2-carboxamide trihydrochloride;

4-[((1S,2R)-2-{[amino(imino)methyl]amino}cyclohexyl)amino]-6-methyl-N-(3-pyridin-3-ylpropyl)quinazoline-2-carboxamide trihydrochloride;

4-[((1S,2R)-2-{[amino(imino)methyl]amino}cyclohexyl)amino]-6-methyl-N-[2-(trifluoromethyl)benzyl]quinazoline-2-carboxamide dihydrochloride;

4-[((1S,2R)-2-{[amino(imino)methyl]amino}cyclohexyl)amino]-N-[3,5-bis(trifluoromethyl)benzyl]-6-methylquinazoline-2-carboxamide dihydrochloride;

4-[((1S,2R)-2-{[amino(imino)methyl]amino}cyclohexyl)amino]6-methyl-N-[3-(trifluoromethyl)benzyl]quinazoline-2-carboxamide dihydrochloride;

4-[((1RS,2SR)-2-{[amino(imino)methyl]amino}cyclohexyl)amino]-N-(2-[ethyl(3-methylphenyl)amino]ethyl}-6-methylquinazoline-2-carboxamide bis(trifluoroacetate);

4-[((1RS,2SR)-2-{[amino(imino)methyl]amino}cyclohexyl)amino]-6-methyl-N-(2-(pyridin-4-yl)ethyl)quinazoline-2-carboxamide tris(trifluoroacetate);

4-[((1RS,2SR)-2-{[amino(imino)methyl]amino}cyclohexyl)amino]-N-(2-furylmethyl)-6-methylquinazoline-2-carboxamide bis(trifluoroacetate);

4-[((1RS,2SR)-2-{[amino(imino)methyl]amino}cyclohexyl)amino]-N-(1H-benzimidazol-2-ylmethyl)-6-methylquinazoline-2-carboxamide tris(trifluoroacetate);

4-[((1RS,2SR)-2-{[amino(imino)methyl]amino}cyclohexyl)amino]-6-methyl-N-(2-(pyridin-3-yl)ethyl)quinazoline-2-carboxamide tris(trifluoroacetate);

4-[((1RS,2SR)-2-{[amino(imino)methyl]amino}cyclohexyl)amino]-6-methyl-N-[(5-methylpyrazin-2-yl)methyl]quinazoline-2-carboxamide tris(trifluoroacetate);

4-[((1RS,2SR)-2-{[amino(imino)methyl]amino}cyclohexyl)amino]-6-methyl-N-(2-oxotetrahydrofuran-3-yl)quinazoline-2-carboxamide bis(trifluoroacetate);

4-[((1RS,2SR)-2-{[amino(imino)methyl]amino}cyclohexyl)amino]-6-methyl-N-(2-(pyrrolidin-1-yl)ethyl)quinazoline-2-carboxamide tris(trifluoroacetate); and 4-[(2-{[amino(imino)methyl]amino}phenyl)amino)-N-(4-methoxyphenyl)-6-methylquinazoline-2-carboxamide dihydrochloride.

17. A method of treating a disease associated with itching, wherein the disease is selected from pruritic dermatitis associated with skin lesion and pruritus cutaneous, comprising administering to a subject in need thereof an effective amount of the quinazoline derivative represented by the general formula (1b) of claim 1 or a salt thereof.

18. The method of claim 17, wherein the pruritic dermatitis associated with skin lesion is selected from atopic dermatitis, urticaria, psoriasis, xeroderma, and trichophytia.

* * * * *